(12) United States Patent
Lyday

(10) Patent No.: US 12,059,443 B2
(45) Date of Patent: *Aug. 13, 2024

(54) METHOD FOR TREATING CANCER USING DENGUE VIRUS SEROTYPE 1 (DENV-1)

(71) Applicant: PrimeVax Immuno-Oncology, Inc., Orange, CA (US)

(72) Inventor: Bruce W. Lyday, Orange, CA (US)

(73) Assignee: Prime Vax Immuno-Oncology, Inc., Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/130,349

(22) Filed: Dec. 22, 2020

(65) Prior Publication Data

US 2021/0236568 A1    Aug. 5, 2021

Related U.S. Application Data

(63) Continuation of application No. 16/460,629, filed on Jul. 2, 2019, now abandoned, which is a continuation of application No. PCT/US2018/012408, filed on Jan. 4, 2018.

(51) Int. Cl.
| | |
|---|---|
| *A61K 35/76* | (2015.01) |
| *A61K 9/00* | (2006.01) |
| *A61K 9/19* | (2006.01) |
| *A61P 35/00* | (2006.01) |
| *C12N 7/00* | (2006.01) |

(52) U.S. Cl.
CPC ............ *A61K 35/76* (2013.01); *A61K 9/0019* (2013.01); *A61K 9/19* (2013.01); *A61P 35/00* (2018.01); *C12N 7/00* (2013.01); *C12N 2770/24121* (2013.01); *C12N 2770/24132* (2013.01)

(58) Field of Classification Search
CPC .......... A61K 35/00; C12N 2770/24121; C12N 2770/24132
See application file for complete search history.

(56) References Cited

U.S. PATENT DOCUMENTS

| | | | |
|---|---|---|---|
| 6,048,686 A * | 4/2000 | Lyday ................. | C12N 7/00 435/5 |
| 6,511,667 B1 | 1/2003 | Eckels et al. | |
| 6,524,587 B1 * | 2/2003 | Lyday .................. | A61K 39/39 424/278.1 |
| 7,217,418 B2 | 5/2007 | Eckels et al. | |
| 8,415,152 B2 | 4/2013 | Muhlradt et al. | |
| 8,889,118 B2 | 11/2014 | Okano et al. | |
| 9,730,989 B2 * | 8/2017 | Lyday .................. | A61P 17/00 |
| 9,849,167 B2 * | 12/2017 | Lyday .................. | A61P 43/00 |
| 10,159,727 B2 * | 12/2018 | Lyday .................. | A61P 37/04 |
| 10,357,553 B2 * | 7/2019 | Lyday .................. | A61P 15/00 |
| 10,675,304 B2 * | 6/2020 | Lyday .................. | C12N 7/00 |
| 10,946,080 B2 * | 3/2021 | Lyday .................. | A61K 39/12 |
| 11,357,795 B2 * | 6/2022 | Lyday .................. | A61K 35/76 |
| 2002/0146396 A1 | 10/2002 | Albert et al. | |
| 2007/0065457 A1 | 3/2007 | Krieg et al. | |
| 2007/0082400 A1 | 4/2007 | Healey et al. | |
| 2013/0089567 A1 | 4/2013 | Whitehead et al. | |
| 2013/0183343 A1 | 7/2013 | Czerniecki et al. | |
| 2015/0166532 A1 | 6/2015 | Gray et al. | |
| 2016/0058852 A1 | 3/2016 | Ter et al. | |
| 2019/0247479 A1 | 8/2019 | Lyday | |
| 2019/0298764 A1 | 10/2019 | Lyday | |

FOREIGN PATENT DOCUMENTS

| | | |
|---|---|---|
| WO | WO-0057705 A1 | 10/2000 |
| WO | WO-0156599 A2 | 8/2001 |
| WO | WO-2008022196 A2 | 2/2008 |
| WO | WO-2012160199 A1 | 11/2012 |
| WO | WO-2013127976 | 9/2013 |
| WO | WO-2013188315 A1 | 12/2013 |
| WO | WO-2014018113 A1 | 1/2014 |
| WO | WO-2016179475 A1 | 11/2016 |
| WO | WO-2017004567 A1 | 1/2017 |
| WO | WO-2017053873 A1 | 3/2017 |
| WO | WO-2018093907 A1 | 5/2018 |
| WO | WO-2018129202 A1 | 7/2018 |
| WO | WO-2018232166 A1 | 12/2018 |

OTHER PUBLICATIONS

Januškevičienė, I., and V. Petrikaitė, 2019, Heterogeneity of breast cancer: The importance of interaction between different tumor cell populations, Life Sciences 239:1-10.*

Liu, W.-j., et al., 2020, Drug resistance to targeted therapeutic strategies in non-small cell lung cancer, Pharmacol. Therap. 206:1-18.*

Wang, W.-K., et al., 2002, Dengue type 3 virus in plasma is a population of closely related genomes: Quasispecies, J. Virol. 76(9): 4662-4665.*

Andersen et al. Spontaneous immunity against Bcl-xL in cancer patients. J Immunol 175(4):2709-2714 (2005).

Angarone. Epidemiology and Prevention of Viral Infections in Patients with Hematologic Malignancies. Infect Disord Drug Targets 11(1):27-33 (2011).

Angsubhakorn et al. Neurovirulence detection of dengue virus using rhesus and cynomolgus monkeys. J Virol Methods 18(1):13-24 (1987).

(Continued)

*Primary Examiner* — Jeffrey S Parkin

(74) *Attorney, Agent, or Firm* — Greenberg Traurig, LLP

(57) ABSTRACT

Described herein are compositions and methods for treating a disease, particularly a cancer, with a Dengue Virus and, optionally, primed dendritic cells recognizing a tumor antigen. Lysis protocols are described where the lysis does not result in complete or less than complete lysis of cells in order to provide cell surface molecules maintained in a cell surface-embedded state. Non-lethal Dengue virus strains are also provided for therapeutic purposes.

12 Claims, 16 Drawing Sheets

Specification includes a Sequence Listing.

(56) References Cited

OTHER PUBLICATIONS

Anguille et al. Clinical use of dendritic cells for cancer therapy. Lancet Oncol 15:e257-267 (2014).
Anikeeva et al. Mechanisms Controlling Granule-mediated Cytolytic Activity of Cytotoxic T Lymphocytes. Immunol Res 51(2-3):183-194 (2011).
Armstrong et al. Efficiency of dengue serotype 2 virus strains to infect and disseminate in Aedes aegypti. Am J Trop Med Hyg 68:539-544 (2003).
Balmaseda et al. Serotype-Specific Differences in Clinical Manifestations of Dengue. Am J Trop Med Hyg 74(3):489-456 (2006).
Bente et al. Dengue Fever in Humanized NOD/SCID Mice. J Virol 79(21):13797-13799 (2005).
Bozza et al. Multiplex cytokine profile from dengue patients: MIP-1b and IFN-gamma as predictive factors for severity. BMC Infect Dis 8:86-93 (2008).
Cabrera et al. Analysis of HLA expression in human tumor tissues. Cancer Immunol Immunother 52:1-9 (2003).
Carreno et al. IL-12p70-producing patient DC vaccine elicits Tc1-polarized immunity. J Clin Invest 123(8):3383-3394 (2013).
Chakraborty et al. Emergence of regulatory CD4+ T cell responses to repetitive stimulation with antigen-presenting cells in vitro: implications in designing APC-based tumor vaccines. J Immunol 162:5576-5583 (1999).
Chalaem et al. Characterization of a Chikungunya virus strain isolated from banked patients' sera. Virol J 13(1):150 (2016).
Chang et al. Production of IL-1 by human monocytes exposed to dengue virus. J Infect Dis 170:811-817 (1994).
Chen et al. Activation of terminally differentiated human monocytes/macrophages by dengue virus: productive infection, hierarchical production of innate cytokines and chemokines, and the synergistic effect of lipopolysaccharide. J Virology 76:9877-9887 (2002).
Chiang et al. A dendritic cell vaccine pulsed with autologous hypochlorous acid-oxidized ovarian cancer lysate primes effective broad antitumor immunity: from bench to bedside. Clin Cancer Res 19(17):4801-4815 (2013).
Chiang et al. Optimizing parameters for clinical-scale production of high IL-12 secreting dendritic cells pulsed with oxidized whole tumor cell lysate. J Transl Med 14;9:198 (2011).
Crooks et al. The use of the Karnofsky Performance Scale in determining outcomes and risk in geriatric outpatients. J Gerontol 46:M139-M144 (1991).
De Haan et al. Measuring quality of life in stroke. Stroke 24:320-327 (1993).
Den Boer et al. Longevity of antigen presentation and activation status of APC are decisive factors in the balance between CTL Immunity Vs. Tolerance. J Immunol 167:2252-2258 (2001).
Dengue: Guidelines for Diagnosis, Treatment, Prevention and Control. World Health Organization (160 pgs) (2009).
Dequen et al. Systematic review and network meta-analysis of overall survival comparing 3 mg/kg Ipilimumab with alternative therapies in the management of pre-treated patients with unresectable Stage III or IV melanoma. Oncologist 17(11):1376-1385 (2012).
Diamond et al. Infection of human cells by dengue virus is modulated by different cell types and viral strains. J Virology 74(17):7814-7823 (2000).
Dillman et al. High-dose IL2 in metastatic melanoma: better survival in patients immunized with antigens from autologous tumor cell lines. Cancer Biother Radiopharm 29(2):53-57 (2014).
Dohnal et al. CD40 ligation restores type 1 polarizing capacity in TLR4-activated dendritic cells that have ceased interleukin-12 expression. J Cell Mol Med 13(8B):1741-1750 (2009).
Doyle et al. 9.1.1 Principles Governing the Use of Cancer Chemotherapy in Palliative Care. Oxford Textbook of Palliative Medicine, Oxford University Press. (p. 255) (1993).
Draghiciou et al. Therapeutic immunization and local low-dose tumor irradiation, a reinforcing combination. Int J Cancer 177(3):311-327 (2012).
Dudek et al. Inducers of Immunogenic Cancer Cell Death. Cytokine Growth Factor Rev 24(4):319-333 (2013).
Eckels et al. Isolation of a Temperature—Sensitive Dengue—2 Virus Under Conditions Suitable for Vaccine Development. Infect Immun 14(5):1221-1227 (1976).
Edelman et al. A live attenuated dengue-1 vaccine candidate (45AZ5) passaged in primary dog kidney cell culture is attenuated and immunogenic for humans. J Infect Dis. 170(6):1448-1455 (1994).
Ellem et al. The labyrinthine ways of cancer immunotherapy-T cell, tumor cell encounter: 'How do I lose thee? Let me count the ways'. Ad Cancer Res 75:203-249 (1998).
Endy. Human immune responses to dengue virus infection: lessons learned from prospective cohort studies. Front Immunol 5:183 (2014).
Flavell et al. The polarization of immune cells in the tumour environment by TGFβ. Nat Rev Immunol 10(8):554-567 (2010).
Fracol et al. Response to HER-2 pulsed DC1 vaccines is predicted by both HER-2 and estrogen receptor expression in DCIS. Ann Surg Oncol 20(10):3233-3239 (2013).
Franciszkiewicz et al. CD103 or LFA-1 engagement at the immune synapse between cytotoxic T cells and tumor cells promotes maturation and regulates T-cell effector functions. Cancer Res 73(2):617-628 (2013).
Gabrilovitch et al. Dendritic cells in antitumor immune responses. II. Dendritic cells grown from bone marrow precursors, but not mature DC from tumor-bearing mice, are effective antigen carriers in the therapy of established tumors. Cell Immunol 70(1):111-119 (1996).
Ganss et al. Combination of T-cell therapy and trigger of inflammation induces remodeling of the vasculature and tumor eradication. Cancer Research 62:1462-1470 (2002).
Genevive et al. CD40-CD40 Ligand Interaction between Dendritic Cells and CD8+ T Cells Is Needed to Stimulate Maximal T Cell Responses in the Absence of CD4+ T Cell Help. J Immunol 178(5):2844-2852 (2007).
George et al. Chapter 5: Clinical spectrum of dengue infection. Dengue and Dengue Hemorrhagic Fever (Gubler and Kuno, CAB International) (25 pgs) (1997).
Gervais et al. In vitro antitumor lymphocyte generation using dendritic cells and innate immunity mechanisms as tumor cell treatments. Anticancer Res 27(4B):2385-2392 (2007).
Gottardis et al. Estradiol-stimulated growth of MCF-7 tumors implanted in athymic mice: a model to study the tumoristatic action of tamoxifen. J Steroid Biochem 30: 311-314 (1988).
Gupta et al. Acute disseminated encephalomyelitis associated with dengue infection, a case report with literature review. J Neurol Sci 335(1-2):216-218 (2013).
Habaragamuwa et al. N-acetylcystein in dengue-associated severe hepatitis. Indian J Crit Care Med 18(3):181-184 (2014).
Hahn et al. Nucleotide sequence of dengue 2 RNA and comparison of the encoded proteins with those of other flaviviruses. Virology 162:167-180 (1988).
Halstead. Etiologies of the Experimental Dengues of Siler and Simmons. Am J Trop Med Hys 23:974-982 (1974) (http://www.ajtmh.org/content/23/5/974.long).
Harris et al. Rapid subtyping of dengue viruses by restriction site-specific (RSS)-PCR. Virology 253:86-95 (1999).
Heylmann et al. Radiation sensitivity of human and murine peripheral blood lymphocytes, stem, and progenitor cells. Biochim Biophys Acta 1846(1):121-129 (2014) .
Hober et al. High levels of sTNFR p75 and TNF alpha in dengue-infected patients. Microbiol Immunol 40:569-573 (1996).
Hollen et al. Measurement of quality of life in patients with lung cancer in multicenter trials of new therapies. Cancer 73:2087-2098 (1994).
Hung. Fluid Management for dengue in children. Paediatrics and Child Health 32(S-1):39-42 (2012).
Islas-Rodríguez et al. Effect of in vitro infection with dengue virus (DEN-2) on various cellular immune response functions in the mouse. Archivos de Investiga cion Medica 21(2):87-93 (1990) (English Abstract).
Janikashvili et al. Personalized dendritic cell-based tumor immunotherapy. Immunotherapy 2(1):57-68 (2010).

(56) References Cited

OTHER PUBLICATIONS

Jing et al. Combined immune checkpoint protein blockade and low dose whole body irradiation as immunotherapy for myeloma. J Immuno Ther Cancer 3(1):2 (15 pgs) (2015).
Kaka et al. Using Dendritic Cell Maturation and IL-12 Producing Capacity as Markers of Function: A Cautionary Tale. J Immunother 31(4):359-369 (2008).
Kawasaki et al. Toll-Like Receptor Signaling Pathways. Fron Immunol 5:461 (2014).
Kelley et al. Dengue Hemorrhagic Fever-Associated Immunomediators Induced via maturation of Dengue Virus Nonstructural 4B Protein in Monocytes Modulate Endothelial Cell Adhesion Molecules and Human Microvascular Endothelial Cells Permeability. Virology 422(2):326-337 (2012).
Khan et al. The Evolving Role of Radiation Therapy in the Management of Malignant Melanoma. Int J Radiat Oncol Biol Phys 80(3):645-654 (2011).
Kuo et al. Liver biochemical tests and dengue fever. Am J Trop Med Hyg 47:265-270 (1992).
Kurane et al. Activation of T lymphocytes in dengue virus infections. High levels of soluble interleukin 2 receptor, soluble CD4, soluble CD8, interleukin 2, and interferon-gamma in sera of children with dengue. J Clin Invest 88:1473-1480 (1991).
Kurane et al. Dengue virus infection of human skin fibroblasts in vitro production of IFN-Beta, IL-6, and GM-CSF. Arch Virol 124:21-30 (1992).
Kurlander et al. A functional comparison of mature human dendritic cells prepared in fluorinated ethylene-propylene bags or polystyrene flasks. Transfusion 46(9):1494-1504 (2006).
Kuss et a. Clinical significance of decreased zeta chain expression in peripheral blood lymphocytes of patients with head and neck cancer. Clin Cancer Res 5:329-334(1999).
Lambert et al. Intradermal vaccine delivery: will new delivery systems transform vaccine administration? Vaccine 26:3197-3208 (2008).
Lee et al. Acute myocarditis in dengue hemorrhagic fever: a case report and review of cardiac complications in dengue-affected patients. Int J Infect Dis 14:e919-e922 (2010).
Lee et al. Clinical characteristics, risk factors, and outcomes in adults experiencing DHF complicated with acute renal failure. Am J Trop Med Hyg 80(4): 651-655 (2009).
Leitmeyer et al. Dengue virus structural changes that correlate with pathogenesis. J Virol 73:4738-4747 (1999).
Lesterhaus et al. Dendritic Cell vaccines in melanoma: from promise to proof? Crit Rev Oncol Hematol 66(2):118-134 (2008).
Linette et al. Cardiovascular toxicity and titin cross-reactivity of affinity-enhanced T cells in myeloma and melanoma. Blood 122(6):863-871 (2013).
Lizarraga et al. Dengue-associated kidney disease. J Nephropathol 3(2):57-62 (2014).
Lum et al. Dengue-associated adult respiratory distress syndrome. Ann Trop Paediatr 15(4):335-339 (1995).
Lutz et al. An advanced culture method for generating large quantities of highly pure dendritic cells from mouse bone marrow. J Immunol Methods 223:77-92 (1999).
Lövgren et al. Enhanced stimulation of human tumor-specific T cells by dendritic cells matured in the presence of interferon-γ and multiple toll-like receptor agonists. Cancer Immunol Immunother 66(10):1333-1344 (2017).
Lyday et al. Overcoming tumor immune evasion with an unique arbovirus. J Transl Med 13:3 (2015) (12 pgs).
Ma et al. The TLR7 agonists imiquimod and gardiquimod improve DC-based immunotherapy for melanoma in mice. Cell Mol Immunol 7(5):381-388 (2010).
MACS® GMP Cell Differentiation Bag. Miltenyi Biotec Product Insert. Issued: Aug. 2012 (2 pgs).
Malavige et al. T cell responses in dengue viral infections. J Clin Virol 58(4):605-611 (2013).
Malik et al. Dengue encephalopathy-still and enigma? J Infect Dev Ctries 8(8): 1076-1078 (2014).

Markiewicz et al. IL-12 enhances CTL synapse formation and induces self-reactivity. J Immunol 182(3):1351-1361 (2009).
Matthew et al. Dominant recognition by human CD8+ CTL of dengue virus non-structural proteins NS3 and NS1.2a. J Clin Invest 98:1684-1691 (1996).
McKee et al. Lack of attenuation of a candidate Dengue-1 vaccine (45AZ5), in human volunteers. Am J Trop Med Hyg Mar. 36:435-442 (1987).
Media For Multiplitoplasma Viroids Is Not Rare—Causative Agent (available at https://www.alpfmedical.info/causative-agent/i-ptg.html) ALPF Medical Research (5 pgs) (updated Jul. 21, 2017) .
Mettler et al. Virus Inoculation in Mice Bearing Ehrlich Ascitic Tumors: Antigen Prouction and Tumor Regression. Infect Immun 37(1):23-27 (1982).
Mittendorf et al. Final report of the phase I/II clinical trial of the E75 (nelipepimut-S) vaccine with booster inoculations to prevent disease recurrence in high-risk breast cancer patients. Ann Oncol 25(9):1735-1742 (2014).
Mizoguchi et al. Alterations in signal transduction molecules in T lymphocytes from tumor-bearing mice. Science 258:1795-1798 (1992).
Morse et al. Migration of human DC after injection in Patients with Metastatic Malignancies. Cancer Res 59:56-58 (1999).
Nakai et al. Immunoregulatory T cells in the peripheral blood of melanoma patients treated with melanoma antigen-pulsed dendritic cell vaccination. J Dermatol Sci 54:31-37 (2009).
Napolitani et al. Selected Toll-like receptor agonist combinations synergistically trigger a T helper type 1-polarizing program in dendritic cells. Nat Immunol 6(8): 769-776 (2005).
Nava et al. An optimized method for manufacturing a clinical-scale Dendritic Cell-based vaccine for the treatment of Glioblastoma. PLoS One 7(12):e52301 (2012).
Nielsen. The Relationship of intersecting immunological components in Dengue pathogenesis. Virol J 6:1-7 (2009).
Nocera et al. Restoring Lost Anti-HER-2 Th1 Immunity in Breast Cancer: A Crucial Role for Th1 Cytokines in Therapy and Prevention. Front Pharmacol 7:356 (2016).
Nunes et al. Emergence and potential for spread of Chikungunya virus in Brazil. BMC Medicine 13:102 (2015).
Oken et al. Toxicity and Response Criteria of the Eastern Cooperative Oncology Group. Am J Clin Oncol 5:649-655 (1982).
Oleinika et al. Suppression, subversion, and escape: the role of regulatory T cells in cancer progression. Clin Exp Immunol 171:36-45 (2012).
Olzanski. Current and Future Roles of Targeted Therapy and Immunotherapy in Advanced Melanoma. J Manag Care Pharm 20(4):346-354 (2014).
Osborne et al. Effects of estrogens and antiestrogens on growth of human breast cancer cells in athymic nude mice. Cancer Res 45:584-590 (1985).
O'Toole et al. Evaluating cancer patients for rehabilitation potential. West J Med 155:384-387 (1991).
Park et al. Radiation-induced vascular damage in tumors: implications of vascular damage in ablative hypofractionated radiotherapy (SBRT and SRS). Radiat Res 177(3):311-327 (2012).
Pasca et al. Role of Interleukin-12 in patients with dengue hemorrhagic fever. FEMS Immunol Med Microbiol 28:151-155 (2000).
Paustian et al. Effect of multiple activation stimuli on the generation of Th1-polarizing dendritic cells. Hum Immuon 72(1):24-31 (2011).
PCT/US2016/040787 International Preliminary Report on Patentability dated Jan. 11, 2018.
PCT/US2016/040787 International Search Report and Written Opinion dated Sep. 22, 2016.
PCT/US2016/053554 International Preliminary Report on Patentability dated Apr. 5, 2018.
PCT/US2016/053554 International Search Report and Written Opinion dated Feb. 3, 2017.
PCT/US2016/053554 Invitation to Pay Additional Fees dated Nov. 28, 2016.
PCT/US2017/061810 International Search Report and Written Opinion dated Mar. 15, 2018.
PCT/US2017/061810 Invitation to Pay Additional Fees dated Jan. 22, 2018.

(56) References Cited

OTHER PUBLICATIONS

PCT/US2018/012408 International Search Report and Written Opinion dated Mar. 29, 2018.
Pfeiffer. Dissertation—Generation of effective designer dendritic cells for therapeutic cancer vaccination using RNA electroporation. The Faculty of Science, University of Erlangen-Nuremberg (146 pgs) (2013) (w/English translation).
Prestwich et al. The case of oncolytic viruses versus the immune system: waiting on the judgment of Solomon. Hum Gene Ther 20(10):1119-1132 (2009).
Quatromonie et al. The timing of TGF-βinhibition affects the generation of antigen-specific CD8+ T cells. BMC Immunol 14:30 (2013).
Rajat et al. Unusual manifestations in dengue outbreak 2009, Delhi, India. J Communicable Dis 42(4):255-261 (2010).
Rigau-Perez et al. Dengue activity in Puerto Rico, 1990. Puerto Rico Health Science Journal 11(2):65-68 (1992).
Rouas et al. Dendritic cells generated in clinical grade bags strongly differ in immune functionality when compared with classical DCs generated in plates. J Immunother 33(4):352-363 (2010).
Santos et al. Dendritic Cell-Based Cancer Vaccines. J Immunol 200(2):443-449 (2018).
Sarathy et al. Mouse models of dengue virus infection for vaccine testing. Vaccine 33(50):7051-7060 (2015).
Schag et al. Karnofsky performance status revisited: Reliability, validity, and guidelines. J Clin Oncol 2:187-193 (1984).
Sharma et al. Guillain-Barre syndrome occurring during dengue fever. J Indian Med Assoc 109(9):675 and 682 (2011).
Sheikh et al. Sipuleucel-T immune parameters correlate with survival: an analysis of the randomized phase 3 clinical trials in men with castration-resistant prostate cancer. Cancer Immunol Immunother 62(1):137-147 (2013).
Shresta et al. Critical roles for both STAT1-dependent and STAT1-independent pathways in the control of primary dengue virus infection in mice. J Immunol 175:3946-3954 (2005).
Singhi et al. Dengue and Dengue Hemorrhagic Fever: management issues in an intensive care unit. J Pediatr (Rio J) 83(Supp 2):S22-S35 (2007).
Sinkovics et al. New Developments in the Virus Therapy of Cancer: A Historical Review. Intervirology 36:193-214 (1993).
Sondak et al. Allogeneic and autologous melanoma vaccines: where have we been and where are we going? Clin Cancer Res 12(7 Pt 2):2337s-2341s (2006).
Sorlie et al. Gene expression patterns of breast carcinomas distinguish tumor subclasses with clinical implications. PNAS USA 98:10869-10874 (2001).
Stanton et al. Clinical significance of tumor-infiltrating lymphocytes in breast cancer. J Immunother Cancer 4:59 (2016).
Straussman et al. Tumour micro-environment elicits innate resistance to RAF inhibitors through HGF secretion. Nature 487:500-504 (2012).
Tan et al. Subcutaneous infection with non-mouse adapted Dengue virus D2Y98P strain induces systemic vascular leakage in AG129 mice. Ann Acad Med Singapore 40(12):523-532 (2011).
Taweechaisupapong et al. Langerhans cell density and serological changes following intradermal immunisation of mice with dengue 2 virus. J Med Microbiol 45:138-145 (1996).
Turcotte et al. Immunotherapy for metastatic solid cancers. Adv Surg 45:341-360 (2011).
"Turnis, et al., "Enhancement of dendritic cells as vaccines for cancer" (2010) Immunotherapy, vol. 2, pp. 847-862".
Turnis et al. Enhancement of dendritic cells as vaccines for cancer. Immunotherapy 2(6):847-862 (2010).
U.S. Appl. No. 15/200,751 Office Action dated Feb. 7, 2017.
U.S. Appl. No. 15/275,073 Office Action dated Aug. 15, 2018.
U.S. Appl. No. 15/275,073 Office Action dated Aug. 30, 2019.
U.S. Appl. No. 15/275,073 Office Action dated Jan. 17, 2020.
U.S. Appl. No. 15/275,073 Office Action dated Jan. 28, 2019.
U.S. Appl. No. 15/275,073 Office Action dated Jul. 14, 2017.
U.S. Appl. No. 15/275,073 Office Action dated Mar. 31, 2017.
U.S. Appl. No. 15/639,632 Office Action dated Aug. 3, 2017.
U.S. Appl. No. 15/799,793 Office Action dated Dec. 13, 2017.
U.S. Appl. No. 15/799,793 Office Action dated May 25, 2018.
U.S. Appl. No. 16/172,487 Office Action dated Dec. 14, 2018.
U.S. Appl. No. 16/413,444 Office Action dated Aug. 19, 2019.
U.S. Appl. No. 16/413,444 Office Action dated Nov. 20, 2019.
Valerio et al. Hemorrhagic exanthema due to dengue virus induced by Acetylsalicylic acid. An Sist Sancit Navar 29(3):439-442 (2006).
Van Mierlo et al. Activation of dendritic cells that cross-present tumor-derived antigen licenses CD8+ CTL to cause tumor destruction. J Immunol 173:6753-6759 (2004).
Vaughn et al. Dengue viremia titer, Antibody Response Pattern, and Virus Serotype Correlate with Disease Sensitivity. J Infect Dis 181:2-9 (2000).
Verdijik et al. Limited amounts of DC migrate into the T-cell area of lymph nodes, but have high immune activating potential in melanoma patients. Clin Can Res 15(7):2531-2540 (2009).
Via et al. IL-12 stimulates the development of acute graft-versus-host disease in mice that normally would develop chronic, autoimmune graft-versus-host disease. J Immunol 153(9):4040-4047 (1994).
Wahid et al. A comparison of the pattern of liver involvement in Dengue Hemorrhagic Fever with classic Dengue Fever. Southeast Asian J Trop Med Public Health 31(2):259-263 (2000).
Wolchok et al. Guidelines for the evaluation of immune therapy activity in solid tumors: immune-related response criteria. Clin Cancer Res 15(23):7412-7420 (2009).
Wolchok et al. Nivolumab plus ipilimumab in advanced melanoma. N Eng J Med. 369:122-133(2013).
Wu et al. Human skin Langerhans cells are targets of dengue virus infection. Nature Medicine 6:816-820 (2000).
Xu et al. High-avidity antitumor T-cell generation by toll receptor 8-primed, myeloid- derived dendritic cells is mediated by IL-12 production. Surgery 140(2):170-178 (2006).
Yang et al. TGF-beta and immune cells: an important regulatory axis in the tumor microenvironment and progression. Trends Immunol 31(6):220-227 (2010).
Yeo et al. Lack of clinical manifestations in asymptomatic dengue infection is attributed to broad down-regulation and selective up-regulation of host defence response genes. PloS One 9(4):e92240 (2014).
Yu et al. New Immunotherapy Strategies in Breast Cancer. Int J Environ Res Public Health 14(1):pii:68 (2017).
Zellweger et al. Mouse models to study dengue virus immunology and pathogenesis. Front Imunol 10(5):151 (Apr. 2014).
Zitvogel et al. Therapy of murine tumors with tumor-peptide-pulsed dendritic cells: dependence on T cells, B7 costimulation, and T-helper cell-1 associated cytokines. J Exp Med 183:87-97 (1996).
Zobywalski et al. Generation of clinical grade dendritic cells with capacity to produce biologically active IL-12p70. J Transl Med 5:18 (2007).
Danhua Zhao et al.: "Live attenuated measles virus vaccine induces apoptosis and promotes tumor regression in lung cancer", Oncology Reports, 29:1, Oct. 29, 2012.
Sancho, D. et al., Tumor therapy in mice via antigen targeting to a novel, DC-restricted c-type lectin, J. Clin. Invest., 2008, vol. 118(6), pp. 2098-2110.
Fukuhara, Hiroshi et al., "Oncolytic virus therapy: A new era of cancer treatment at dawn". Cancer Science, vol. 107(10) Sep. 9, 2016, pp. 1373-1379.
Bergman, L. et al., "Uveal Melanoma: a Study on Incidence of Additional Cancers in the Swedish Population", Invest. Ophthalmol. Vis. Sci., 2006, vol. 47(1), pp. 72-77.
Bradford, P. T. et al., "Increased Risk of Second Primary Cancers After a Diagnosis of Melanoma", Arch. Dermatol., 2010, vol. 146(3), pp. 265-272.
Fischer et al., "Vaccine-induced CD8 T cells are redirected with peptide-MHC class I-IgG antibody fusion proteins to eliminate tumor cells in vivo", (2020) mAbs, 12:1, DOI: 10.1080/19420862.2020.1834818.
Goldufsky, J.W., et al., "Attenuated Dengue virus PV001-DV induces oncolytic tumor cell death and potent immune responses" J Transl Med. Jul. 19, 2023;21(1):483. doi: 10.1186/s12967-023-04344-8. PMID: 37468934.

(56) References Cited

OTHER PUBLICATIONS

Pandurengan, R. K. et al., Survival of Patients with Multiple Primarymalignancies: a Study of 783 Patients with Gastrointestinal Stromal Tumor, Ann. Oncol., 2010, vol. 21(10), pp. 2107-2111.
Ya et al., "Mouse Model for Pre-Clinical Study of Human Cancer Immunotherapy", Current protocols in immunology (2015), 108. 20.1.1-20.1.43. 10.1002/0471142735.im2001s108.

* cited by examiner

SEQUENCE LISTING

<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Gly Ser Arg Asn Gln Asp Trp Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 2

Thr Ala Tyr Arg Tyr His Leu Leu
1               5

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcccaag aagggccat                                                  20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcagctcca tagattgct                                                  19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtgttgctg cagatggaa                                                  19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgtcacaga cagtgaggt                                                  19

<210> SEQ ID NO 7
<211> LENGTH: 8
<212> TYPE: PRT
<213> ORGANISM: Gallus gallus

<400> SEQUENCE: 7

Ser Ile Ile Asn Phe Glu Lys Leu
1               5
```

METHOD FOR TREATING CANCER USING DENGUE VIRUS SEROTYPE 1 (DENV-1)

CROSS REFERENCE

This application is a continuation of U.S. patent application Ser. No. 16/460,629, filed on Jul. 2, 2019, which is continuation application of International Application No. PCT/US2018/012408, filed Jan. 4, 2018, which claims the benefit of U.S. Provisional Patent Application No. 62/442,199, filed Jan. 4, 2017; and U.S. Provisional Application No. 62/586,496, filed Nov. 15, 2017, each of which is herein incorporated by reference in its entirety.

SEQUENCE LISTING

The instant application contains a Sequence Listing which has been filed electronically in ASCII format and is hereby incorporated by reference in its entirety. Said ASCII copy, created on Dec. 21, 2020, is named 48253_706_302_SL.txt and is 1,866 bytes in size.

BACKGROUND

Immunotherapy, unlike cytotoxic drugs, radiation, and surgery, stimulates the immune system to recognize and kill tumor cells. Numerous attempts have been made in stimulating the immune system to recognize and destroy tumor cells. These have been met with limited success due to the self-identity of peptides selected as target for immunotherapy, lack of immune activation, adverse events, and/or tumor immune evasion mechanisms.

The ability of current cellular therapies, e.g., dendritic cell therapies, to induce durable, complete responses in advanced cancer patients is low (5-10% in the most immunogenic cancer types, lower in others). Often, dendritic cell therapies produce less than desirable results because of low activation (e.g., not enough immune cells to adequately kill all cancer cells), low targeting (e.g., healthy cells are killed and/or tumor cells are not killed), or an immunosuppressed tumor microenvironment, limiting drug efficacy. Thus there is a need for improved immunotherapies to treat cancer.

Tumors, by virtue of their high mitotic and cellular metabolic rates, are often oxygen deficient. This oxygen deficiency leads to higher utilization of anaerobic pathways to generate adenosine triphosphate (ATP), with the result of higher levels of lactate, and lower pH within the cytoplasm and nucleus. Thus there is a need for targeting and eradicating these low-perfusion tumor sites with high genetic plasticity.

BRIEF SUMMARY

Disclosed herein is a composition comprising an effective amount of Dengue Virus for treatment or reduction of cancer in a subject in need thereof; and at least one pharmaceutically acceptable excipient. Further provided herein are methods comprising an effective amount of Dengue virus wherein the effective amount is from about $10^2$ to about $10^8$ plaque-forming units (PFU)/mL. Further provided are methods comprising a Dengue virus wherein the Dengue virus is administered at about $10^5$ PFU/mL. Further provided herein are methods comprising an effective amount wherein the effective amount is from about 10,000 PFU/mL to 90,000 PFU/mL. Further provided herein are methods comprising an effective amount of Dengue virus wherein the effective amount is from about 30,000 PFU/mL. Further provided herein are methods comprising a composition wherein the composition is administered to a subject at least once. Further provided herein are methods wherein the cancer is from a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods wherein the cancer is from a melanoma. Further provided herein are methods wherein the melanoma is V600E positive. Further provided herein are methods wherein the cancer is from a refractory cancer. Further provided herein are methods comprising a Dengue virus wherein the Dengue virus is of serotype 1, 2, 3, 4, or 5. Further provided herein are methods comprising a Dengue virus wherein the Dengue virus is DENV-2 strain #1710. Further provided herein are methods that comprise compositions wherein the compositions further comprise a non-ionic surfactant. Further provided herein are methods comprising a non-ionic surfactant wherein the surfactant comprises pluronic F-68. Further provided herein are methods comprising a non-ionic surfactant wherein the surfactant is present in a composition at a concentration of about 1% w/v to about 5% w/v. Further provided herein are methods comprising a non-ionic surfactant wherein the surfactant is present in a composition at a concentration of about 2% w/v. Further provided herein are methods comprising a composition wherein the composition further comprises a non-reducing sugar. Further provided herein are methods comprising a non-reducing sugar wherein the sugar comprises alpha-trehalose. Further provided herein are methods comprising a non-reducing sugar wherein the sugar is present in a composition at a concentration of about 5% w/v to about 25% w/v. Further provided herein are methods comprising a non-reducing sugar wherein the sugar is present in a composition at a concentration of about 15% w/v. Further provided herein are methods comprising an excipient wherein the excipient comprises albumin. Further provided herein are methods comprising an excipient wherein the excipient is present in a composition at a concentration of about 1% w/v to about 5% w/v. Further provided herein are methods comprising an excipient wherein the excipient is present in a composition at a concentration of about 2% w/v. Further provided herein are methods comprising a composition wherein the composition comprises at least one salt. Further provided herein are methods comprising at least one salt wherein the salt comprises calcium chloride, magnesium chloride, or a combination thereof. Further provided herein are methods comprising at least one salt wherein the salt is present in a composition at a concentration of about 0.1 mM to about 10 mM. Further provided herein are methods comprising at least one salt wherein the salt is present in a composition at a concentration of about 1 mM. Further provided herein are methods comprising compositions wherein the compositions are in the form of an oral formulation, an intravenous formulation, an intranasal formulation, a subcutaneous formulation, an inhalable respiratory formulation, and any combination thereof. Further provided herein are methods comprising a Dengue virus wherein the Dengue virus is in liquid form, lyophilized form or freeze-dried form. Further provided herein are methods comprising a Dengue virus wherein the Dengue virus is in a volume of about 0.01 ml, 0.02 ml, 0.03 ml, 0.04 ml, 0.05 ml, 0.1 ml. Further provided herein are methods comprising a Dengue virus that is in a volume of about 0.01 mL to 0.01 mL. Further provided are methods comprising a Dengue virus wherein the Dengue virus is stored in a container. Further provided herein are methods comprising a container wherein the container is a syringe, vial, bottle, flask, or bag.

Disclosed herein is a composition comprising: an effective amount of Dengue Virus for treatment or reduction of metastatic cancer in a subject in need thereof; and at least one pharmaceutically acceptable excipient. Further provided are compositions comprising effective amount of Dengue virus wherein the effective amount is about $10^2$ to about $10^8$ plaque-forming units (PFU)/mL. Further provided herein is a Dengue virus wherein the Dengue virus is administered at about $10^5$ PFU/mL. Further provided is an effective amount wherein the effective amount is from about 10,000 PFU/mL to 90,000 PFU/mL. Further provided is an effective amount wherein the effective amount is about 30,000 PFU/mL. Further provided is a composition wherein the composition is administered to a subject at least once. Further provided are cancer cells wherein the cancer cells are from a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided are cancer cells wherein the cancer cells are from a melanoma. Further provided is a melanoma wherein the melanoma is V600E positive. Further provided are cancer cells wherein the cancer cells are from a refractory cancer. Further provided is a Dengue virus wherein the Dengue virus is of serotype 1, 2, 3, 4, or 5. Further provided is a Dengue virus wherein the Dengue virus is DENV-2 strain #1710. Further provided herein is a composition wherein the composition further comprises a non-ionic surfactant. Further provided herein is a non-ionic surfactant wherein the surfactant comprises pluronic F-68. Further provided is a non-ionic surfactant wherein the surfactant is in a composition at a concentration of about 1% w/v to about 5% w/v. Further provided herein is a non-ionic surfactant wherein the surfactant is present in a composition at a concentration of about 2% w/v. Further provided is a composition wherein the composition comprises a non-reducing sugar. Further provided herein is a composition wherein the non-reducing sugar comprises alpha-trehalose. Further provided herein is a composition wherein the non-reducing sugar is present at a concentration of about 5% w/v to about 25% w/v. Further provided herein is a non-reducing sugar wherein the sugar is present in a composition at a concentration of about 15% w/v. Further provided is an excipient wherein the excipient comprises albumin. Further provided is an excipient wherein the excipient is present in a composition at a concentration of about 1% w/v to about 5% w/v. Further provided is an excipient wherein the excipient is present in a composition at a concentration of about 2% w/v. Further provided is a composition wherein the composition further comprises at least one salt. Further provided is at least one salt wherein the salt comprises calcium chloride, magnesium chloride, or a combination thereof. Further provided is at least one salt wherein the salt is present in a composition at a concentration of about 0.1 mM to about 10 mM. Further provided herein is at least one salt wherein the salt is present in a composition at a concentration of about 1 mM. Further provided herein is a composition wherein the composition in the form of an oral formulation, an intravenous formulation, an intranasal formulation, a subcutaneous formulation, an inhalable respiratory formulation, and any combination thereof. Further provided is a Dengue virus wherein the Dengue virus in liquid form, lyophilized form or freeze-dried form. Further provided are compositions comprising a Dengue virus wherein the Dengue virus is in a volume of about 0.01 ml, 0.02 ml, 0.03 ml, 0.04 ml, 0.05 ml, 0.1 mL. Further provided herein are compositions comprising Dengue virus that is in a volume of about 0.01 mL to 0.01 mL. Further provided herein are compositions comprising Dengue virus wherein the Dengue virus is stored in a container. Further provided are compositions comprising a container wherein the container is a syringe, vial, bottle, flask, or bag. Further provided are compositions comprising Dengue virus that is 45AZ5, 1710, S16803, HON 1991 C, HON 1991 D, HON 1991 B, HON 1991 A, SAL 1987, TRI 1981, PR 1969, IND 1957, TRI 1953, TSV01, D509-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750.

Provided herein are methods of treating or reducing cancer in a subject in need thereof, comprising administering to a subject an effective amount of Dengue virus to treat or reduce a cancer in the subject. Further provided herein are methods wherein the Dengue virus is present in an amount of about $10^2$ to about $10^8$ plaque-forming units (PFU)/mL. Further provided herein are methods wherein the Dengue virus is present in an amount of Dengue virus can be administered at about $10^5$ PFU/mL. Further provided herein are methods wherein the Dengue virus is present in an amount of from about 10,000 PFU/mL to 90,000 PFU/mL. Further provided herein are methods wherein the amount of a Dengue virus can be about 30,000 PFU/mL. Further provided herein are methods comprising a second administration of a Dengue virus to a subject in need thereof. Further provided herein are methods wherein the cancer is a solid cancer or a hematopoietic cancer. Further provided herein are methods wherein the solid cancer is a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods wherein the solid cancer is a melanoma. Further provided herein are methods wherein the melanoma is V600E positive. Further provided herein are methods wherein the cancer is refractory cancer. Further provided herein are methods wherein the Dengue virus is of serotype 1, 2, 3, 4, or 5. Further provided herein are methods wherein the Dengue virus is DENV-2 strain #1710. Further provided herein are methods wherein the methods reduce a cancer in size by at least about 60% as measured by computed tomography (CT) scan. Further provided herein are methods wherein the methods reduce a cancer in size by at least about 80% as measured by computed tomography (CT) scan. Further provided herein are methods wherein the methods reduce a cancer in size by at least about 90% as measured by computed tomography (CT) scan. Further provided herein are methods comprising a Dengue virus that is in a volume of about 0.01 ml, 0.02 ml, 0.03 ml, 0.04 ml, 0.05 ml, or 0.1 mL. Further provided herein are methods comprising a Dengue virus that is in a volume of about 0.01 mL to 0.01 mL. Further provided herein are methods comprising administering a Dengue virus wherein the administering comprises a subcutaneous injection to a subject. Further provided herein are methods comprising a Dengue virus in liquid form, lyophilized form or freeze-dried form. Further provided herein are methods comprising a Dengue virus that is stored in a container. Further provided herein are methods comprising a container that can be a syringe, vial, bottle, flask, or bag. Further provided is a Dengue virus strain that is 45AZ5, 1710, S16803, HON 1991 C, HON 1991 D, HON 1991 B, HON 1991 A, SAL 1987, TRI 1981, PR 1969, IND 1957, TRI 1953, TSV01, DS09-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750.

Provided herein is a method of treating a metastatic cancer in a subject wherein the method comprises administering to a subject in need thereof an effective amount of Dengue virus, wherein the administering reduces a level of cancer cells in the subject in need thereof. Further provided herein are methods comprising an effective amount of Dengue virus that is about $10^2$ to about $10^8$ plaque-forming units (PFU)/mL. Further provided herein are methods comprising a Dengue virus wherein the Dengue virus is administered at about $10^5$ PFU/mL. Further provided herein are methods comprising an effective amount of a Dengue virus wherein the effective amount is from about 10,000 PFU/mL to 90,000 PFU/mL. Further provided herein are methods comprising an effective amount of a Dengue virus wherein the effective amount is about 30,000 PFU/mL. Further provided herein are methods that further comprise a second administering of a Dengue virus to a subject in need thereof. Further provided herein are methods comprising a metastatic cancer wherein the metastatic cancer is from a solid cancer or a hematopoietic cancer. Further provided herein are methods comprising a solid cancer wherein the solid cancer is a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods wherein the solid cancer is melanoma. Further provided are methods wherein the melanoma is V600E positive. Further provided herein are methods wherein the metastatic cancer is a refractory cancer. Further provided herein are methods wherein the Dengue virus is of serotype 1, 2, 3, 4, or 5. Further provided herein are methods wherein the Dengue virus is DENV-2 strain #1710. Further provided herein are methods that reduce a cancer in size by at least about 60% as measured by computed tomography (CT) scan. Further provided herein are methods wherein the methods reduce a cancer in size by at least about 80% as measured by computed tomography (CT) scan. Further provided herein are methods wherein the methods reduce a cancer in size by at least about 90% as measured by computed tomography (CT) scan. Further provided herein are methods wherein the methods comprise administering primed dendritic cells to a subject, wherein the primed dendritic cells produce more than about 6.5 ng/mL IL-12p70. Further provided herein are methods that further comprise administering primed dendritic cells to a subject, wherein the primed dendritic cells produce at least about 15 ng/mL IL-12p70. Further provided herein are dendritic cells wherein the dendritic cells are autologous or allogeneic to a subject in need thereof. Further provided herein are methods comprising dendritic cells wherein the dendritic cells are allogeneic cells that are HLA matched to a subject in need thereof. Further provided herein are methods comprising a Dengue virus wherein in a volume of about 0.01 ml, 0.02 ml, 0.03 ml, 0.04 ml, 0.05 ml, or 0.1 mL. Further provided herein are methods comprising a Dengue virus that is in a volume of about 0.01 mL to 0.01 mL. Further provided herein are methods of administration of a Dengue virus wherein the administration comprises a subcutaneous injection to a subject. Further provided herein are methods comprising Dengue virus in liquid form, lyophilized form or freeze-dried form. Further provided herein are methods comprising a Dengue virus wherein the Dengue virus is stored in a container. Further provided herein are methods comprising a container wherein the container is a syringe, vial, bottle, flask, or bag. Further provided herein are methods comprising a Dengue virus strain that is 45AZ5, 1710, S16803, HON 1991 C, HON 1991 D, HON 1991 B, HON 1991 A, SAL 1987, TRI 1981, PR 1969, IND 1957, TRI 1953, TSV01, DS09-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750.

Disclosed herein is a method of clearing cancer cells, comprising administering an effective amount of a Dengue virus, wherein the administering provides for clearance of the cancer cells. Further provided herein are methods comprising an effective amount of Dengue virus wherein the effective amount is about $10^2$ to about $10^8$ plaque-forming units (PFU)/mL. Further provided herein are methods comprising a Dengue virus wherein the Dengue virus is administered at about $10^5$ PFU/mL. Further provided herein are methods comprising an effective amount of a Dengue virus that is from about 10,000 PFU/mL to 90,000 PFU/mL. Further provided herein are methods comprising an effective amount of a Dengue virus wherein the effective amount is from about 30,000 PFU/mL. Further provided herein are methods further comprising a second administering of a Dengue virus to a subject in need thereof. Further provided herein are methods comprising cancer cells wherein the cancer cells are from a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods comprising cancer cells wherein the cancer cells are from a melanoma. Further provided herein are methods comprising melanoma that is V600E positive. Further provided herein are methods comprising cancer cells from a refractory cancer. Further provided herein are methods comprising Dengue virus of serotype 1, 2, 3, 4, or 5. Further provided herein are methods comprising a Dengue virus that is DENV-2 strain #1710. Further provided herein are methods comprising a Dengue virus in a volume of about 0.01 ml, 0.02 ml, 0.03 ml, 0.04 ml, 0.05 ml, or 0.1 mL. Further provided herein are methods comprising a Dengue virus that is in a volume of about 0.01 mL to 0.01 mL. Further provided herein are methods comprising administering wherein the administering is of a Dengue virus that comprises a subcutaneous injection to a subject. Further provided herein are methods comprising a Dengue virus wherein the Dengue virus is in liquid form, lyophilized form or freeze-dried form. Further provided herein are methods comprising a Dengue virus wherein the Dengue virus is in a container. Further provided herein are methods comprising a container wherein the container is a syringe, vial, bottle, flask, or bag. Further provided is a Dengue virus strain that is 45AZ5, 1710, S16803, HON 1991 C, HON 1991 D, HON 1991 B, HON 1991 A, SAL 1987, TRI 1981, PR 1969, IND 1957, TRI 1953, TSV01, D509-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750.

Provided herein are methods of treating a cancer in a subject, comprising administering to a subject in need thereof an effective amount of Dengue virus to reduce cancer cells. Further provided herein are methods, comprising administering DV at a magnitude of about $10^5$ plaque-forming units (PFU). Further provided herein are methods, wherein the effective amount is about 10,000 PFU to 90,000 PFU. Further provided herein are methods, wherein the effective amount is about 30,000 PFU. Further provided herein are methods, comprising administering multiple doses of the DV to the subject. Further provided herein are methods, wherein the cancer is a solid cancer or a hematopoietic cancer. Further provided herein are methods, wherein the solid cancer is a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods, wherein the solid cancer is a melanoma. Further provided herein are methods, wherein the cancer is a refractory cancer. Further provided herein are methods, wherein the Dengue virus is a Dengue virus serotype 1, 2, 3, 4, or 5. Further provided herein are methods, wherein the Dengue virus is DENV-2 strain #1710. Further provided herein are methods, wherein the Dengue virus reduces the cancer cells by at least about 60%. Further provided herein are methods, wherein the Dengue virus reduces the cancer cells by at least about 80%. Further provided herein are methods, wherein the Dengue virus reduces the cancer cells by at least about 90%. Further provided herein are methods, comprising administering primed dendritic cells to the subject, wherein the primed dendritic cells produce more than about 6.5 ng/mL IL-12p70. Further provided herein are methods, comprising administering primed dendritic cells to the subject, wherein the primed dendritic cells produce at least about 29 ng/mL IL-12p70. Further provided herein are methods, wherein the dendritic cells are autologous or allogeneic to the subject. Further provided herein are methods, wherein the dendritic cells are allogeneic cells that are HLA matched to the subject.

Provided herein are methods of treating a metastatic cancer in a subject, comprising administering to a subject in need thereof an effective amount of Dengue virus to reduce metastatic cancer cells. Further provided herein are methods, wherein the method comprises administering DV at a magnitude of about $10^5$ plaque-forming units (PFU). Further provided herein are methods, wherein the effective amount is about 10,000 PFU to 90,000 PFU. Further provided herein are methods, wherein the effective amount is about 30,000 PFU. Further provided herein are methods, comprising administering multiple doses of the DV to the subject. Further provided herein are methods, wherein the metastatic cancer cells are derived from a solid cancer or a hematopoietic cancer. Further provided herein are methods, wherein the solid cancer is a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods, wherein the solid cancer is a melanoma. Further provided herein are methods, wherein the metastatic cancer is a refractory cancer. Further provided herein are methods, wherein the Dengue virus is a Dengue virus serotype 1, 2, 3, 4, or 5. Further provided herein are methods, wherein the dengue virus is DENV-2 strain #1710. Further provided herein are methods, wherein the dengue virus reduces the metastatic cancer cells by at least about 60%. Further provided herein are methods, wherein the dengue virus reduces the metastatic cancer cells by at least about 80%. Further provided herein are methods, wherein the dengue virus reduces the metastatic cancer cells by at least about 90%. Further provided herein are methods, comprising administering primed dendritic cells to the subject, wherein the primed dendritic cells produce more than about 6.5 ng/mL IL-12p70. Further provided herein are methods, comprising administering primed dendritic cells to the subject, wherein the primed dendritic cells produce at least about 29 ng/mL IL-12p70 in vitro. Further provided herein are methods, wherein the dendritic cells are autologous or allogeneic to the subject. Further provided herein are methods, wherein the dendritic cells are allogeneic cells that are HLA matched to the subject.

Provided herein are methods of clearing cancer cells, comprising administering an effective amount of a dengue virus, wherein administration provides for clearance of the cancer cells. Further provided herein are methods, wherein the method comprises administering DV at a magnitude of about $10^5$ plaque-forming units (PFU). Further provided herein are methods, wherein the effective amount is about 10,000 to 90,000 PFU. Further provided herein are methods, wherein the effective amount is about 30,000 PFU. Further provided herein are methods, comprising administering multiple doses of the DV to the subject. Further provided herein are methods, wherein the cancer cells are from a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are methods, wherein the cancer cells are from a melanoma. Further provided herein are methods, wherein the cancer cells are from a refractory cancer. Further provided herein are methods, wherein the Dengue virus is a Dengue virus serotype 1, 2, 3, 4, or 5. Further provided herein are methods, wherein the Dengue virus is DENV-2 strain #1710. Further provided herein are methods, wherein the Dengue virus reduces the cancer cells by at least about 60%. Further provided herein are methods, wherein the Dengue virus reduces the cancer cells by at least about 80%. Further provided herein are methods, wherein the Dengue virus reduces the cancer cells by at least about 90%. Further provided herein are methods, comprising administering primed dendritic cells to the subject, wherein the primed dendritic cells produce more than about 6.5 ng/mL IL-12p70. Further provided herein are methods, comprising administering primed dendritic cells to the subject, wherein the primed dendritic cells produce at least about 29 ng/mL IL-12p70 in vitro. Further provided herein are methods, wherein the dendritic cells are autologous or allogeneic to the subject. Further provided herein are methods, wherein the dendritic cells are allogeneic cells that are HLA matched to the subject.

Provided herein are compositions comprising an effective amount of Dengue Virus to reduce cancer cells in a subject and a pharmaceutically acceptable carrier. Further provided herein are compositions, wherein the effective amount is about 10,000PFU to 90,000 PFU. Further provided herein are compositions, wherein the effective amount is about 30,000 PFU. Further provided herein are compositions, wherein the cancer cells are from a bladder cancer, a brain cancer, a breast cancer, a cervical cancer, a gastrointestinal cancer, a kidney cancer, a liver cancer, a lung cancer, an ovarian cancer, a pancreatic cancer, prostate cancer, a sarcoma, a skin cancer, or a uterine cancer. Further provided herein are compositions, wherein the cancer cells are from a melanoma. Further provided herein are compositions, wherein the cancer cells are from a refractory cancer. Further provided herein are compositions, wherein the Dengue virus is a Dengue virus serotype 1, 2, 3, 4, or 5. Further provided herein are compositions, wherein the Dengue virus is DENV-2 strain #1710. Further provided is a Dengue virus that is 45AZ5, 1710, S16803, HON 1991 C, HON 1991 D, HON 1991 B, HON 1991 A, SAL 1987, TRI 1981, PR 1969, IND 1957, TRI 1953, TSV01, DS09-280106, DS31-291005, 1349, GD01/03, 44, 43, China 04, FJ11/99, FJ-10, QHD13CAIQ, CO/BID-V3358, FJ/UH21/1971, GU/BID-V2950, American Asian, GWL18, IN/BID-V2961, Od2112, RR44, 1392, 1016DN, 1017DN, 1070DN, 98900663DHF, BA05i, 1022DN, NGC, Pak-L-2011, Pak-K-2009, Pak-M-2011, PakL-2013, Pak-L-2011, Pak-L-2010, Pak-L-2008, PE/NFI1159, PE/IQA 2080, SG/D2Y98P-PP1, SG/05K3295DK1, LK/BID/V2421, LK/BID-V2422, LK/BID-V2416, 1222-DF-06, TW/BID-V5056, TH/BID-V3357, US/BID-V5412, US/BID-V5055, IQT1797, VN/BID-V735, US/Hawaii/1944, CH53489, or 341750.

DETAILED DESCRIPTION

Definitions

Figure 1A:
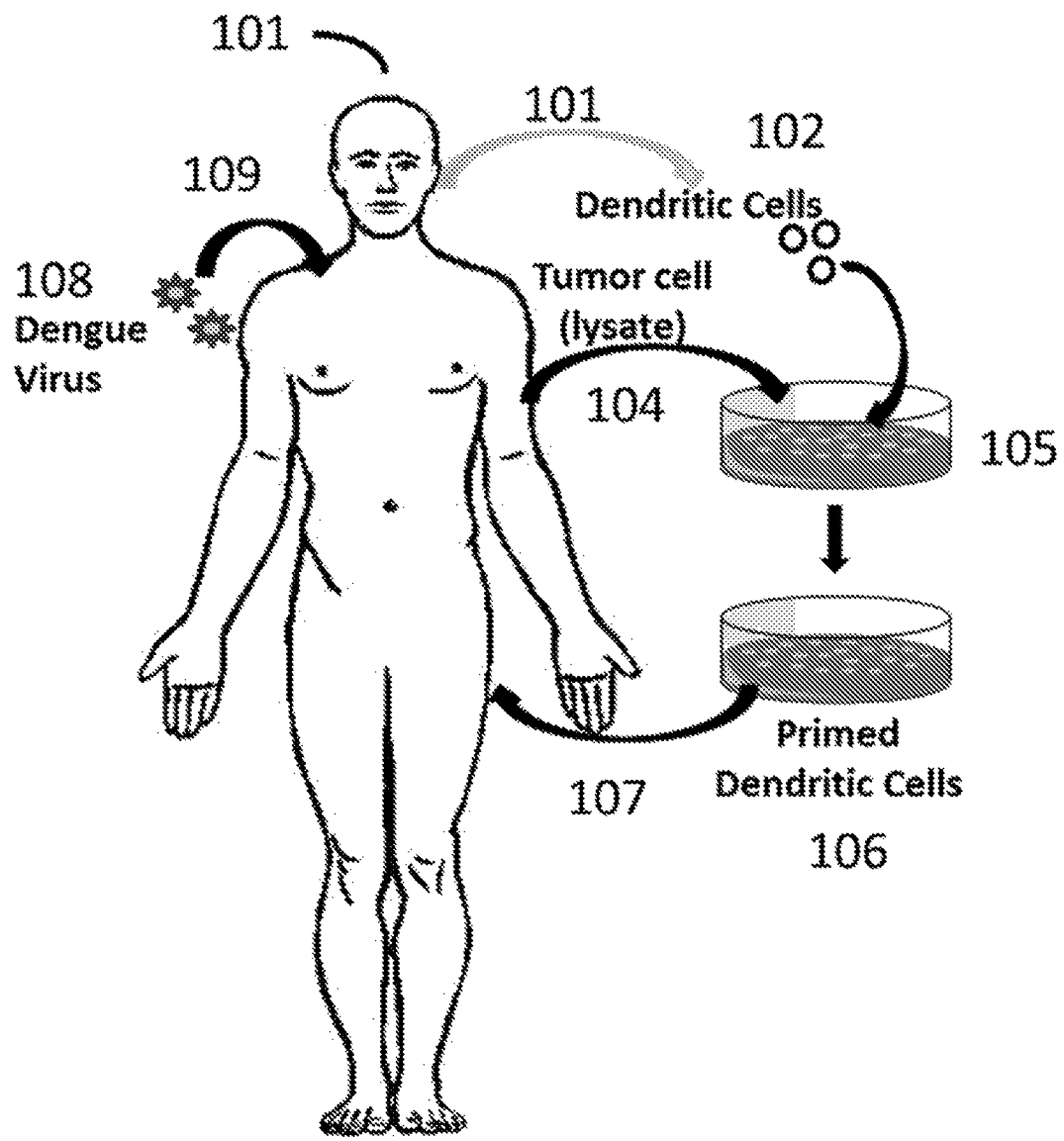
FIG. 1A depicts an exemplary method of treatment with Dengue virus and dendritic cells.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The term "subject" as used herein includes to mammals. Mammals include rats, mice, non-human primates, and primates, including humans.

Dengue Virus Therapy

Provided herein are compositions and methods where Dengue virus is present in an effective amount for the treatment or reduction of a cancer in a subject in need thereof. Use of Dengue virus as described herein includes the therapeutic administration of Dengue virus to treat various conditions, such as cancer, in a subject. Further provided can be compositions, methods, and use of Dengue virus for the treatment, stabilization, or reduction of cancer. Further provided herein are methods of treating cancer by administering to a subject an effective amount of Dengue virus wherein the Dengue virus is able to treat, stabilize, or reduce a cancer in the treated subject as compared to an untreated subject. Further provided is a composition comprising a Dengue virus that can also be used as an adjuvant to activate synergistic pathways that may support the eradication or stabilization of mutated cancer cells thereby improving the clinical efficacy of a Dengue virus therapy.

In some cases, Dengue virus therapy can be utilized as a combination therapy. Dengue virus therapy can be utilized in conjunction with various anti-cancer therapies such as those combining physiological (hyperthermic reduction of tumor perfusion), immunological (activation of effector cells of the adaptive and innate immune system), and apoptosis-inducing pathways (sTRAIL) to destroy or stabilize the growth of tumor cells.

Dengue virus is unique among viruses as primary infections carry lower mortality than the common cold while also allowing for increased capillary permeability, and cytokine production, among other features. Provided herein are methods of treating a cancer in a subject, comprising administering to a subject in need thereof an effective amount of Dengue virus disclosed herein. Also provided herein are methods of treating a metastatic cancer in a subject, comprising administering to a subject in need thereof an effective amount of dengue virus. Further provided herein are methods of clearing cancer cells, comprising administering an effective amount of a dengue virus, wherein administering provides for clearance of the cancer cells.

Provided herein are compositions and methods for reducing the cancer cells in a subject in need thereof comprising administering a Dengue virus, wherein the method provides for reduction of cancer cells in the subject by at least about 40%. In some instances, the methods and compositions disclosed herein provide for reduction of cancer cells in the subject by at least about 40%, about 45%, about 50%, about 55%, about 60%, about 65%, about 70%, about 75%, about 80%, about 85%, about 90%, about 95%, or about 100%.

Provided herein are methods and composition for combination therapy, comprising administering to a subject in need thereof: a Dengue virus (DV) and Dendritic Cells (DCs) primed to target tumor cells. As used herein, the term "Dengue virus" includes any serotype of Dengue virus serotypes 1, 2, 3, 4, or 5.

Dengue Viruses

Figure 1B:
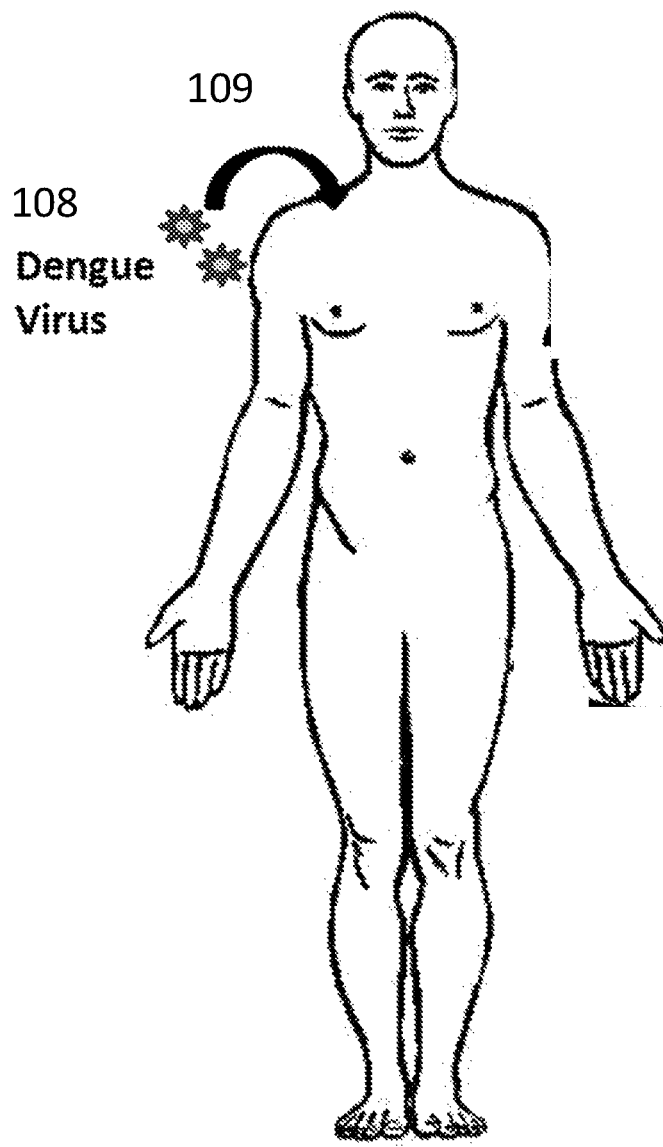
FIG. 1B depicts an exemplary method of treatment with Dengue virus.

Provided herein are compositions for the treatment of cancer, wherein the composition comprises a Dengue virus in an effective amount for depletion or reduction of cancer in a subject in need thereof (FIG. 1B.) Also provided herein are methods for treatment of cancer, comprising administering to a subject in need thereof, an effective amount of a Dengue virus for depletion or reduction of a cancer. Also provided herein are methods for the stabilization of cancer, comprising administering to a subject in need thereof, an effective amount of a Dengue virus for stabilizing or controlling growth of a cancer. Dengue viruses are Arboviruses, and are transmitted exclusively by mosquitoes of the *Aedes aegypti* and *albopictus* species. The virus has a complex life cycle involving an unidentified forest-dwelling mammalian reservoir (possibly primates), and human hosts. The female mosquito takes a blood meal from an infected person, the virus replicates to a high infectious titer ($10^5$/ml) in gut epithelial cells, then is transmitted to another person when the mosquito withdraws its stylet using back pressure after another blood meal. Dengue epidemics infect 50 million persons annually, with several thousand deaths, usually children with inadequate treatment of secondary infection-related shock.

The Dengue virus genome encodes structural proteins, capsid protein C, membrane protein M, envelope protein E, and nonstructural proteins, NS1, NS2a, NS2b, NS3, NS4a, NS4b and NS5. In some instances, the Dengue virus is a live strain of the Dengue virus. In some instances, the Dengue virus is an attenuated strain of the Dengue virus. In some instances, the Dengue virus is a weakened strain of the Dengue virus. In some instances, the Dengue virus is selected from the following serotypes of dengue virus: DENV-1, DENV-2, DENV-3, DENV-4, and DENV-5, and combinations thereof.

Dengue Viruses are positive-strand RNA viruses of the Togavirus Family, sub-family Flaviviridae, (Group B). The virus has an icosahedral geometry and is approximately 40-45 nanometers in diameter. The 11,000 base genome codes for a nucleocapsid (NC) protein, a prM membrane fusion protein, an envelope glycoprotein (E), and 5 non-structural proteins NS1-NS5. The NC protein forms the viral core, with the envelope spikes attached via the prM complex. The E glycoprotein is the main target of neutralizing antibodies, and the NS-3 and NS-4 proteins make up the main targets for CD4+ and CD8+ CTL.

The Dengue viruses make up five distinct serotypes, DENV-1 through DENV-5. The serotypes 2 and 4 are cross-neutralizing for IgG, and types 1 and 3 are also cross-neutralizing. Immunity is not complete, however, and Dengue is unique among viral infections in that a subsequent infection by a non-cross-neutralizing serotype carries an increased risk of mortality due to shock syndrome from immune hyper-activation. In some cases, a non-lethal form of a Dengue virus can be utilized. Exemplary non-lethal Dengue viruses can be of serotype 1, 2, 3, 4, or 5. For example, a non-lethal Dengue virus can be selected from Table 1. For example a Dengue Virus can be from about 50%, 60%, 70%, 80%, 90%, 95%, 96%, 97%, 98%, 99%, or up to about 100% identical in sequence homology or structural homology to any strain of Table 1.

TABLE 1

Non-lethal Dengue Virus Strains

| Serotype | Strain |
|---|---|
| I | 45AZ5 |
| II | 1710 |
| II | S16803 |
| II | HON 1991 C |
| II | HON 1991 D |
| II | HON 1991 B |
| II | HON 1991 A |
| II | SAL 1987 |
| II | TRI 1981 |
| II | PR 1969 |
| II | IND 1957 |
| II | TRI 1953 |
| II | TSV01 |
| II | DS09-280106 |
| II | DS31-291005 |
| II | 1349 |
| II | GD01/03 |
| II | 44 |
| II | 43 |
| II | China 04 |
| II | FJ11/99 |
| II | FJ-10 |
| II | QHD13CAIQ |
| II | CO/BID-V3358 |
| II | FJ/UH21/1971 |
| II | GU/BID-V2950 |
| II | American Asian |
| II | GWL18 |
| II | IN/BID-V2961 |
| II | Od2112 |
| II | RR44 |
| II | 1392 |

TABLE 1-continued

Non-lethal Dengue Virus Strains

| Serotype | Strain |
|---|---|
| II | 1016DN |
| II | 1017DN |
| II | 1070DN |
| II | 98900663DHF |
| II | BA05i |
| II | 1022DN |
| II | NGC |
| II | Pak-L-2011 |
| II | Pak-K-2009 |
| II | Pak-M-2011 |
| II | PakL-2013 |
| II | Pak-L-2011 |
| II | Pak-L-2010 |
| II | Pak-L-2008 |
| II | PE/NFI1159 |
| II | PE/IQA 2080 |
| II | SG/D2Y98P-PP1 |
| II | SG/05K3295DK1 |
| II | LK/BID/V2421 |
| II | LK/BID-V2422 |
| II | LK/BID-V2416 |
| II | 1222-DF-06 |
| II | TW/BID-V5056 |
| II | TH/BID-V3357 |
| II | US/BID-V5412 |
| II | US/BID-V5055 |
| II | IQT1797 |
| II | VN/BID-V735 |
| II | US/Hawaii/1944 |
| III | CH53489 |
| IV | 341750 |

Provided herein are compositions and methods using Dengue viruses, wherein the composition comprises Dengue virus serotype 1, 2, 3, 4, or 5. In some instances, the DV is serotype 2. In some instances the DV serotype 2 is DENV-2 strain #1710. DENV-2 strain #1710 is from a sample taken from Puerto Rico in 1985 and characterized as type A from a restriction site specific RT-PCR analysis using 4 primers (see Table 2) specific to the envelope gene region. See Harris et al., Virology 253, 86-95 (1999). Restriction site specific RT-PCR with these primers produces amplification products of 582 base pairs, 754 base pairs, and possibly 676 base pairs. The DENV-2 strain #1710 is recorded in a CDC database as entry number 555. See Harris (1999). The DENV-2 strain #1710 was isolated during a Puerto Rican epidemic. This outbreak had 9,540 suspected cases of DV, with one suspected, but no confirmed deaths due to the virus, which indicates the toxicity of DENV-2 strain #1710 is very low and therefore suitable for the methods disclosed herein.

TABLE 2

Sequence and Position of Primers to Amplify DENV-2 viruses

| Primer | Sequence | Genome Position | Strand |
|---|---|---|---|
| RSS1 | 5'-GGATCCCAAGAAGGGGCCAT-3' (SEQ ID NO: 3) | 1696-1715 | + |
| RSS2 | 5'-GGCAGCTCCATAGATTGCT-3' (SEQ ID NO: 4) | 2277-2259 | − |
| RSS3 | 5'-GGTGTTGCTGCAGATGGAA-3' (SEQ ID NO: 5) | 1524-1542 | + |
| RSS4 | 5'-GTGTCACAGACAGTGAGGT-3' (SEQ ID NO: 6) | 2371-2353 | − |

Advantageous DV characteristics for use as a potent immune-stimulant in cancer immunotherapies are described herein. DV has affinity for immature B-lymphocytes and antigen-presenting cells (APC) of monocyte/macrophage and dendritic cell (DC) lineage. A unique feature of DV is that primary infections result in activation of a $T_H1$-type response of CD4+ and CD8+ helper-inducer and cytotoxic-effector CTL. By infecting, but not killing the APC, DV up-regulates their CD80 and CD83 expression, resulting in a pro-inflammatory $T_H1$ cytokine profile. Primary DV infections induce a $T_H1$ type response with activated $CD4^+$ and $CD8^+$ effector T cells as well as LAK cells. This type of response is seen in patients having complete responses to cancer immunotherapies (see Table 3).

TABLE 3

Tumor immune evasion mechanisms and DV infection

| Immune evasion | Dengue counter-attack |
|---|---|
| Low levels of MHC on tumor cell prevent CTL recognition | High Interferon-γ raises MHC levels by up-regulating MHC gene expression |
| Point mutations in Tumor Peptides prevent TCR binding | LAK/CIK cells target "escaped" tumor cells expressing aberrant peptides or MHC |
| Tumor vessels lack factors for CTL attachment and trafficking | Hi [TNF-α] restores gaps by altering PECAM-1, restores ICAM-1/VCAM-1 expression and P and E-selectins |
| FasL can kill $Fas^+$ CTL by triggering apoptosis | Hi [IL-6, 15] protects $Fas^+$ CTL by up-regulating FLIP ligand |
| HLA-G protects from NK Cells | Hi [IL-2,7,12,15] raise activation of NK |
| Stromal barriers inhibit CTL | Hi [IFN-γ] activates Macrophages to $M_1$ |
| Myeloid-Derived Suppressor Cells, (MDSC) | iNKT Cells can decrease MDSC |
| CTL inactivated by TGF-β | $T_H1$ cytokines reactivate tolerant CTL |
| Tumor PI-9 blocks CTL killing | Hi [CD8] & ICAM-1 expression can restore low-avidity CTL recognition and lysis by stabilizing weak interactions between TCR and MHC + self-peptide |
| T-regulatory cells block CTL | Hi $CD4^{Helper}$ cells overcome $CD4^{Reg}$ cells |

In primary infections, the death rate from DV is very low (1 in 61,000 per Manson's Tropical Diseases). The virus infects but does not kill APC of the monocyte-macrophage and Dendritic Cell lineage. These infected APC then begin a cytokine cascade of the pro-inflammatory (TNF-alpha and IL-1 beta), and $T_H1$ (IL-2, IL-7, IL-12, IL-15, and IL-21) types. These cytokines result in strong activation of both the adaptive (CTL) and innate (NK) immune systems. After a 3-5 day incubation period, the fever rises to 39.5-40.5° C., and remains elevated for 4-5 days. The patient experiences intense headache, joint pain, malaise, and sensitivity to light. A rash covering the chest back and sometimes legs and arms develops by day 3 of fever. Clinically, dengue infections result in lowered platelet counts leading to hemorrhage, which ranges from minor to life-threatening in case of shock syndrome. With proper supportive care based on judicious fluid management, recovery is complete in 99% of cases.

Pharmaceutical Compositions

Provided herein are compositions comprising an effective amount of Dengue virus (DV) to reduce cancer cells in a subject in need thereof. In some instances, the effective amount is about 10^5 plaque-forming units (PFU). In some instances, the effective amount of DV is about 10,000 to about 90,000 PFU; about 20,000 to about 60,000 PFU; about 50,000 to about 80,000 PFU. In some instances, the effective amount of DV is greater than about 40,000 PFU or greater than about 30,000 PFU. In some instances, the effective amount of DV is less than about 90,000 PFU; less than about 30,000 PFU; or less than about 20,000 PFU.

Provided herein are compositions comprising an effective amount of Dengue virus sufficient to increase a level of at least one cytokine in the subject. In some instances, the effective amount is an amount sufficient to increase a level of at least one cytokine in the blood of the subject. In some instances, the effective amount is an amount sufficient to increase a level of at least one cytokine in a serum sample of the subject. In some instances, the effective amount is an amount sufficient to significantly increase the level of the at least one cytokine. In some instances, the effective amount is an amount sufficient to increase the level of the at least one cytokine by about 2% to about 20,000%. In some instances, the effective amount is an amount sufficient to increase the level of the at least one cytokine by about 50% to about 20,000%. In some instances, the effective amount is an amount sufficient to increase the level of the at least one cytokine by about 100% to about 20,000%. In some instances, the effective amount is an amount sufficient to increase the level of the at least one cytokine by about 100% to about 15,000%. In some instances, the effective amount is an amount sufficient to increase the level of the at least one cytokine by about 100% to about 14,000%. In some instances, the effective amount is an amount sufficient to increase the level of the at least one cytokine by about 50% to about 15,000%. In some instances, the effective amount is an amount sufficient to increase the level of the at least one cytokine by about 50% to about 14,000%.

Provided herein are compositions comprising an amount of Dengue virus sufficient to increase a level of at least one cytokine in the subject. In some instances, the at least one cytokine is an interleukin (IL). In some instances, the at least one cytokine is an interferon (IFN). In some instances, the at least one cytokine is an interleukin. In some instances, the at least one cytokine is selected from tumor necrosis factor (TNF) alpha, IFN alpha, IFN beta, IFN gamma, interferon gamma induced protein 10 (IP-10), IL-12, IL-2R, IL-7, IL-15, granulocyte macrophage colony stimulating factor (GM-CSF), and a combination thereof. In some instances the level of TNF alpha is increased from about 50% to about 500%. In some instances the level of TNF alpha is increased from about 50% to about 300%. In some instances the level of TNF alpha is increased from about 50% to about 240%. In some instances the level of IFN alpha is increased from about 50% to about 800%. In some instances the level of IFN alpha is increased from about 50% to about 500%. In some instances the level of IFN alpha is increased from about 50% to about 420%. In some instances the level of IFN beta is increased from about 50% to about 20,000%. In some instances the level of IFN beta is increased from about 50% to about 14,000%. In some instances the level of IFN gamma is increased from about 50% to about 200%. In some instances the level of IFN gamma is increased from about 50% to about 100%. In some instances the level of IP-10 is increased from about 50% to about 8000%. In some instances the level of IP-10 is increased from about 50% to about 5000%. In some instances the level of IP-10 is increased from about 50% to about 4000%. In some instances the level of IL-12 is increased from about 20% to about 200%. In some instances the level of IL-12 is increased from about 20% to about 100%. In some instances the level of IL-12 is increased from about 20% to about 80%. In some instances the level of IL-15 is increased from about 20% to about 200%. In some instances the level of IL-15 is increased from about 20% to about 200%. In some instances the level of IL-15 is increased from about 20% to about 100%. In some instances the level of IL-7 is increased from about 50% to about 1000%. In some instances the level of IL-7 is increased from about 50% to about 1000%. In some instances the level of IL-7 is increased from about 50% to about 500%. In some instances the level of GM-CSF is increased from about 50% to about 1000%. In some instances the level of GM-CSF is increased from about 50% to about 400%. In some instances the level of GM-CSF is increased from about 50% to about 350%. In some instances the level of IL-12R is increased from about 20% to about 200%. In some instances the level of IL-12R is increased from about 20% to about 150%.

Provided herein are compositions comprising an effective amount of Dengue virus (DV), wherein the effective amount is an amount sufficient to increase expression of a protein in tumor cell. In some instances, the effective amount is an amount sufficient to increase expression of a protein expressed on a tumor cell. In some instances, the protein is a checkpoint protein. In some instances, this makes the tumor cell a better target for checkpoint inhibitors. In some instances, the checkpoint protein is programmed death-ligand 1 (PD-L1). In some instances, the effective amount increases the expression of PD-L1 by about 10% to about 100%. In some instances, the effective amount increases the expression of PD-L1 by about 10% to about 20%. In some instances, the effective amount is an amount sufficient to increase expression of a complex of proteins expressed on a tumor cell. In some instances, the complex is a major histocompatibility complex (MHC). In some instances, the MHC is a Class I MHC. In some instances, the effective amount increases the expression of the MHC by about 10% to about 60%. In some instances, the effective amount increases the expression of the MHC by about 10% to about 100%. In some instances, the effective amount increases the expression of the MHC by about 10% to about 150%.

Provided herein are compositions comprising an effective amount of Dengue virus (DV) to reduce cancer cells in a subject in need thereof, wherein the effective amount is an amount sufficient to increase expression of a protein on an immune cell of the subject. In some instances, the effective amount is an amount sufficient to increase expression of a protein in the immune cell. In some instances, the immune cell is a T cell. In some instances, the protein is intercellular adhesion molecule (e.g., joins two cells together). In some instances, the intercellular adhesion molecule is intercellular adhesion molecule 1 (ICAM-1). In some instances, the effective amount increases the expression of ICAM-1 by about 10% to about 500%. In some instances, the effective amount increases the expression of ICAM-1 by about 10% to about 300%. Provided herein are compositions comprising an effective amount of Dengue virus. In some instances, compositions disclosed herein comprise a sugar. In some instances, compositions disclosed herein comprise a surfactant. In some instances, compositions disclosed herein comprise a protein. In some instances, compositions disclosed herein comprise a salt. In some instances, compositions disclosed herein comprise a non-ionic surfactant, a non-reducing sugar, a salt, a carrier protein, or a combination thereof.

Provided herein are compositions comprising an effective amount of Dengue virus to reduce cancer cells in a subject in need thereof. In some instances, the composition comprises a non-ionic surfactant. In some instances, the non-ionic surfactant is a non-ionic detergent. In some instances, the non-ionic surfactant is an agent comprising a hydrophobic chain. In some instances, the non-ionic surfactant is an agent comprising polyoxyethylene. In some instances, the non-ionic surfactant is an agent comprising polyoxypropylene. In some instances, the non-ionic surfactant is an agent comprising a polyoxyethylene-polyoxypropylene block copolymer. In some instances, the non-ionic surfactant is an agent that acts as a stabilizer of a cell membrane. In some instances, the non-ionic surfactant is an agent that protects from cell membrane shearing. In some instances, the non-ionic surfactant is an agent that acts as an anti-foaming agent. In some instances, the non-ionic surfactant comprises pluronic F-68. In some instances, the non-ionic surfactant consists essentially of pluronic F-68. Additional non-limiting examples of non-ionic surfactants contemplated for use in the compositions disclosed herein include alkyl polyglycoside, cetomacrogol 1000, cetostearyl alcohol, cetyl alcohol, cocamide DEA, cocamide MEA, decyl glucoside, decyl polyglucose, glycerol monostearate, IGEPAL CA-630, isoceteth-20, lauryl glucoside, maltosides, monolaurin, mycosubtilin, narrow-range ethoxylate, nonidet P-40, nonoxynol-9, nonoxynols, NP-40, octaethylene glycol monododecyl ether, N-octyl beta-d-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80, and combinations thereof. In some instances, the non-ionic surfactant is present in the composition at a concentration of about 0.01% w/v to about 10% w/v. In some instances, the non-ionic surfactant is present in the composition at a concentration of about 0.1% w/v to about 5% w/v. In some instances, the non-ionic surfactant is present in the composition at a concentration of about 1% w/v to about 5% w/v. In some instances, the non-ionic surfactant is present in the composition at a concentration of about 2% w/v.

Provided herein are compositions comprising an amount of Dengue virus sufficient to reduce cancer cells in a subject in need thereof and a non-reducing sugar. In some instances, the non-reducing sugar is a sugar capable of trapping water molecules. In some instances, the non-reducing sugar acts as a cryoprotectant, protecting the viability of the Dengue virus during freezing and thawing. In some instances, the non-reducing sugar comprises a disaccharide. In some instances, the non-reducing sugar comprises an alpha, alpha-1,1-glucoside bond between two alpha glucose units. In some instances, the non-reducing sugar consists essentially of a disaccharide. In some instances, the non-reducing sugar comprises a trehalose. Trehalose is also known as α-D- glucopyranosyl-(1→1)-α-D-glucopyranoside, mycose, and tremalose. In some embodiments, the non-reducing sugar consists essentially of a trehalose. In some instances, the trehalose is alpha-trehalose. In some instances, the trehalose is D-(+)-Trehalose dehydrate. In some instances, the trehalose has the chemical formula of $C_{12}H_{22}O_{11} \cdot 2H_2O$. In some instances, the non-reducing sugar is present in the composition at a concentration of about 5% w/v to about 25% w/v. In some instances, the non-reducing sugar is present in the composition at a concentration of about 1% w/v to about 10% w/v. In some instances, the non-reducing sugar is present in the composition at a concentration of about 10% w/v to about 20% w/v. In some instances, the non-reducing sugar is present in the composition at a concentration of about 15% w/v.

Provided herein are compositions comprising an effective amount of Dengue virus to reduce cancer cells in a subject in need thereof, and a carrier protein. Carrier proteins may function as a carrier or stabilizer for steroids, fatty acids, or hormones. In some instances, the carrier protein is a protein capable of stabilizing a virus envelope in storage conditions (e.g., below room temperature). In some instances, the carrier protein is a soluble monomeric protein. In some instances, the carrier protein is albumin. In some instances, the carrier protein is a human protein ensuring compositions disclosed herein are compliant with good manufacturing protocol (GMP) standard. In some instances the carrier protein is human albumin. In some instances, the carrier protein is present in the composition at a concentration of about 0.1% w/v to about 10% w/v. In some instances, the carrier protein is present in the composition at a concentration of about 1% w/v to about 5% w/v. In some instances, the carrier protein is present in the composition at a concentration of about 2% w/v.

Provided herein are compositions comprising an effective amount of Dengue virus to reduce cancer cells in a subject in need thereof. In some instances, the composition comprises a salt. In some instances, the salt comprises calcium, magnesium, potassium, sodium, boron. In some instances, the salt is a phosphate salt, a chloride salt, a sulfate salt or a dichromate salt. In some instances, the salt is calcium chloride. In some instances, the salt is magnesium chloride. In some instances, compositions comprise calcium chloride and magnesium chloride. In some instances, the salt is present in the composition at a concentration of about 0.1 mM to about 10 mM. In some instances, the salt is present in the composition at a concentration of about 0.1 mM to about 5 mM. In some instances, the salt is present in the composition at a concentration of about 0.1 mM to about 2 mM. In some instances, the salt is present in the composition at a concentration of about 1 mM. In some instances, compositions comprise calcium chloride and magnesium chloride wherein calcium chloride is present in the composition at about 0.1 mM to about 10 mM, and magnesium chloride is present in the composition at about 0.1 mM to about 10 mM. In some instances, compositions comprise calcium chloride and magnesium chloride wherein calcium chloride is present in the composition at about 1 mM, and magnesium chloride is present in the composition at about 1 mM.

In some instances, compositions and methods disclosed herein modify expression of genes in cells of a subject. Exemplary modification of gene expression may be increased or decreased expression. Expression of genes in cells of the subject may be increased by DV infection, including, but not limited to, IL-1 beta, IL-2, IL-7, IL-12, IL-15, IFN-alpha, IFN-gamma, TNF-alpha, TNF-beta, GM-CSF, CD8 antigen, ICOSLG, CCL3, CCL5, TRAIL, IP10, GNLY, GZMA, HLA-DRA, HLA-DP alpha1, HLA-DP beta 1, and ZAP70. Increased levels of proteins corresponding to these genes may be observed in circulating fluids of the subject. Levels may be increased at least 2-fold. Levels may be increased between 2-fold and 1000-fold. Levels may be increased between 2-fold and 100-fold. Levels may be increased between 2-fold and 10-fold. Cell types of a subject administered DV may be increased by DV infection, including, but not limited to, CD8+CD44+62L– cells, CD4+CD44+CD62L$^{lo}$ cells, HLA-DR+CD8+ cells, Tia-1 CD8+ cells, VLA-4 CD8+ cells, ICAM-1 CD8+ cells, and LFA-1 CD8+ cells. In some instances, TNF-α, is released by the immune system during DV infection. TNFα is an inflammatory cytokine with pleiotropic effects, including direct killing of tumor cells via TRAIL (TNF-Apoptosis-Inducing-Ligand).

In some instances, DV induces high levels of soluble TRAIL (sTRAIL) from a variety of cells including γδCTL, activated M1 macrophages and plasmacytoid DC (pDC). In some instances, DV activates IFNβ, a multifunctional cytokine with a 10-fold higher affinity for the same receptor as IFNα. IFNβ has similar antiviral properties in suppressing transcription of viral RNA, but is much more potent than IFNα in inducing apoptosis in tumor cells. Nitric oxide and IFNβ could act in a synergistic fashion during dengue infection. These molecules may work in tandem to overcome resistance to apoptosis mediated by the high levels of sTRAIL induced by $M_1$ macrophages, pDC, and δγ CTL.

Provided herein are pharmaceutical compositions comprising more than one strain of Dengue virus. In some instances, the pharmaceutical compositions comprise at least a portion of a Dengue virus. The portion of the Dengue virus may be a portion sufficient to generate an immune response in a subject receiving the pharmaceutical composition. The compositions may further comprise one or more pharmaceutically acceptable salts, excipients or vehicles. Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, co-solvents, wetting agents, complexing agents, buffering agents, antimicrobials, and surfactants.

In some instances, the carriers disclosed herein comprise neutral buffered saline. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer may be about pH 7-8.5.

Provided herein are compositions that comprise a Dengue virus, wherein the composition is in liquid form, lyophilized form or freeze-dried form and may include one or more lyoprotectants, excipients, surfactants, high molecular weight structural additives and/or bulking agents. In some instances, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the virus upon lyophilization. Exemplary lyoprotectant concentrations for sugars (e.g., sucrose, lactose, trehalose) in the pre-lyophilized formulation are from about 10 mM to about 400 mM.

Provided herein are compositions that comprise a Dengue virus disclosed herein, wherein the compositions are suitable for injection or infusion. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Devices for injection of a Dengue Virus described herein may be configured for subcutaneous injection. In some instances, the device is not configured for intradermal injection. The device may have a needle gauge size of 30 to 19 G on an ISO scale. The device may have a needle gauge size of 27 to 19 G on an ISO scale. The device may have a needle gauge size of 24 to 19 G on an ISO scale. The device may have a needle gauge size of 23 to 19 G on an ISO scale. The device may have a needle gauge size of 22 to 19 G on an ISO scale. The device may have a needle gauge size of 21 to 19 G on an ISO scale. The device may have a needle length of ⅜ inches to ¾ inches. The device may have a needle length of ½ inches to ⅝ inches. The needle may be injected at an angle of 45 degrees to 90 degrees for subcutaneous injection. The injection site may be in the deltoid muscle of arm, or vastus lateralis muscle of thigh.

Disclosed herein, are methods of manufacturing and storing the DV. In some instances, the DV is stored in a 0.5 ml container. In some instances, the DV is stored in a 1.0 ml container. In some instances, the DV is stored in a 1.5 ml container. In some instances, the DV is stored in a 2.0 ml container. In some instances, the DV is stored in a 2.5 ml container. In some instances, the DV is stored in a 3.0 ml container. In some instances, the DV is stored in a 3.5 ml container. In some instances, the DV is stored in a 4.0 ml container. In some instances, the DV is stored in a 4.5 ml container. In some instances, the DV is stored in a 5.0 ml container. In some instances, the DV is stored in a 5.5 ml container. In some instances, the DV is stored in a 6.0 ml container. In some instances, the DV is stored in a 6.5 ml container. In some instances, the DV is stored in a 7.0 ml container. In some instances, the DV is stored in a 7.5 ml container. In some instances, the DV is stored in an 8.0 ml container. In some instances, the DV is stored in an 8.5 ml container. In some instances, the DV is stored in a 9.0 ml container. In some instances, the DV is stored in a 9.5 ml container. In some instances, the DV is stored in a 10 ml container. Exemplary containers include, without limitation, a bottle, vial, can, or syringe.

Provided herein are pharmaceutical compositions that comprise a Dengue virus disclosed herein, and a non-aqueous solvent. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, antioxidants, chelating agents, inert gases and the like.

Provided herein are pharmaceutical compositions that comprise a Dengue virus disclosed herein, wherein the pharmaceutical composition is formulated for inhalation, such as for example, as a dry powder. Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

Methods of Administration

Provided herein are methods comprising administering Dengue virus to a subject in need thereof. In some instances, the virus is provided in an aqueous form. In some instances, the virus is lyophilized and reconstituted in an aqueous solution (e.g., saline solution). In some instances, the virus is administered by a route selected from subcutaneous injection, intramuscular injection, intradermal injection, percutaneous administration, intravenous ("i.v.") administration, intranasal administration, intralymphatic injection, and oral administration. In some instances, the subject is infused with the virus by an intralymphatic microcatheter.

In some instances, the methods disclosed herein comprise administering Dengue virus at a dose of about 0.5 ml of $10^6$ pfu/ml. In some instances, the dose is between about $10^3$ pfu/ml and about $10^8$ pfu/ml. In some instances, the dose is between about $10^3$ pfu/ml and about $10^6$ pfu/ml. In some instances, the dose is between about $10^3$ pfu/ml to about $10^4$ pfu/ml, between about $10^4$ pfu/ml to about $10^6$ pfu/ml, between about $10^6$ pfu/ml to about $10^8$ pfu/ml, or between about $10^8$ pfu/ml to about $10^{10}$ pfu/ml. In some instances, the dose is from about $10^1$ pfu/ml, $10^2$ pfu/ml, $10^3$ pfu/ml, $10^4$ pfu/ml, $10^5$ pfu/ml, $10^6$ pfu/ml, $10^7$ pfu/ml, $10^8$ pfu/ml, or up to about $10^9$ pfu/ml. In some instances, a dose described herein is in a volume of about 0.01, 0.02, 0.03, 0.04, 0.05, 0.1, 0.2 ml or 0.3 ml. In some instances, a dose is in a volume of about 0.01 ml to about 0.03 ml, about 0.01 ml to about 0.1 ml, 0.03 ml to about 0.05 ml, 0.05 ml to about 0.07 ml, 0.07 ml to about 0.09 ml, 0.1 ml to about 0.2 ml, 0.2 ml to about 0.4 ml, 0.4 ml to about 0.6 ml.

In some instances, the methods disclosed herein comprise administering Dengue virus at a dose of about 0.5 ml of $10^6$ pfu/ml per day. In some instances, the dose is between about $10^3$ pfu/ml/day and about $10^8$ pfu/ml/day. In some instances, the dose is between about $10^3$ pfu/ml/day and about $10^6$ pfu/ml/day. In some instances, the methods disclosed herein comprise administering Dengue virus at more than one dose of about 0.5 ml of $10^6$ pfu/ml per day. In some instances, methods comprise administering a dose between about $10^3$ pfu/ml and about $10^8$ pfu/ml more than once per day. In some instances, methods comprise administering a dose between about $10^3$ pfu/ml and about $10^6$ pfu/ml more than once per day. In some instances, methods comprise administering a dose between about $10^3$ pfu/ml and about $10^8$ pfu/ml one to five times per day. In some instances, methods comprise administering a dose between about $10^3$ pfu/ml and about $10^6$ pfu/ml one to five times per day. In some instances, methods comprise administering a dose between about $10^3$ pfu/ml and about $10^8$ pfu/ml one to three times per day. In some instances, methods comprise administering a dose between about $10^3$ pfu/ml and about $10^6$ pfu/ml one to three times per day.

Provided herein are methods comprising administering a composition comprising Dengue virus to a subject in need thereof. In some instances, the composition comprises a sugar. In some instances, the composition comprises a surfactant. In some instances, the composition comprises a protein. In some instances, the composition comprises a salt. In some instances, the composition comprises a non-ionic surfactant, a non-reducing sugar, a salt, a carrier protein, or a combination thereof. In some instances, the composition comprises a non-ionic surfactant. In some instances, the non-ionic surfactant is a non-ionic detergent. In some instances, the non-ionic surfactant is an agent comprising a hydrophobic chain. In some instances, the non-ionic surfactant is an agent comprising polyoxyethylene. In some instances, the non-ionic surfactant is an agent comprising polyoxypropylene. In some instances, the non-ionic surfactant is an agent comprising a polyoxyethylene-polyoxypropylene block copolymer. In some instances, the non-ionic surfactant is an agent that acts as a stabilizer of a cell membrane. In some instances, the non-ionic surfactant is an agent that protects from cell membrane shearing. In some instances, the non-ionic surfactant is an agent that acts as an anti-foaming agent. In some instances, the non-ionic surfactant comprises pluronic F-68. In some instances, the non-ionic surfactant consists essentially of pluronic F-68. Additional non-limiting examples of non-ionic surfactants contemplated for use in the compositions disclosed herein include alkyl polyglycoside, cetomacrogol 1000, cetostearyl alcohol, cetyl alcohol, cocamide DEA, cocamide MEA, decyl glucoside, decyl polyglucose, glycerol monostearate, IGEPAL CA-630, isoceteth-20, lauryl glucoside, maltosides, monolaurin, mycosubtilin, narrow-range ethoxylate, nonidet P-40, nonoxynol-9, nonoxynols, NP-40, octaethylene glycol monododecyl ether, N-octyl beta-d-thioglucopyranoside, octyl glucoside, oleyl alcohol, PEG-10 sunflower glycerides, pentaethylene glycol monododecyl ether, polidocanol, poloxamer, poloxamer 407, polyethoxylated tallow amine, polyglycerol polyricinoleate, polysorbate, polysorbate 20, polysorbate 80, sorbitan, sorbitan monolaurate, sorbitan monostearate, sorbitan tristearate, stearyl alcohol, surfactin, Triton X-100, and Tween 80, and combinations thereof. In some instances, the non-ionic surfactant is present in the composition at a concentration of about 0.01% w/v to about 10% w/v. In some instances, the non-ionic surfactant is present in the composition at a concentration of about 0.1% w/v to about 5% w/v. In some instances, the non-ionic surfactant is present in the composition at a concentration of about 1% w/v to about 5% w/v. In some instances, the non-ionic surfactant is present in the composition at a concentration of about 2% w/v.

Provided herein are methods comprising administering a composition comprising Dengue virus to a subject in need thereof. In some instances, the composition comprises a non-reducing sugar. In some instances, the non-reducing sugar is a sugar capable of trapping water molecules. In some instances, the non-reducing sugar acts as a cryoprotectant, protecting the viability of the Dengue virus during freezing and thawing. In some instances, the non-reducing sugar comprises a disaccharide. In some instances, the non-reducing sugar comprises an alpha, alpha-1,1-glucoside bond between two alpha glucose units. In some instances, the non-reducing sugar consists essentially of a disaccharide. In some instances, the non-reducing sugar comprises a trehalose. Trehalose is also known as α-D-glucopyranosyl-(1→1)-α-D-glucopyranoside, mycose, and tremalose. In some embodiments, the non-reducing sugar consists essentially of a trehalose. In some instances, the trehalose is alpha-trehalose. In some instances, the trehalose is D-(+)-Trehalose dehydrate. In some instances, the trehalose has the chemical formula of $C_{12}H_{22}O_{11} \cdot 2H_2O$. In some instances, the non-reducing sugar is present in the composition at a concentration of about 5% w/v to about 25% w/v. In some instances, the non-reducing sugar is present in the composition at a concentration of about 1% w/v to about 10% w/v. In some instances, the non-reducing sugar is present in the composition at a concentration of about 10% w/v to about 20% w/v. In some instances, the non-reducing sugar is present in the composition at a concentration of about 15% w/v.

Provided herein are methods comprising administering a composition comprising Dengue virus to a subject in need thereof. In some instances, the composition comprises a carrier protein. Carrier proteins may function as a carrier or stabilizer for steroids, fatty acids, or hormones. In some instances, the carrier protein is a protein capable of stabilizing a virus envelope in storage conditions (e.g., below room temperature). In some instances, the carrier protein is a soluble monomeric protein. In some instances, the carrier protein is albumin. In some instances, the carrier protein is a human protein ensuring compositions disclosed herein are compliant with good manufacturing protocol (GMP) standard. In some instances the carrier protein is human albumin. In some instances, the carrier protein is present in the composition at a concentration of about 0.1% w/v to about 10% w/v. In some instances, the carrier protein is present in the composition at a concentration of about 1% w/v to about 5% w/v. In some instances, the carrier protein is present in the composition at a concentration of about 2% w/v.

Provided herein are methods comprising administering a composition comprising Dengue virus to a subject in need thereof. In some instances, the salt comprises calcium, magnesium, potassium, sodium, boron. In some instances, the salt is a phosphate salt, a chloride salt, a sulfate salt or a dichromate salt. In some instances, the salt is calcium chloride. In some instances, the salt is magnesium chloride. In some instances, compositions comprise calcium chloride and magnesium chloride. In some instances, the salt is present in the composition at a concentration of about 0.1 mM to about 10 mM. In some instances, the salt is present in the composition at a concentration of about 0.1 mM to about 5 mM. In some instances, the salt is present in the composition at a concentration of about 0.1 mM to about 2 mM. In some instances, the salt is present in the composition at a concentration of about 1 mM. In some instances, compositions comprise calcium chloride and magnesium chloride wherein calcium chloride is present in the composition at about 0.1 mM to about 10 mM, and magnesium chloride is present in the composition at about 0.1 mM to about 10 mM. In some instances, compositions comprise calcium chloride and magnesium chloride wherein calcium chloride is present in the composition at about 1 mM, and magnesium chloride is present in the composition at about 1 mM.

Provided herein are methods comprising administering an effective amount of Dengue virus disclosed herein to a subject in need thereof. In some instances, the effective amount is an amount sufficient to increase a level of at least one cytokine in the subject. In some instances, the effective amount is an amount sufficient to increase a level of at least one cytokine in the blood of the subject. In some instances, the effective amount is an amount sufficient to increase a level of at least one cytokine in a serum sample of the subject. In some instances, the effective amount is an amount sufficient to significantly increase the level of the at least one cytokine. In some instances, the effective amount is an amount sufficient to increase the level of the at least one cytokine by about 2% to about 20,000%. In some instances, the effective amount is an amount sufficient to increase the level of the at least one cytokine by about 50% to about 20,000%. In some instances, the effective amount is an amount sufficient to increase the level of the at least one cytokine by about 100% to about 20,000%. In some instances, the effective amount is an amount sufficient to increase the level of the at least one cytokine by about 100% to about 15,000%. In some instances, the effective amount is an amount sufficient to increase the level of the at least one cytokine by about 100% to about 14,000%. In some instances, the effective amount is an amount sufficient to increase the level of the at least one cytokine by about 50% to about 15,000%. In some instances, the effective amount is an amount sufficient to increase the level of the at least one cytokine by about 50% to about 14,000%.

Provided herein are methods comprising administering an effective amount of Dengue virus disclosed herein to a subject in need thereof. In some instances, the effective amount is an amount sufficient to increase a level of at least one cytokine in the subject. In some instances, the at least one cytokine is an interleukin (IL). In some instances, the at least one cytokine is an interferon (IFN). In some instances, the at least one cytokine is an interleukin. In some instances, the at least one cytokine is selected from tumor necrosis factor (TNF) alpha, IFN alpha, IFN beta, IFN gamma, interferon gamma induced protein 10 (IP-10), IL-12, IL-2R, IL-7, IL-15, granulocyte macrophage colony stimulating factor (GM-CSF), and a combination thereof. In some instances the level of TNF alpha is increased from about 50% to about 500%. In some instances the level of TNF alpha is increased from about 50% to about 300%. In some instances the level of TNF alpha is increased from about 50% to about 240%. In some instances the level of IFN alpha is increased from about 50% to about 800%. In some instances the level of IFN alpha is increased from about 50% to about 500%. In some instances the level of IFN alpha is increased from about 50% to about 420%. In some instances the level of IFN beta is increased from about 50% to about 20,000%. In some instances the level of IFN beta is increased from about 50% to about 14,000%. In some instances the level of IFN gamma is increased from about 50% to about 200%. In some instances the level of IFN gamma is increased from about 50% to about 100%. In some instances the level of IP-10 is increased from about 50% to about 8000%. In some instances the level of IP-10 is increased from about 50% to about 5000%. In some instances the level of IP-10 is increased from about 50% to about 4000%. In some instances the level of IL-12 is increased from about 20% to about 200%. In some instances the level of IL-12 is increased from about 20% to about 100%. In some instances the level of IL-12 is increased from about 20% to about 80%. In some instances the level of IL-15 is increased from about 20% to about 200%. In some instances the level of IL-15 is increased from about 20% to about 200%. In some instances the level of IL-15 is increased from about 20% to about 100%. In some instances the level of IL-7 is increased from about 50% to about 1000%. In some instances the level of IL-7 is increased from about 50% to about 1000%. In some instances the level of IL-7 is increased from about 50% to about 500%. In some instances the level of GM-CSF is increased from about 50% to about 1000%. In some instances the level of GM-CSF is increased from about 50% to about 400%. In some instances the level of GM-CSF is increased from about 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, to about 350%. In some instances the level of IL-12R is increased from about 20%, 30%, 40%, 50%, 60%, 70%, 80%, 90%, 100%, 110%, 120%, 130%, 140%, 150%, 160%, 170%, 180%, 190%, to about 200%. In some instances the level of IL-12R is increased from about 20%, 30%, 40%, 50%, 60%, 70%, 80%, 90%, 100%, 110%, 120%, 130%, 140%, 150%, 160%, 170%, 180%, 190%, up to about 200% Provided herein are methods comprising administering an effective amount of Dengue virus disclosed herein to a subject in need thereof. In some instances, the effective amount is an amount sufficient to increase a level of at least one cytokine in the subject.

Provided herein are methods comprising administering an effective amount of Dengue virus disclosed herein to a subject in need thereof. In some instances, the effective amount is an amount sufficient to increase expression of a protein in tumor cell. In some instances, the effective amount is an amount sufficient to increase expression of a protein expressed on a tumor cell. In some instances, the protein is a checkpoint protein. In some instances, this makes the tumor cell a better target for checkpoint inhibitors. In some instances, the checkpoint protein is programmed death-ligand 1 (PD-L1). In some instances, the effective amount increases the expression of PD-L1 by about 10%, 20%, 30%, 40%, 50%, 60%, 70%, 80%, 90%, up to about 100%. In some instances, the effective amount increases the expression of PD-L1 by about 10% to about 20%. In some instances, the effective amount is an amount sufficient to increase expression of a complex of proteins expressed on a tumor cell. In some instances, the complex is a major histocompatibility complex (MHC). In some instances, the MHC is a Class I MHC. In some instances, the effective amount increases the expression of the MHC by about 10%, 20%, 30%, 40%, 50%, up to about 60%. In some instances, the effective amount increases the expression of the MHC by about 10%, 20%, 30%, 40%, 50%, 60%, 70%, 80%, 90%, up to about 100%. In some instances, the effective amount increases the expression of the MHC by about 10%, 20%, 30%, 40%, 50%, 60%, 70%, 80%, 90%, 100%, 110%, 120%, 130%, 140%, up to about 150%.

Provided herein are methods comprising administering an effective amount of Dengue virus disclosed herein to a subject in need thereof. In some instances, the effective amount is an amount sufficient to increase expression of a protein on a blood cell, such as a lymphocyte, of the subject. In some instances, the effective amount is an amount sufficient to increase expression of a protein on a circulating cell of the subject. In some instances, the blood cell or circulating cell is a T cell. In some instances, the protein is intercellular adhesion molecule (e.g., joins two cells together). In some instances, the intercellular adhesion molecule is intercellular adhesion molecule 1 (ICAM-1). In some instances, ICAM-1 is expressed by endothelial cells and immune system cells such as lymphocytes. ICAM-1 expression on a T cell can be increased by a Dengue virus administration. In some instances, the effective amount increases the expression of ICAM-1 in an immune cell by about 10% to about 500%. In some instances, the expression of ICAM-1 is from about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, or up to about 500%. In some instances, the effective amount increases the expression of ICAM-1 by about 10% to about 300%. In some instances, ICAM-1 is expressed by tumor cells. ICAM-1 expression on a tumor cells can be increased by a Dengue virus administration. In some instances, the effective amount increases the expression of ICAM-1 in a tumor cell by about 10% to about 500%. In some instances, the expression of ICAM-1 is from about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, or up to about 500%. In some instances, the effective amount increases the expression of ICAM-1 by about 10% to about 300%. The level of expression can be measured by an in vitro assay such as flow cytometry.

Provided herein can be a method of treating cancer by administering a Dengue virus to increase an expression of ICAM-1 in an immune cell or in a tumor cell. Increased or persistent ICAM-1 expression may allow for improved cell-cell interaction. A cell-cell interaction can lead to increased binding of an immune cell to a cancer cell.

Combination Delivery

Figure 1C:
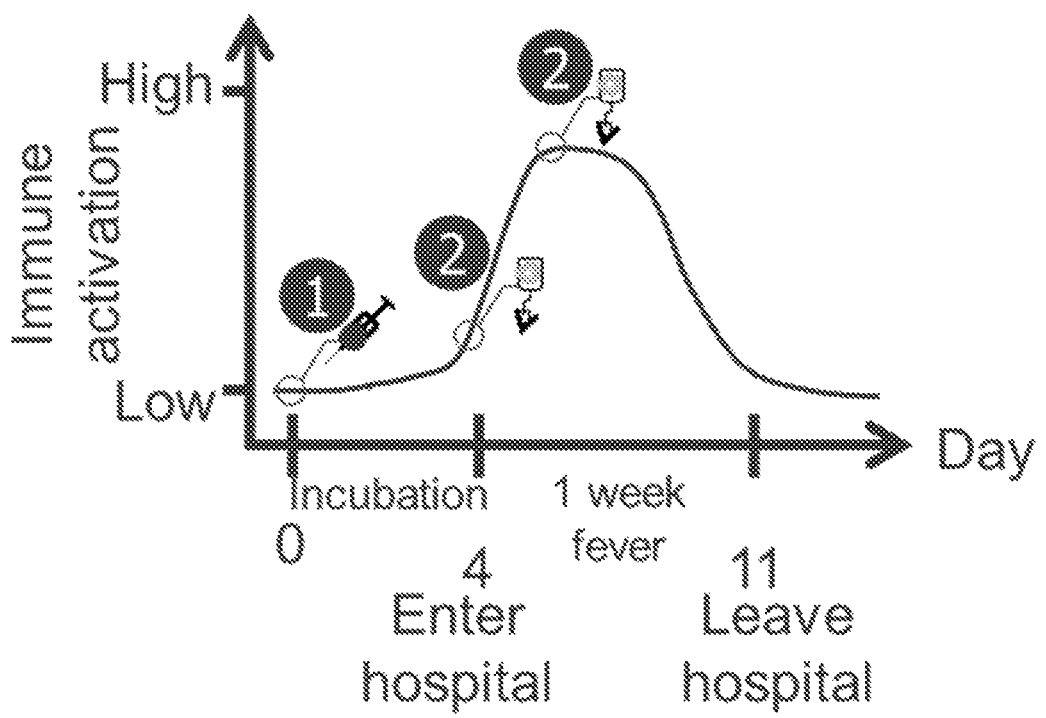
FIG. 1C illustrates a method of treatment with Dengue virus and primed dendritic cells.

Provided herein are compositions and methods wherein dendritic cell vaccination is combined with an adjuvant effect of a strain of Dengue virus (DV) to overcome tumor immune evasion mechanisms and deplete tumor cells. Methods described here may be used to treat a subject for cancer by obtaining dendritic cells and tumor cells from the subject, exposing the dendritic cells to the tumor cells or tumor cell lysate, also referred to as "pulsing" the dendritic cells, to primed (or "activated") the dendritic cells, delivering the resulting primed and tumor-targeting dendritic cells to the subject after the subject has had his/her immune system stimulated with DV (see, e.g., FIG. 1A and FIG. 1C). Optionally, the tumor antigen is not from the subject can be used for pulsing the dendritic cells.

Provided herein are methods for treating cancer in a subject in need thereof, comprising: obtaining dendritic cells (DCs); incubating the DCs with at least one tumor cell antigen; administering a Dengue Virus Type 2 serotype strain to the subject; and administering the DCs to the subject. In some instances, the Dengue Virus Type 2 serotype strain is DENV-2 #1710. In some instances, the dendritic cells are autologous dendritic cells. In some instances, the dendritic cells are allogeneic dendritic cells. In some instances, incubating the DCs with at least one tumor antigen comprises incubating the DCs with a tumor cell. In some instances, incubating the DCs with at least one tumor antigen comprises incubating the DCs with a tumor cell lysate.

Provided herein are methods comprising administering Dengue virus and dendritic cells disclosed herein to a subject in need thereof. In some instances, the Dengue virus is initially administered at least 24 hours before administering the dendritic cells. In some instances, the Dengue virus is initially administered between about 12 hours and about 96 hours before administering the dendritic cells. In some instances, the Dengue virus is initially administered between about 24 hours and about 72 hours before administering the primed dendritic cells. In some instances, the Dengue virus is initially administered between 1 day and 4 days before administering the primed dendritic cells. In some instances, the Dengue virus is administered only once. In some instances, the Dengue virus is administered more than once. In some instances, the Dengue virus is administered only before receiving dendritic cells. In some instances, the Dengue virus is administered after receiving the primed dendritic cells. In some instances, the Dengue virus is administered before and after receiving the primed dendritic cells.

In some instances, successful infection or inoculation of the subject with the Dengue virus is confirmed by the development of hyperthermia or fever. In some instances, successful infection or inoculation of the subject with the Dengue virus is confirmed by the presence or increase of circulating cytokines in the blood/plasma of the subject. Cytokines may include, but are not limited to, interleukin-2, interleukin-7, interleukin-12, interleukin-15, interleukin-2R, TNF alpha, IP-10, GM-CSF, interferon-alpha, interferon-beta, and interferon-gamma.

In some instances, methods described herein comprise administering primed dendritic cells to a subject in need thereof only once. In some instances, the primed dendritic cells are administered more than once. In some instances, the primed dendritic cells are administered a first time and a second time, wherein the first time and the second time are separated by about 1 day, about 2 days, about 3 days, about 4 days, about 5 days, or about 6 days, about 8 days, about 10 days, about 12 days, or about 18 days. In some instances, the first time and the second time are separated by about 1 week, about 2 weeks, about 3 weeks, or about a month. In some instances, the first time and the second time are separated by more than a month. In some instances, the first time and the second time are separated by less than 12 months. In some instances, the first time and the second time are separated by more than 12 months.

In some instances, methods described herein provide for administering primed dendritic cells to a subject when the subject is hyperthermic. In some instances, primed dendritic cells are administered after the subject has spike a fever. In some instances, primed dendritic cells are administered after the subject's temperature has risen to between about 37.5° C. and about 42° C. In some instances, the primed dendritic cells are administered after the subject's temperature has risen to between about 38° C. and about 42° C. In some instances, the primed dendritic cells are administered after the subject's temperature has risen to at least about 38.5° C.

In some instances, the primed dendritic cells are administered after the subject's temperature has risen to 38.5° C. In some instances, the primed dendritic cells are administered to the subject after the subject's temperature reaches 38 degrees Celsius or higher. In some instances, the subject's temperature is measured by a tympanic or oral method.

Provided herein are methods for preparation of primed dendritic cells (DCs) disclosed herein. Further provided herein are methods for exposing the primed dendritic cells to antigens associated with a disease state, e.g., tumor antigens, resulting primed dendritic cells capable of inducing specific and robust responses from cytotoxic T lymphocyte (CTL) toward cancer cells. Further provided herein are methods for administering such DCs into a subject for treatment of a disorder linked to the disease state. In some instances, the disorder is cancer. In some instances, the disorder is an autoimmune disorder, e.g., rheumatoid arthritis and multiple sclerosis. In some instances, the disorder is a human immunodeficiency virus (HIV) infection or an acquired immunodeficiency syndrome. In some instances, the subject is administered a Dengue Virus prior to administration of the primed DCs.

Provided herein are methods that comprise priming dendritic cells, wherein priming the dendritic cells involves contacting the dendritic cells with one or more tumor antigens that are present on target cancer cells. In some cases, the dendritic cells are primed with the tumor antigen alone, the tumor antigen having been synthesized, isolated or purified. Alternatively or additionally, the dendritic cells are primed with a tumor cell lysate, wherein the tumor cell lysate contains the tumor antigen. In some cases, the dendritic cell is primed with a whole cancer cell expressing the tumor antigen. The dendritic cell is then administered to the subject, where it will present the tumor antigen to the CTL, and thus, tailor the CTL for recognition and destruction of target cancer cells.

Provided herein are methods which limit dendritic cells exposure to polymers present in a plastic container material. For example, in the case of soft plastic bags, polymers may leach into the media solution and impact DC activity. Instead, dendritic cells may be cultured, stored and shipped in and on a hard container, such as a polystyrene tissue culture plate. This avoids a reduction in dendritic cell immunostimulatory activity that can be caused by exposure to polymers contained in soft plastic bags. For example, these polymers can reduce the amount of IL-12 produced by the dendritic cells, thereby reducing their capacity to induce a robust CTL response. Examples provided herein demonstrate that primed dendritic cells generated by the methods disclosed herein are capable of secreting at least 18 pg/mL of IL-12p70, whereas dendritic cells produced by standard methods typically only produce 4-6 pg/mL of IL-12p70.

In some instances, it is desirable or advantageous to prime the dendritic cells with a tumor lysate. Notably, the methods disclosed herein utilize a gentle cell lysis protocol that preserves the integrity of the tumor antigen. This gentle lysis may be achieved by exposing the tumor or cancer cells to a calcium or sodium hypochlorite solution for no more than about 30-60 minutes. Similarly, any tumor cells used to prime dendritic cells are disassociated gently, for instance, by a Miltenyi GentleMACS system, or the like.

Provided herein are primed dendritic cells prepared by the methods disclosed herein, wherein the methods comprise administering the primed dendritic cells to the subject along with an agent that boosts the subject's immune system. The combination of primed dendritic cells with a viral infection provides for an effective treatment with minimal administration, possibly as few as one time, which avoids the challenge of subject adherence to therapy. The primed dendritic cells may be autologous, meaning derived from a subject's own cells, or allogenic, derived from another subject with a similar tissue type.

Cancer

Provided herein are methods for treating a cancer disclosed herein in a subject in need thereof. Methods described herein also provide for clearing cancer cells. In some instances, administering DV to the subject induces an immune response. In some instances, the immune response is potent as compared to a common virus, such as a common cold virus. In some instances, the immune response results in tumor regression.

DNA microarray analyses have revealed that hundreds of genetically distinct tumor clones may exist in a single patient with advanced tumor. There is a pattern of negative correlation between $O_2$ supply and genetic mutation rates. The majority of agents such as cytotoxic drugs, antibodies, and small molecules, are nearly always blood-borne, exerting a Darwinian selective pressure to tumor clones that evade therapeutic mechanisms. Clones with the lowest perfusion rates have both low drug exposure and high capacity to evade immune system detection, making them resistant to conventional therapies. Provided herein are methods for cancer cell targeting, comprising inducing fever hyperthermia by administering DV to the subject with cancer, starving low-flow, resistant clones with mutated phenotypes, leaving more genetically stable clones for elimination by activated lymphocytes and other arms of the immune system. In some instances, the methods comprise combining fever with activation of CTL and lymphokine-activated killer cells (LAK) by administering pulsed DCs, lead to higher response rates than with conventional cancer therapies (e.g., antibody drug conjugates, kinase inhibitors, small molecules, etc.) or CTLs alone. The immune suppression seen in patients with advanced cancer is a complex and dynamic process. It involves tolerance to the tumor antigens themselves, which are usually recognized as "self" by CTL. In some instances, methods described herein comprise breaking this tolerance and achieving high levels of $T_H1$ cytokines, which DV infection induces.

Provided herein are compositions and methods for treatment or reduction of a cancer, comprising administration of a Dengue virus to a subject in need thereof. The cancer may be a solid cancer or blood cancer. Cancers targeted herein may be a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, sarcomas, carcinomas, lymphomas or leukemias. In some instances, the cancer is a solid tumor or a liposarcoma. In some embodiments, the cancer is an advanced cancer. By way of non-limiting example, the advanced cancer may be advanced melanoma. Advanced cancer may be a cancer that cannot be cured, but not necessarily metastatic. The cancer may be a locally advanced cancer. The locally advanced cancer may be a cancer that has spread to one or more nearby organs in contact with an organ where the cancer started, but not to distant organs. In some instances, the cancer is a sarcoma. The sarcomas may be a cancer of the bone, cartilage, fat, muscle, blood vessels, or other connective or supportive tissue. In some instances, sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g., alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma). The sarcoma may comprise a Ewing's sarcoma. In some instances, the cancer is a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. In some instances, the cancer is a neuroendocrine cancer. In some instances, the cancer is a pancreatic cancer, thyroid cancer, or a prostate cancer. In some instances, the cancer is an epithelial cancer, breast cancer, endometrial cancer, ovarian cancer, stromal ovarian cancer, or cervical cancer. In some instances, the cancer is a skin cancer. In some instances, the cancer is a neo-angiogenic skin cancer. In some instances, the cancer is a kidney cancer, a lung cancer. Exemplary lung cancers include, without limitation, a small cell lung cancer or a non-small cell lung cancer. In some instances, the cancer is a colorectal cancer, e.g., a gastric cancer or a colon cancer. In some instances, the cancer is a brain cancer. In some instances, the cancer is a brain tumor. In some instances, the cancer is a glioblastoma or an astrocytoma. In some instances, the cancer is a melanoma. The melanoma may be advanced melanoma. The melanoma may be metastatic melanoma. In some cases, a melanoma can be V600E positive. In some embodiments, the cancer cells are HLA A2 positive. In some embodiments, the cancer cells are HLA A2 negative. In some embodiments, the cancer cells have a deletion or mutation in the HLA A2 gene, so that they lack HLA A2 expression or have reduced HLA A2 expression. In some embodiments, the cancer cells are resistant to NK cell attack in the absence of an infection. In some embodiments, the cancer cells are resistant to NK cell attack in the absence of a Dengue virus infection. In some embodiments, the cancer cells express Fas. Fas is a TNF-receptor family protein expressed under stress. When ligated by FasL, apoptosis can proceed. CTL and NK, when activated, may up-regulate FasL to trigger Fas-mediated apoptosis of the cancer cells regardless of HLA expression. Administering Dengue virus may up-regulate Fas on the cancer cells. NK and CTL can then remove these cells before the damage can lead to cancer or other aberrant cell activity. In some instances, the cancer is a lung cancer. In some instances, the lung cancer is a non-small cell lung carcinoma (NSCLC), small cell lung carcinoma, or mesothelioma. Examples of NSCLC include squamous cell carcinoma, adenocarcinoma, and large cell carcinoma. In some instances, the mesothelioma is a cancerous tumor of the lining of the lung and chest cavity (pleura) or lining of the abdomen (peritoneum). In some instances, the mesothelioma is due to asbestos exposure. In some instances, the cancer is a central nervous system (CNS) tumor. In some instances, the CNS tumor is classified as a glioma or nonglioma. In some instances, the glioma is malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma. In some instances, the cancer is a blood cancer. In some instances, the cancer is leukemia. In some instances, the cancer is a myeloid leukemia. In some instances, the cancer is a lymphoma. In some instances, the cancer is a non-Hodgkin's lymphoma. In some instances, the cancer is selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, Hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. In some instances, the cancer is a hematological malignancy. In some instances, the hematological malignancy is a B cell malignancy. In some instances, the cancer is a chronic lymphocytic leukemia. In some instances, the cancer is an acute lymphoblastic leukemia. In some instances, the cancer is a CD19-positive Burkitt's lymphoma. In some instances, the leukemia is an acute lymphocytic leukemia, acute myelocytic leukemia, chronic lymphocytic leukemia, or chronic myelocytic leukemia. Additional types of leukemias include, but are not limited to, hairy cell leukemia, chronic myelomonocytic leukemia, and juvenile myelomonocytic leukemia. In some instances, the lymphoma develops from a B lymphocyte or T lymphocyte. Two major types of lymphoma are Hodgkin's lymphoma, previously known as Hodgkin's disease, and non-Hodgkin's lymphoma. In some instances, the Non-Hodgkin lymphoma is indolent. In some instances, the Non-Hodgkin lymphoma is aggressive. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Methods of Isolating and Priming Dendritic Cells (DC)

Provided herein are methods that comprise priming DCs and administering the primed DCs to a subject in need thereof, wherein the DCs induce a response from cytotoxic T lymphocytes (CTL) resulting in cytotoxicity of target cells. The DCs may comprise allogeneic dendritic cells or autologous dendritic cells. In some instances, the methods described herein comprise administering allogeneic primed dendritic cells to a subject. In some instances, the methods described herein comprise administering autologous primed dendritic cells to a subject. The methods disclosed herein comprising administering primed DCs to the subject may be referred to herein as "dendritic cell vaccination."

In some instances, methods described herein comprise obtaining dendritic cells from $CD34^+$ progenitor cells in the bone marrow. In some instances, methods described herein comprise obtaining dendritic cells from $CD1^+CD14^+$ immature monocytes in the peripheral blood. In some instances, obtaining the dendritic cells comprises leukapheresis. In some instances, leukapheresis comprises withdrawing a unit of blood from the subject or a donor, separating a series of blood-components: red cells, platelets, and most of the plasma factors, which are returned to the subject, with the white blood cells remaining. In some instances, methods described herein comprise testing the white blood cells for sterility, shipping or storing them cold (4° C.), and or processing the DCs from the apheresis product.

Provided herein are methods of producing DCs, wherein the methods comprise separating monocytes in the unit of blood from other white cells, including, but not limited to, T cells, B cells, NK cells, Eosinophils and Basophils. This may be accomplished with immuno-magnetic selection or by adherence properties. Immuno-magnetic selection involves contacting white blood cells from the unit of blood with a sterile plastic column with plastic beads coated with antibodies for immune cells, such as, by way of non-limiting example, CD surface proteins: (CD4, CD8, CD56, etc.). Unwanted (non-monocyte) cells will adhere to the beads, leaving the monocytes to pass through and be collected. In positive selection, magnetic beads may be coated with antibodies for CD1 and/or CD14 to capture monocytes, a magnet is placed against the column, and unwanted cells are flushed out of the column with a buffered saline solution or cell-viable media. The monocytes are then washed off the beads and collected in a following step. In adherence selection, the properties of monocytes to stick to certain surfaces are used to separate them by running the apheresis product down a slanted column.

Provided herein are methods for cell collection which may comprise collecting only a few thousand monocytes from the unit of blood. Currently employed methods of immunotherapy generally requires DC doses in the range of 50 million. Thus, methods disclosed herein may comprise expanding monocytes, as well as any precursors thereof, and any cells differentiated therefrom (e.g., DCs). Expanding cells may comprise contacting cells with factors such as growth factors, colony-stimulation factors, cytokines, or any other proliferation or growth inducing factors, and combinations thereof. By way of non-limiting example, the recombinant human growth factors rhuInterleukin-4 (IL-4), and rhuGranulocyte-Macrophage-Colony-Stimulation Factor (GM-CSF), may be used to accomplish the expansion of DC numbers. In addition, IL-4 and GM-CSF may be required to develop mature DCs from monocytes, which have poor antigen-uptake and CTL-stimulating ability, compared to mature DCs. Thus, IL-4 and GM-CSF may expand the number and the development of mature-DC markers. DC markers may include, but are not limited to CD11, CD80, and CD83, as well as increased expression of both Class I (for presentation of short peptides to $CD8^+$ cells), and Class II (for presentation of longer peptides to $CD4^+$ Helper-Inducer T lymphocytes) MHC complexes. Expanding cells may produce mature DCs in the tens of millions within about 2 days. Expanding cells may produce mature DCs in the tens of millions within about 3 days. Expanding cells may produce mature DCs in the tens of millions within about 4 days. Expanding cells may produce mature DCs in the tens of millions within about 5 days. Expanding cells may produce mature DCs in the tens of millions within about one week.

In some instances, methods described herein comprise contacting or pulsing DCs with peptides/antigens, tumor cells, tumor supporting cells, tumor cell lysate and/or tumor supporting cell lysate. The term "pulsing," as used herein, generally refers to contacting DCs more than once at one or more intervals, and may be used interchangeably with contacting, unless specified otherwise. In some instances, the methods comprise contacting or pulsing DCs with a peptide that binds MHC Class I molecules ("MHC Class I peptide"). In some instances, methods described herein comprise contacting or pulsing DCs with a peptide that binds MHC Class II molecules ("MHC Class II peptides"). In some instances, methods described herein comprise contacting or pulsing DCs with MHC Class I peptides and MHC Class II peptides. In some instances, the contacting or pulsing makes the DCs competent to prime CTL and target CTL to tumors. In some instances, methods described here comprise contacting or pulsing DCs with manufactured/synthetic Class I and/or Class II peptides. In some instances, the Class I and/or class II peptides are manufactured, then added to the DC medium, optionally in in microgram quantities or less. In some instances, methods described herein include Class II peptides for a sustained immune response. In some instances, methods described herein comprise DNA or RNA sequencing of the peptide (i.e. tumor antigen) and/or using electroporation to insert the DNA or RNA into the DCs to trigger antigen processing. In some instances, methods described herein do not require HLA matching of DCs. In some instances, the peptide or portion thereof is represented by an amino acid sequence selected from EGSRNQDWL (SEQ ID NO: 1), (TAYRYHLL) (SEQ ID NO: 2), or combinations thereof.

In some instances, the peptides disclosed herein are Class I peptides. Class I peptides may by manufactured, then added to the DC medium in microgram quantities. However, this technique is costly, because the peptides must be matched to the subject's HLA type, and if the tumor cell does not present that antigen, it can evade detection and lysis. The lack of Class II peptides to activate $CD4^+$ help leads to rapid decline of immune response power. Other methods may comprise RNA sequencing of common tumor antigens, then using electroporation to insert the RNA into the DCs to trigger antigen processing. This method does not require HLA matching, and includes Class II peptides for a sustained immune response. However, RNA sequencing may be technically complex, and may only present a limited number of antigens of thousands of potential gene products. For these reasons, autologous whole-tumor cells or their lysate have the advantages of low cost, ready availability by biopsy (1-2 gm sufficient), and contain the full array of potential antigens for a broad and deep immune response.

Provided herein are methods for priming dendritic cells, comprising obtaining whole tumor cells and/or lysates thereof. Tumor cells may be killed by radiation or other means and preparing lysate by various methods. In some instances, lysing the tumor cells does not comprise trypsin enzyme digestion and freeze-thaw cycles, which are simple and fast, but can damage the delicate peptides within. The methods disclosed herein may employ an automated cell processor (e.g., the Miltenyi GentleMACS system), which allows the sample to be manually minced, suspended in PBS solution, then a pre-selected tissue-specific software-controlled rotor system separates the tumor cells. The single-cell suspension may be membrane-lysed with minimal damage to tumor peptides.

In some instances, methods described herein comprise contacting the dendritic cells with autologous tumor cells or lysates thereof. In some instances, methods described herein comprise contacting the dendritic cells with autologous whole-tumor cells (e.g., tumor cells and tumor supporting cells) or lysates thereof which contain the full array of potential antigens for a broad and deep immune response. Methods for dendritic cell priming described herein may comprise contacting the dendritic cells with tumor cell lysate comprising apoptotic or necrotic bodies. In further instances, the tumor cell lysate comprises tumor antigens from the microenvironment surrounding the tumor cells, such as extracellular matrix proteins.

In some instances, methods described herein comprise contacting the DCs with an augmenting agent that will augment the priming, proliferation or viability of the DCs. By way of non-limiting example, the augmenting agent may be selected from lymphokines, monokines, cytokines, growth factors, cells, cell fragments, (non-protein) small molecules, antibodies, antibody fragments, nucleic acids, and combinations thereof.

In some instances, methods described herein for preparing cells and antigens for DC priming comprises rendering the target cells (e.g., cancer cells) incapable of cell division. For example, the methods may comprise treating cells with mytomycin C or radiation to render cells incapable of cell division. These may include cells that are added as augmenting agents or cells used to pulse DCs (e.g., tumor cells).

In some instances, methods described herein comprise pulsing the DCs from about 1 hour to about 24 hours. In some instances, methods described herein comprise pulsing the DCs from about 12 hours to about 48 hours. In some instances, methods described herein comprise pulsing the DCs from about 8 hours to about 24 hours. In some instances, methods described herein comprise pulsing the DCs for about 18 hours. Pulsing may comprise contacting the DCs at least once with the peptides/antigens, tumor cells, tumor supporting cells, tumor cell lysate and/or tumor supporting cell lysate. Pulsing may comprise contacting the DCs at least twice with the peptides/antigens, tumor cells, tumor supporting cells, tumor cell lysate and/or tumor supporting cell lysate. Pulsing may comprise contacting the DCs at least three times with the peptides/antigens, tumor cells, tumor supporting cells, tumor cell lysate and/or tumor supporting cell lysate. Pulsing may comprise contacting the DCs less than two times, less than three times, less than four times, less than five times, or less than 10 times with the peptides/antigens, tumor cells, tumor supporting cells, tumor cell lysate and/or tumor supporting cell lysate. Pulsing may comprise adding the peptides/antigens, tumor cells, tumor supporting cells, tumor cell lysate and/or tumor supporting cell lysate to the DCs more than once, such that the peptides/antigens, tumor cells, tumor supporting cells, tumor cell lysate and/or tumor supporting cell lysate accumulates in the DC culture media. Pulsing may comprise washing the cells or removing the DC culture media between one or more pulses.

In some instances, methods described herein comprise contacting DCs with a maturing agent described herein to enhance, complete or finalize the maturation of the DCs. In some embodiments, the maturing agent also acts as a "danger signal." Without this danger signal, the tumor antigen may induce $T^{reg}$ production or activity, which will ultimately lower CTL activity. In some embodiments, the maturing agent/danger signal is an inflammatory signal. The inflammatory signal may also be referred to as an inflammatory mediator. Inflammatory mediators may include cytokines, as well as other factors (e.g., chemokines, adhesion molecules, etc.), that may not be classified by those in the art as cytokines, but affect inflammation either directly or indirectly, In some embodiments, the inflammatory mediator is selected from a chemokine, a cytokine, a pathogen, a non-peptidic small molecule, a compound, an antibody, a peptide, fragments thereof, portions thereof, and combinations thereof. In some embodiments, the inflammatory signal is a modulator of a pattern recognition receptor (PRR) or pathway thereof In some instances, inflammatory signals described herein are selected from an interferon, a toll-like receptor signaling modulator, and combinations thereof. By way of non-limiting example, the interferon may be interferon-gamma. In some embodiments, the inflammatory signal is a toll-like receptor signaling pathway modulator.

In some instances, inflammatory signals described herein are toll-like receptor (TLR) signaling pathway regulators. By way of non-limiting example, the toll-like receptor signaling pathway regulator may be lipopolysaccharide (LPS), a polysaccharide from bacterial cell walls. In some instances, the toll-like receptor signaling pathway regulator may be selected from a toll-like receptor signaling pathway regulator that regulates TLR1, TLR2, TLR3, TLR4, TLR5, TLR6, TLR7, TLR8, TLR9 and TLR 10. The toll-like receptor signaling pathway regulator may be a ligand, a binding protein, an antibody, an agonist or an antagonist, of a TLR. The toll-like receptor signaling pathway regulator may be selected from a peptide, a protein, a cell fragment, a cell-wall component, a lipoprotein, a peptidoglycan, a polysaccharide, a monosaccharide, and a small molecule compound. The toll-like receptor signaling pathway regulator may be a portion of an animal cell, a plant cell, a bacterial cell, a yeast cell, a fungal cell, and combinations thereof. The toll-like receptor signaling pathway regulator may be a TLR2 signaling pathway regulator. By way of non-limiting example, the TLR2 signaling pathway regulator may be lipoteichoic acid, MALP-2, MALP-4, OspA, Porin, LcrV, lipomannan, GPI anchor, lysophosphatidylserine, lipophosphoglycan, glycophosphatidylinositol, zymosan, hsp60, and hemagglutinin. The toll-like receptor signaling pathway regulator may be a TLR4 signaling pathway regulator. By way of non-limiting example, the TLR4 signaling pathway regulator may be buprenorphine, carbamazepine, ethanol, fentanyl, levorphanol, LPS, methadone, morphine, oxcarbazepine, oxycodone, pethidine, and glucuronoxylomannan. The toll-like receptor signaling pathway regulator may be a TLR7 signaling pathway regulator. By way of non-limiting example, the TLR7 signaling pathway regulator may be a single stranded RNA or an imidazoquinoline compound. The toll-like receptor signaling pathway regulator may be a TLR8 signaling pathway regulator. By way of non-limiting example, the TLR8 signaling pathway regulator may be a single stranded RNA, a G-rich oligonucleotide or an imidazoquinoline compound. The imidazolquinoline compound may be R848. After exposure to the inflammatory signal, the DCs may up-regulate their CD80/CD83+ activation markers, increase production of IL-12p70 to induce a Type 1 CTL response, and become resistant to further antigen uptake and processing.

In some instances, methods described herein comprise contacting DCs with a maturing agent described herein to enhance, complete or finalize the maturation of the DCs. In some instances, the agent to finalize the maturation of the DCs comprises LPS bacterial cell wall. In some instances, the maturation agents comprise IFN-gamma. In some instances, the maturation agents comprise R848. In some instances, the maturation agents comprise CD40L. In some instances, the maturation agents comprise a combination of at least any two agents selected from LPS bacterial cell wall, IFN-gamma, R848 and CD40L. In some instances, the maturation agents comprise a combination of at least any three agents selected from LPS bacterial cell wall, IFN-gamma, R848 and CD40L. In some instances, the maturation agents comprise LPS bacterial cell wall, IFN-gamma, R848, CD40L, or any combination thereof. In some instances, the maturation agents are administered simultaneously. In some instances, the maturation agents are administered sequentially. In some instances, the maturation agents are administered sequentially starting with LPS being administered first. In some instances, the maturation agents are administered sequentially starting with IFN-gamma being administered first. In some instances, the maturation agents are administered sequentially starting with R848 being administered first. In some instances, the maturation agents are administered sequentially starting with LPS and IFN-gamma being administered simultaneously first. In some instances, the maturation agents are administered sequentially with LPS and IFN-gamma being administered simultaneously first followed by administration of R848, CD40L, or any combination thereof. In some instances, the maturation agents are administered sequentially with LPS and IFN-gamma being administered simultaneously first followed by administration of R848. In some instances, the maturation agents are administered sequentially with LPS bacterial cell wall and IFN-gamma being administered simultaneously first followed by administration of R848, and then of CD40L.

Provided herein are methods for producing primed dendritic cells described herein, wherein the methods comprise contacting primed dendritic cells with interferon gamma. In some embodiments, the methods comprise culturing the primed dendritic cells in a culture media with a concentration of interferon gamma selected from about 100 U/mL to about 10,000 U/mL, about 500 U/mL to about 5000 U/mL, and about 500 U/mL to about 2,000 U/mL. In some embodiments, the methods comprise culturing the primed dendritic cells in a culture media with a concentration of interferon gamma of about 500 U/mL. In some embodiments, the methods comprise culturing the primed dendritic cells in a culture media with a concentration of interferon gamma of about 1000 U/mL. In some embodiments, the methods comprise culturing the primed dendritic cells in a culture media with a concentration of interferon gamma of about 2000 U/mL.

In some instances, methods for producing primed dendritic cells described herein may comprise contacting primed dendritic cells with TLR8 agonist R848. In some embodiments, the methods comprise culturing the primed dendritic cells in a culture media with a concentration of R848 selected from about 0.1 µg/mL to about 50 µg/mL, about 1 µg/mL to about 20 µg/mL, and about 1 µg/mL to about 10 µg/mL. In some embodiments, the methods comprise culturing the primed dendritic cells in a culture media with a concentration of R848 of about 1 µg/mL. In some embodiments, the methods comprise culturing the primed dendritic cells in a culture media with a concentration of R848 of about 5 µg/mL. In some embodiments, the methods comprise culturing the primed dendritic cells in a culture media with a concentration of R848 of about 10 µg/mL.

In some instances, methods for producing primed dendritic cells described herein comprise contacting primed dendritic cells with lipopolysaccharide. In some embodiments, the methods comprise culturing the primed dendritic cells in a culture media with a concentration of lipopolysaccharide selected from about 1 ng/mL to about 100 ng/mL, about 1 ng/mL to about 50 ng/mL, and about 1 ng/mL to about 25 ng/mL. In some embodiments, the methods comprise culturing the primed dendritic cells in a culture media with a concentration of lipopolysaccharide of about 5 ng/mL. In some embodiments, the methods comprise culturing the primed dendritic cells in a culture media with a concentration of lipopolysaccharide of about 10 ng/mL. In some embodiments, the methods comprise culturing the primed dendritic cells in a culture media with a concentration of lipopolysaccharide of about 15 ng/mL.

Provided herein are methods that comprise sterility, specificity, and viability testing of primed DCs produced by the methods disclosed herein. The testing may occur before shipping or storing the DC. The testing may occur after shipping or storing the DC. The methods may comprise measuring expression level of IL-12p70 in DC, either at the RNA or protein level. IL-12p70 is an independent predictor of clinical response, tested across numerous trials in the last two decades, some with approximately 40% response rates. The expression level of IL-12p70 in primed DCs produced by the methods disclosed herein may be at least about two times greater than primed DCs produced/stored/shipped by traditional methods. The expression level of IL-12p70 in primed DCs produced by the methods disclosed herein may be at least about two times greater than primed DCs produced/stored/shipped by traditional methods ("traditional primed DCs"). The expression level of IL-12p70 in primed DCs may be at least about 10%, at least about 20%, at least about 30%, at least about 40%, at least about 50%, at least about 60%, at least about 70%, at least about 80%, at least about 90%, or at least about 100% greater than traditional primed DCs. The expression level of IL-12p70 in primed DCs may be at least about three times greater than traditional primed DCs. The expression level of IL-12p70 in primed DCs may be at least about four times greater than traditional primed DCs. The expression level of IL-12p70 in primed DCs produced by the methods disclosed herein may be about two to about twenty times greater than traditional primed DCs.

Provided herein are methods for producing dendritic cells that produce more than 6 ng/mL of IL-12p70. Also provided herein are dendritic cells that produce more than 10 ng/mL of IL-12p70. The DCs of the present application may produce at least about 10 ng/mL, at least about 12 ng/mL, at least about 14 ng/mL, at least about 16 ng/mL, at least about 18 ng/mL, at least about 20 ng/mL, at least about 22 ng/mL, at least about 24 ng/mL, at least about 26 ng/mL, at least about 28 ng/mL, at least about 29 ng/mL, or at least about 30 ng/mL. The DCs of the present application may produce from about 10 ng/mL to about 30 ng/mL. The DCs of the present application may produce from about 10 ng/mL to about 29 ng/mL. The DCs of the present application may produce from about 15 ng/mL to at least about 29 ng/mL.

CTL Response

Provided herein are methods for producing DCs described herein, comprising testing the ability of the DCs to induce a CTL response. Measuring the level of the CTL response may comprise measuring cytokines or inflammatory mediators in blood, serum or plasma from the subject. Measuring the level of the CTL response may comprise measuring a change in the level of a cytokine or inflammatory mediator in blood, serum or plasma from the subject. Measuring the level of the CTL response may comprise measuring the production of a cytokine or inflammatory mediator in vitro. Cytokines and inflammatory mediators may include interleukins, migration inhibitory proteins, monocyte chemotactic proteins, monocyte chemoattractant proteins, interferons, tumor necrosis factors, colony stimulating factors (CSFs), macrophage inflammatory proteins, monokines, chemokines, chemokine ligands (CCLs), and C-X-C motif chemokines (CXCL), and receptors thereof. Cytokines and inflammatory mediators include, but are certainly not limited to, interleukin 1 beta (IL-1b), interleukin 2 (IL-2), interleukin 4 (IL-4), interleukin 5 (IL-5), interleukin 7 (IL-7), interleukin 8 (IL-5), interleukin 10 (IL-10), interleukin 13 (IL-13), interleukin 6 (IL-6), interleukin 12 (IL-12), interleukin 15 (IL-15), interleukin 17 (IL-17), Rantes, Eotaxin, macrophage inflammatory protein 1 alpha (MIP-1a), macrophage inflammatory protein 1 beta (MIP-1b), granulocyte macrophage colony-stimulating factor (GM-CSF), monocyte chemoattractant protein-1 (MCP-1), interferon alpha (IFNa), interferon gamma (IFNg), interleukin 1 receptor alpha (IL-1Ra), interleukin 2 receptor (IL-2R), tumor necrosis factor alpha (TNFa), interferon gamma induced protein (IP-10), and monokine induced by gamma interferon (MIG). CTL response may be measured by expression of tumor response genes (MxA, etc.), enabling high cancer killing (turning "cold" tumors "hot"), and generating further tumor shrinkage in non-responder or low responders.

Hard Surface

Provided herein are methods for preparing DCs described herein, comprising culturing the DCs on a hard surface. The term, "hard surface," as used herein, generally refers to a standard plastic tissue culture plate or flask (e.g., a polystyrene plate). The methods disclosed herein comprise culturing DCs on a hard surface to which the DCs can adhere. In some embodiments, the hard surface is coated with a protein, peptide, extracellular matrix molecule, polymer, or combinations thereof. In some embodiments, the hard surface is not coated (e.g., the DCs adhere directly to the hard plastic surface). The hard surface is contrasted to a soft tissue culture bag, also known as cell differentiation bags. Soft tissue culture bags may be bags comprising polymers or chemicals (e.g., phthalates) that reduce the DC's Type 1 response capability. Soft tissue culture bags may be bags comprising polymers or chemicals that evoke a neutral Type 0 response from the DCs, rendering the DCs functionally inert. Soft tissue culture bags may be bags comprising a polymer selected from polyethylene, fluorinated ethylene propylene (FEP), hexafluoropropylene, tetrafluoroethylene, polytetrafluoroethylene, and co-polymers thereof, and combinations thereof.

Provided herein are methods for preparing DCs described herein, comprising transferring the DCs to a storage unit. The storage unit may also be a shipping unit. The storage unit may be selected from a flexible or soft container or surface (e.g., a bag) or a hard container or surface (e.g., a flask or plate). The storage unit may comprise a hard plastic surface. The storage unit may consist essentially of a hard plastic surface. The storage unit may consist of a hard plastic surface. The storage unit may comprise a non-plastic surface (e.g., glass). The storage unit may consist essentially of a non-plastic surface. The storage unit may consist of a non-plastic surface. The storage unit may be free of any polymers that would be taken up by, and/or induce a response in, cells stored within the storage unit. The storage unit may be free or essentially free of polymers that induce a neutral or Type 0 response in immature DCs. A neutral response may be characterized by low expression of IL-12p70. The storage unit may be essentially free of any polymers that would be taken up by, and/or induce a response in, cells stored within the storage unit. Essentially free may mean that the storage unit is at least 90%, at least 95%, at least 98%, or at least 99% free of any polymers that would be taken up by, and/or induce a response in, cells stored within the storage unit. Essentially free may mean that the storage unit is at least 99.5%, at least 99.6%, at least 99.7%, at least 99.8%, or at least 99.9% free of any polymers that would be taken up by, and/or induce a response in, cells stored within the storage unit.

In some instances, the storage units comprise an inner surface, wherein the inner surface is the surface of the storage unit that is in contact with cells stored therein. The inner surface may consist of a hard plastic surface. The inner surface may be glass. The inner surface may be absent of any polymers that would be taken up by, and/or induce a response in, cells stored within the storage unit. The inner surface may be constructed of polymers that are not taken up by immature DCs or any cells stored within the storage unit. The inner surface may be free of any polymers that would be taken up by, and/or induce a response in, cells stored within the storage unit. The inner surface may be essentially free of any polymers that would be taken up by, and/or induce a response in, cells stored within the storage unit. The inner surface may be at least 90%, at least 95%, at least 98%, or at least 99% free of any polymers that would be taken up by, and/or induce a response in, cells stored within the storage unit following addition of cells and storage media. The inner surface may be at least 99.5%, at least 99.6%, at least 99.7%, at least 99.8%, or at least 99.9% free of any polymers that would be taken up by, and/or induce a response in, cells stored within the storage unit following addition of cells and storage media. The inner surface may be free or essentially free of polymers that induce a neutral or Type 0 response in immature DCs. A neutral response may be characterized by low expression of IL-12p70.

Provided herein are methods for storing DCs produced by the methods described herein, wherein the storage units are suitable for freezing at −70° C. in liquid $N_2$, storage up to 1 year, and shipping to the clinic for use. The methods may comprise storing and/or shipping mature DCs, immature DCs, monocytes or blood in a storage unit. The methods may comprise shipping cells cool overnight. The methods may comprise thawing or warming cells to 37° C. (e.g., in a warm-water bath).

Methods of Isolating and Lysing Tumor Cells

Provided herein are methods for treating a subject, comprising administering the DCs produced by the methods disclosed herein to target tumor cells. In some instances, DCs are primed with tumor cells from a subject. In some instances, the tumor cells are isolated cells from a tumor microenvironment of the subject, referred to herein as tumor supporting cells. In some instances, dendritic cells are exposed to/pulsed with tumor cells, tumor supporting cells and/or peptides thereof, such that the dendritic cells will target tumor cells and/or tumor supporting cells that support tumor growth and metastasis (e.g., endothelial cells, vascular cells, immune cells, etc.). In some instances, peptides/antigens from tumor cells and tumor supporting cells induce dendritic cells or cytotoxic lymphocytes with receptors for peptides/antigens on both tumor cells and tumor supporting cells, resulting in targeting of the dendritic cells or cytotoxic lymphocytes to the tumor microenvironment rather than only the tumor cells. In some instances, tumor cells and/or tumor supporting cells are obtained from a biopsy of tumor tissue. In some instances, the biopsy comprises cells selected from tumor cells, adipocytes, fibroblasts, endothelial cells, infiltrating immune cells, and combinations thereof. In some embodiments, the methods comprise expanding tumor cells in order to have a sufficient number of tumor cells, tumor cell lysates or tumor cell antigens to effectively and optimally prime/pulse the DCs. Expanding may comprise proliferating of the tumor cells in vitro.

Provided herein are methods for activating DCs disclosed herein to target tumor cells, wherein the DCs are activated with lysed tumor cells and/or tumor supporting cells and surrounding extracellular matrix. In some instances, lysing comprises contacting the tumor cells and/or tumor supporting cells with an $NH_4Cl$ enzyme solution to eliminate red blood cells. In some instances, the lysing comprises contacting the tumor cells and/or tumor supporting cells with hypochlorous acid solution to induce immunogenic cell death. In some instances, the cells are lysed gently enough to not destroy peptides. In some instances, the cells are lysed to produce apoptotic or necrotic bodies. In some instances, the methods comprise lysing the tumor cells and/or tumor supporting cells with an enzymatic solution. In some instances, the methods comprise lysing the tumor cells and/or tumor supporting cells with a peroxide-free solution or a low peroxide-containing solution.

Provided herein are methods for activating DCs disclosed herein comprising lysing the tumor cells with a hypochlorite solution (HOCL). In some instances, the hypochlorite solution comprises sodium chlorite. In some instances, the hypochlorite solution comprises calcium chlorite. In some instances, the concentration of the hypochlorite in a media in which the tumor cells are suspended is about 10 μM, about 20 μM, about 30 μM, about 40 μM, about 50 μM, about 60 μM, about 70 μM, about 80 μM, about 90 μM, or about 100 μM.

Provided herein are methods for methods activating DCs produced by the methods described herein, wherein the methods comprise lysing the tumor cells and/or tumor supporting cells with a detergent solution prior to contact with the DCs. In some instances, the detergent is selected from, but is not limited to, Triton X-100, Triton X-114, NP-40, Brij-35, Brij-58, Tween 20, Tween 80, octyl glucoside, octyl thioglucoside, SDS, CHAPS, and CHAPSO. In some instances, the detergent solution is purified of peroxides, and other impurities. In some instances, the detergent is about 0.1% to about 10% v/v of the detergent solution. In some instances, the detergent is about 0.1% to about 5% v/v of the detergent solution. In some instances, the detergent is about 0.5% to about 5% v/v of the detergent solution. In some instances, the detergent is about 1% to about 10% v/v of the detergent solution. In some instances, the detergent is about 1% to about 5% v/v of the detergent solution. In some instances, the methods comprise lysing cells without shaking, vortexing, freezing, thawing, shear pressure, sonicating and/or heating the cells.

In some instances, the methods for cell lysis described herein further comprise stopping or neutralizing the lysing. For example, cells may be washed with a buffered saline solution (phospho-buffered saline solution or Hank's balanced salt solution) to neutralize the lysing.

Kits

Disclosed herein can be kits comprising compositions. Disclosed herein can also be kits for the treatment or prevention of a cancer, pathogen infection, or immune disorder. In some cases, a kit can include a therapeutic or prophylactic composition containing an effective amount of a composition of Dengue virus in unit dosage form. In some cases, a kit comprises a sterile container which can contain a therapeutic composition of Dengue virus; such containers can be boxes, ampules, bottles, vials, tubes, flasks, bags, pouches, blister-packs, or other suitable container forms known in the art. Such containers can be made of plastic, glass, laminated paper, metal foil, or other materials suitable for holding medicaments. In some cases, a kit can include cells, such as dendritic cells, from about $1\times10^4$ cells to about $1\times10^{12}$ cells. In some cases a kit can include at least about $1\times10^5$ cells, at least about $1\times10^6$ cells, at least about $1\times10^7$ cells, at least about $4\times10^7$ cells, at least about $5\times10^7$ cells, at least about $6\times10^7$ cells, at least about $6\times10^7$ cells, at least about $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $6\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $6\times10^{11}$ cells, at least about $6\times10^{11}$ cells, at least about $8\times10^{11}$ cells, at least about $9\times10^{11}$ cells, or at least about $1\times10^{12}$ cells. For example, about $5\times10^{10}$ cells can be included in a kit. In another example, a kit can include $3\times10^6$ cells; the cells can be expanded to about $5\times10^{10}$ cells and administered to a subject. Such kits can further comprise instructions for use thereof.

EXAMPLES

Example 1. Generation and Pulsing of Murine Dendritic Cells (DCs)

A method as described by Lutz M., et. al. (J. Immunol. Methods 223:77-92, 1999), was employed to generate mature DCs from mouse bone marrow. Bone marrow suspensions were incubated in petri dishes in medium supplemented with recombinant murine GM-CSF for 10 days. Non-adherent cells were collected, centrifuged and resuspended in medium containing GM-CSF and lipopolysaccharide. Two days later, the DCs were harvested and their viability was determined by trypan-blue exclusion. Purity of the DCs was determined by flow cytometry analysis. DCs were pulsed with the synthetic peptides at 10 μg/ml for 18 hours. After 18 hours of incubation, DCs were harvested, washed twice in HBSS, and resuspended in HESS for additional analysis (see Example 2 and 3).

Figure 2:
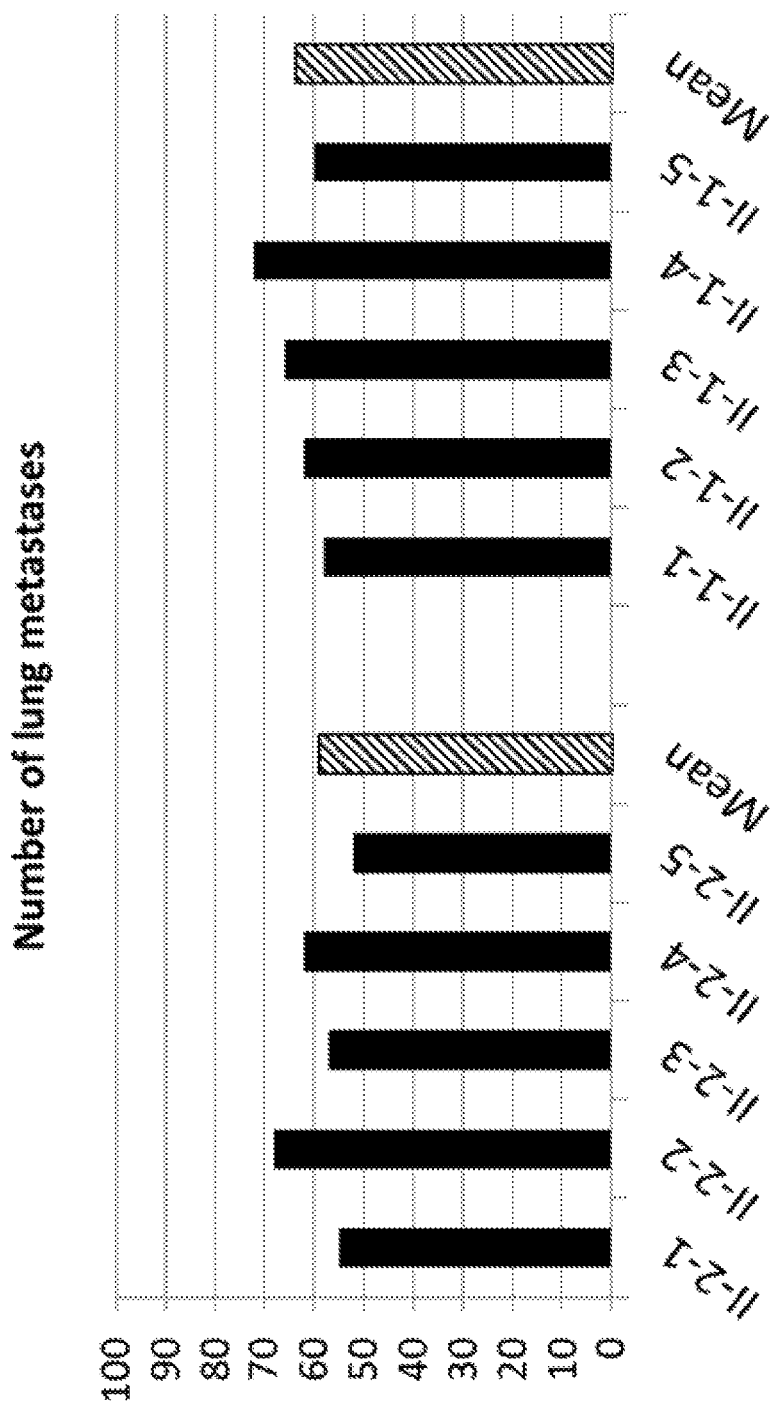
FIG. 2 is a plot of corresponding to the number of lung metastases from melanoma cells in mice under various treatment conditions. The patterned bars depict the mean number of lung metastases for each condition.

Example 2. Dengue Virus and Dendritic Cells for the Treatment of Melanoma in a First Mouse Model A mouse model assay was performed to observe results from combination targeting of cancer cells using a Dengue virus (DV) strain and tumor antigen primed dendritic cells (DCs). DV C57BL/6 mice were inoculated with 0.05 ml of Dengue virus (DEN-2 strain #1710) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 (rIL-2) and 500 IU (rIFN-gamma) on days 5, 10, 15, and 20 following administration of Dengue virus (DEN-2 strain #1710, CDC database entry number 555, provided by Dr. Duane Gubler). Seven days after the Dengue virus administration, C57BL/6 mice were immunized with mouse DCs incubated with the 2 peptides separately and injected intravenously. Peptides were synthesized. The H-2b-restricted peptide from Ovalbumin (OVA-8), SIINFEKL (SEQ ID NO: 7), was used as a control. B16 melanoma-associated H-2b-restricted peptides derived from the antigens gp100/pme117 (EGSRNQDWL (SEQ ID NO: 1)) and from TRP-1/75 (TAYRYHLL (SEQ ID NO: 2)) were used to pulse murine DCs (see Example 1 for details). Two additional immunizations with DCs were given at 14-day intervals. Three days after the last DC infusion, mice were challenged with $5\times10^4$ viable B16 melanoma cells intravenously in the lateral tail vein and then followed for survival, which was recorded as the percentage of surviving animals over time (in days) after tumor injection. Data was recorded from five or more mice/group (see Table 4 and FIG. 2).

Tumors were established in mice using the H-2b-restricted B16 murine melanoma cells line (ATCC #CRL-6322). Peptides (B16 melanoma associated H-2b-restricted peptides derived from antigens gp100/pme117 and from TRP-1/gp75) used for pulsing the dendritic cells were synthesized. Dendritic cells were generated from mouse bone marrow according to methods as described in Lutz et al. (J. Immunol. Methods 223:77-92, 1999).

On day 0, mice received $5\times10^4$ viable B16 melanoma cells intravenously in the lateral tail vein to establish pulmonary metastases. On day 7, the mice were inoculated with 0.05 ml of Dengue virus (DEN-2 strain #1710, CDC database entry number 555) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 IU (rIL-2) and 500 IU (rIFN-gamma) at 5-day intervals following administration of Dengue virus (DEN-2 strain #1710). On days 21, 35 and 49, the mouse DCs were incubated with the 2 peptides separately and injected intravenously in 2 sequential administrations on the same day to match the route and schedule of administration in subjects (see Example 2 for additional details). Control groups of mice received no Dengue virus or dendritic cells pulsed with H-2b-restricted peptide from ovalbumin (OVA-8), SIINFEKL. Treatment and control groups are shown in Table 5.

TABLE 4

| Condition | Group | MOUSE ID | NO. OF LUNG METASTASES | Mean |
|---|---|---|---|---|
| DV$10^6$ pfu/ml + 2 × $10^6$ DCs pulsed with gp100/TRP2 | 2 | II-2-1 | 55 | |
| DV$10^6$ pfu/ml + 2 × $10^6$ DCs pulsed with gp100/TRP2 | 2 | II-2-2 | 68 | |
| DV$10^6$ pfu/ml + 2 × $10^6$ DCs pulsed with gp100/TRP2 | 2 | II-2-3 | 57 | |
| DV$10^6$ pfu/ml + 2 × $10^6$ DCs pulsed with gp100/TRP2 | 2 | II-2-4 | 62 | |
| DV$10^6$ pfu/ml + 2 × $10^6$ DCs pulsed with gp100/TRP2 | 2 | II-2-5 | 52 | 58.8 |
| No DV + 2 × $10^6$ DCs pulsed with gp100/TRP2 | 1 | II-1-1 | 58 | |
| No DV + 2 × $10^6$ D DCs C pulsed with gp100/TRP2 | 1 | II-1-2 | 62 | |
| No DV + 2 × $10^6$ DCs pulsed with gp100/TRP2 | 1 | II-1-3 | 66 | |
| No DV + 2 × $10^6$ DCs pulsed with gp100/TRP2 | 1 | II-1-4 | 72 | |
| No DV + 2 × $10^6$ DCs pulsed with gp100/TRP2 | 1 | II-1-5 | 60 | 63.6 |

The number of lung metastases observed in mice administered in Group 2 (Dengue Virus serotype 2 strain #1710 and tumor peptide primed DCs) was 7.5% lower than control mice in Group 1, administered the tumor peptide primed DCs without the Dengue virus.

Example 3. Dengue Virus and Dendritic Cells for the Treatment of Melanoma in a Second Mouse Model A mouse model assay was performed to observe results from combination targeting of cancer cells using a Dengue virus (DV) strain and tumor antigen primed DCs. Mice were administered cytokines to parallel the response to DV observed in humans.

TABLE 5

Experimental groups for testing Dengue virus and DC effects on melanoma metastasis to lung

| Dengue Virus | # of dendritic cells and type of peptide |
|---|---|
| | Group A |
| $10^6$ pfu/ml | $10^6$ DCs pulsed with gp100/pme117 (EGSRNQDWL) (SEQ ID NO: 1) |
| | $10^6$ DCs pulsed with TRP-1/gp75 (TAYRYHLL) (SEQ ID NO: 2) |
| Total | 2 × $10^6$ DCs pulsed with peptide/mouse |

TABLE 5-continued

Experimental groups for testing Dengue virus and DC effects on melanoma metastasis to lung

| Dengue Virus | # of dendritic cells and type of peptide |
|---|---|
| | Group B |
| $10^6$ pfu/ml | $10^7$ DCs pulsed with gp100/pme117 (EGSRNQDWL) (SEQ ID NO: 1) |
| | $10^7$ DCs pulsed with TRP-1/gp75 (TAYRYHLL) (SEQ ID NO: 2) |
| Total | $2 \times 10^7$ DCs pulsed with peptide/mouse |
| | Group C-Control |
| None | $10^6$ DCs pulsed with gp100/pme117 (EGSRNQDWL) (SEQ ID NO: 1) |
| | $10^6$ DCs pulsed with TRP-1/gp75 (TAYRYHLL) (SEQ ID NO: 2) |
| Total | $2 \times 10^6$ DCs pulsed with peptide/mouse |
| | Group D-Control |
| $10^6$ pfu/ml | $10^6$ DCs pulsed with OVA (SIINFEKL) (SEQ ID NO: 7) |
| | $10^6$ DCs pulsed with OVA (SIINFEKL) (SEQ ID NO: 7) |
| Total | $2 \times 10^6$ DCs pulsed with peptide/mouse |

Figure 3:
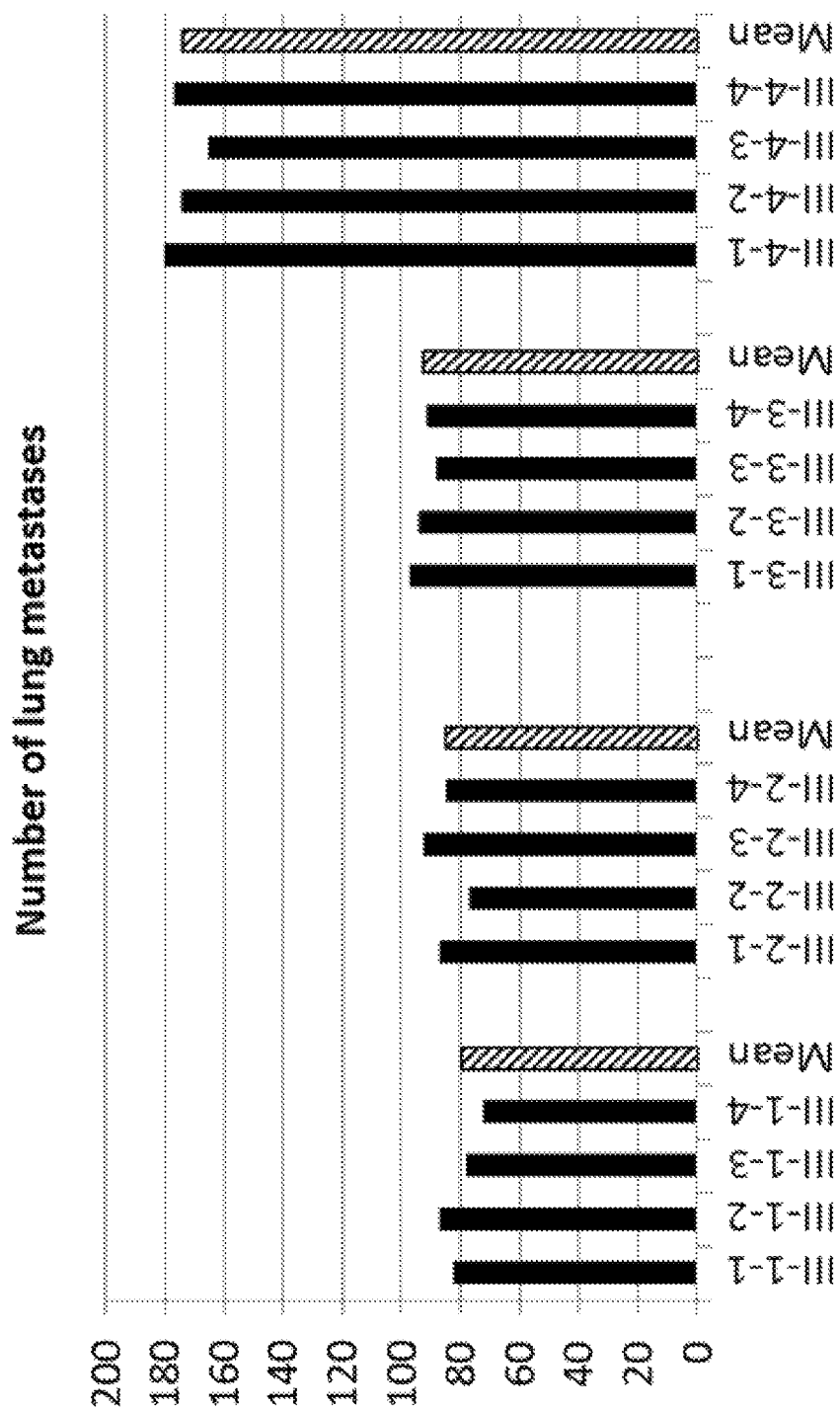
FIG. 3 is a plot of corresponding to the number of lung metastases from melanoma cells in mice under various treatment conditions. The patterned bars depict the mean number of lung metastases for each condition.

On day 90, animals were sacrificed and lung tumor colonies were counted. Pulmonary metastases were enumerated in a blinded, coded fashion after insufflation and fixation of the lungs with Fekette's solution. Data were reported as the mean number of metastases; four mice/group (see Table 6 and FIG. 3). Histopathology of the following major organ systems were performed: brain, heart, lungs, liver, kidneys, spleen and gonads (data not shown).

TABLE 6

Results for testing Dengue virus and DC effects on melanoma metastasis to lung

| Condition | Group | MOUSE ID | NO. OF LUNG METASTASES | Mean |
|---|---|---|---|---|
| DV$10^6$ pfu/ml + $2 \times 10^6$ DC pulsed with gp100/TRP2 | A | III-1-1 | 82 | |
| DV$10^6$ pfu/ml + $2 \times 10^6$ DC pulsed with gp100/TRP2 | A | III-1-2 | 87 | |
| DV$10^6$ pfu/ml + $2 \times 10^6$ DC pulsed with gp100/TRP2 | A | III-1-3 | 78 | |
| DV$10^6$ pfu/ml + $2 \times 10^6$ DC pulsed with gp100/TRP2 | A | III-1-4 | 72 | |
| | | | | 79.75 |
| DV$10^7$ pfu/ml + $2 \times 10^6$ DC pulsed with gp100/TRP2 | B | III-2-1 | 87 | |
| DV$10^7$ pfu/ml + $2 \times 10^6$ DC pulsed with gp100/TRP2 | B | III-2-2 | 77 | |
| DV$10^7$ pfu/ml + $2 \times 10^6$ DC pulsed with gp100/TRP2 | B | III-2-3 | 92 | |
| DV$10^7$ pfu/ml + $2 \times 10^6$ DC pulsed with gp100/TRP2 | B | III-2-4 | 85 | |
| | | | | 85.25 |
| No dengue virus + $2 \times 10^6$ DC pulsed with gp100/TRP2 | C | III-3-1 | 97 | |
| No dengue virus + $2 \times 10^6$ DC pulsed with gp100/TRP2 | C | III-3-2 | 94 | |
| No dengue virus + $2 \times 10^6$ DC pulsed with gp100/TRP2 | C | III-3-3 | 88 | |
| No dengue virus + $2 \times 10^6$ DC pulsed with gp100/TRP2 | C | III-3-4 | 91 | |
| | | | | 92.5 |
| DV$10^6$ pfu/ml + $2 \times 10^6$ DC pulsed with OV | D | III-4-1 | 180 | |
| DV$10^6$ pfu/ml + $2 \times 10^6$ DC pulsed with OV | D | III-4-2 | 174 | |
| DV$10^6$ pfu/ml + $2 \times 10^6$ DC pulsed with OV | D | III-4-3 | 165 | |
| DV$10^6$ pfu/ml + $2 \times 10^6$ DC pulsed with OV | D | III-4-4 | 177 | |
| | | | | 174 |

The number of lung metastases observed in mice in Group C (administered tumor antigen primed DCs and no virus) was 47% less than control Group D (administered DENV-2 #1710 and DCs exposed to a control peptide). The number of lung metastases observed in mice in Group A (administered DENV-2 #1710 and tumor antigen primed DCs) was 54% less than control Group D (administered DENV-2 #1710 and DCs exposed to a control peptide). The number of lung metastases observed in mice in Group B (administered DENV-2 #1710 and tumor antigen primed DCs) was 51% less than control Group D (administered DENV-2 #1710 and DCs exposed to a control peptide). The average reduction in Group A and B compared to Group D was 52.8%.

Example 4. Manufacture and Screening of Dengue Virus

A Master Cell Bank with validated and certified cell lines from Vero (African Green Monkey Kidney Cells) was generated and tested for absence of any contaminants and adventitious organisms. Vero lines are used by the World Health Organizations to produce a variety of viral vaccines. Dengue virus was passaged in a validated Vero Line derived from the Master Cell Bank and established as a Working Cell Bank according to guidelines established by the FDA Center for Biologics (CBER). Two Dengue Virus Type 2 strains (DNV-2 #1584 and DENV-2 #1710) from initial seed stocks were added to the Vero Cells of the WCB at a MOI of $10^{-5}$.

The first 4-ml overlay medium—containing 1% SeaKem LE agarose (FMC BioProducts, Rockland, Maine) in nutrient medium (0.165% lactalbumin hydrolysate [Difco Laboratories, Detroit, Mich.]), 0.033% yeast extract [Difco], Earle's balanced salt solution, 25 mg of gentamicin sulfate [BioWhittaker, Walkersville, Md.] and 1.0 mg of amphotericin B [Fungizone; E. R. Squibb & Sons, Princeton, N.J.], per liter and 2% FBS) —was added after adsorption of the 200-ml virus inoculum for 1.5 h at 37° C. Following incubation at 37° C. for 7 days, a second 2-ml overlay containing additional 80 mg of neutral red vital stain (GIBCO-BRL, Gaithersburg, Md.) per ml was added. Plaques were counted 8 to 11 days after infection.

A plaque assay on final virus cultures was performed. The titer of DNV-2 #1584 was approximately 5E+06 PFU/ml, and the titer of DENV-2 #1710 was 3.5E+06 pfu/mL as estimated from plaque assays. Dengue virus 2 (DNV-2; #1584) from ATCC showed a clear cytopathic effect in Vero cells 5 days post infection, whereas Vero cells appears to have a morphology change 11 days post infection of the blind passage #2 (#1710 virus). (Data not shown.) The assay shows that the DENV-2 #1710 virus is far less cytopathic than the DNV-2 #1584 strain.

Example 5. Cancer Killing Assay with Pulsed DC, with and without DV

In a control arm, normal human tumor infiltrating lymphocytes (TILs) were directly applied to human melanoma FEMX cells. T-cell receptors were matched to FEMX melanoma cell line via HLA A2.1+. In a treatment arm human TILs were exposed to DV supernatants containing interferons and interleukins. Exposed TILs+DV supernatants were placed in culture with FEMX tumor cells. Both arms were left to kill cancer cells for 4 hours at a ratio of 5-to-1 T-cell to tumor cell (100,000 cells to 20,000 cells). Surviving tumor cells were then counted as % of starting cells by flow cytometry. Results, shown in Table 7, demonstrate that DV induces 35% additional cancer cell killing beyond the pulsed DC anti-cancer response.

TABLE 7

| DV enhancement of pulsed DC anti-cancer activity | | |
|---|---|---|
| | % FL2-A− | % FL2-A+ (% Apoptotic Cells) |
| CTL | 86.1% | 13.9% |
| CTL + DV Sups | 81.2% | 18.8% |

Example 6. Human Dendritic Cell Isolation and Pulsing with Melanoma Lysate Antigens The following example demonstrates generation of a highly pure CD11a+ mature DC population expressing high levels of human IL-12p70 from pure, isolated CD14+ monocytes, as well as priming of the DC with melanoma cell lysate, the entire process being completed in less than one week. Cells were cultured on hard plastic plates and not exposed to soft plastic bags.

Figure 4:
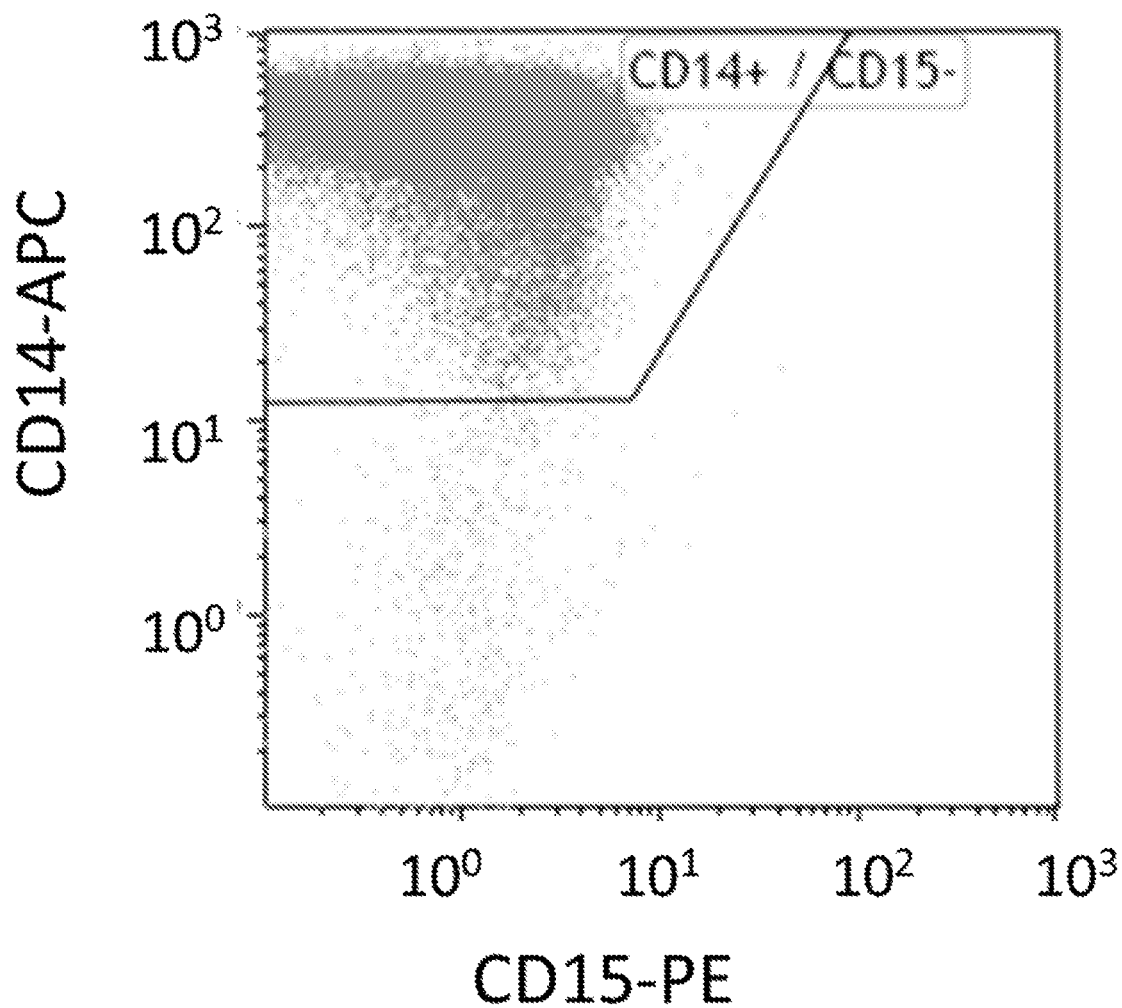
FIG. 4 is a plot of flow cytometry data confirming isolation of CD14+ monocytes.

CD14+ monocytes were isolated and analyzed for expression of CD14, CD15, CD45 and 7AAD. Post-prodigy run, 90.25% of input cells were CD14+(see FIG. 4). CD14+ cells were treated with GM-CSF and IL-4 24 hours post plating to generate immature dendritic cells.

RPMI-7951 melanoma cells from ATCC arrived on the day of the prodigy run and were re-suspended, counted and plated. Melanoma cells were than treated with a calcium hypochlorite solution. Alternatively, cells were treated with sodium chlorite solution. The melanoma cell lysate was added to the immature DC, and maturing agents IFN-gamma (1000U/mL), R848 (5 µg/mL) and LPS (long/mL) were added. In terms of timing, LPS and IFN-gamma were administered early, and R848 was administered subsequently. CD40L may optionally be administered later in the maturation process.

Figure 5:
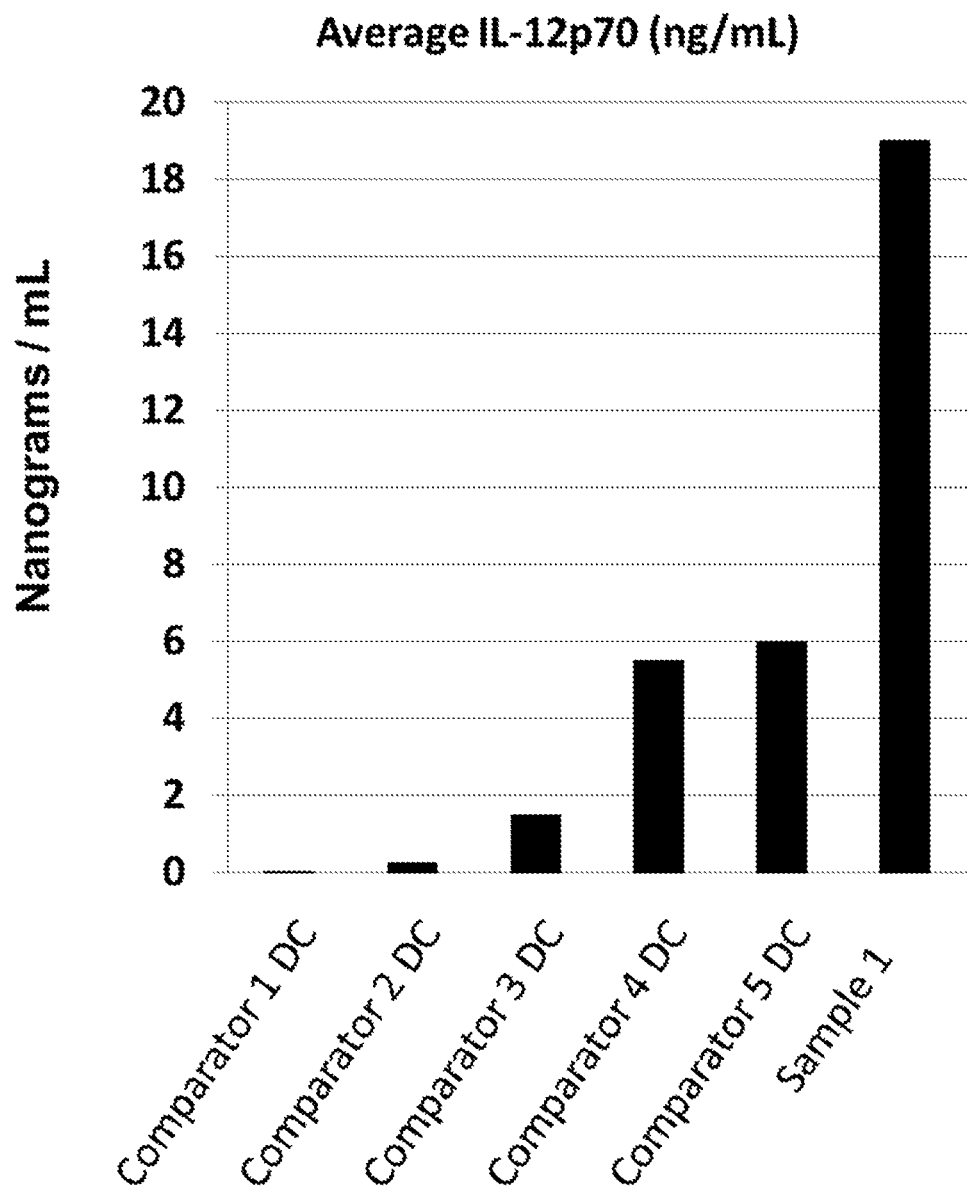
FIG. 5 is a plot of protein expression data for IL-12p70 expressed by DCs produced by methods disclosed herein relative to that of DCs produced by comparator methods.
Figure 6:
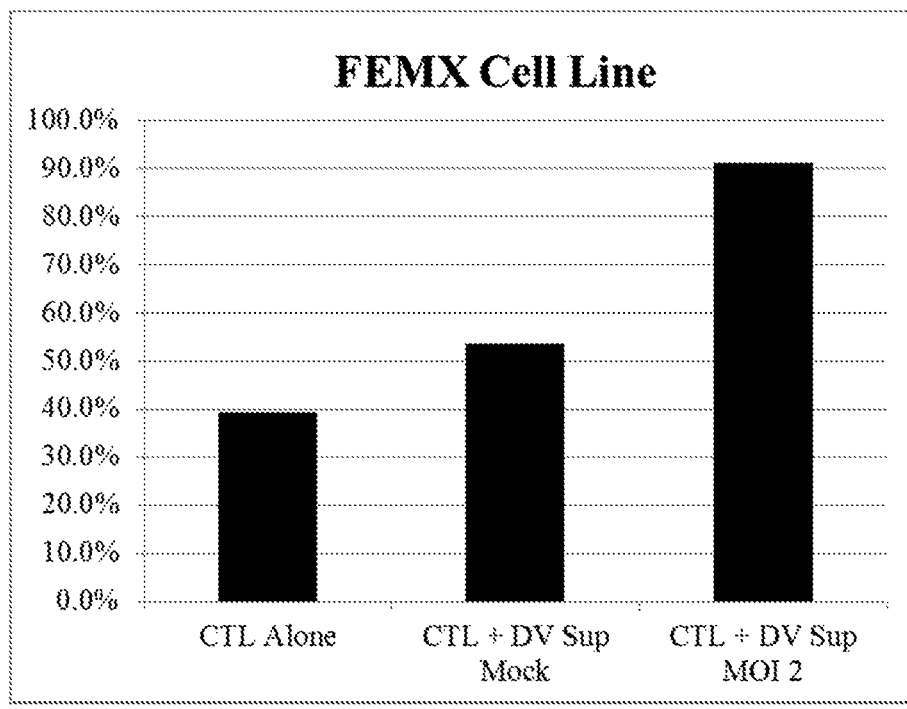
FIG. 6 is a plot of cytotoxicity of Dengue Virus induced supernatant on a melanoma cell line (FEMX cells) in the presence of cytotoxic T lymphocytes. The Y axis is a percentage of cells death relative to total cells.
Figure 7:
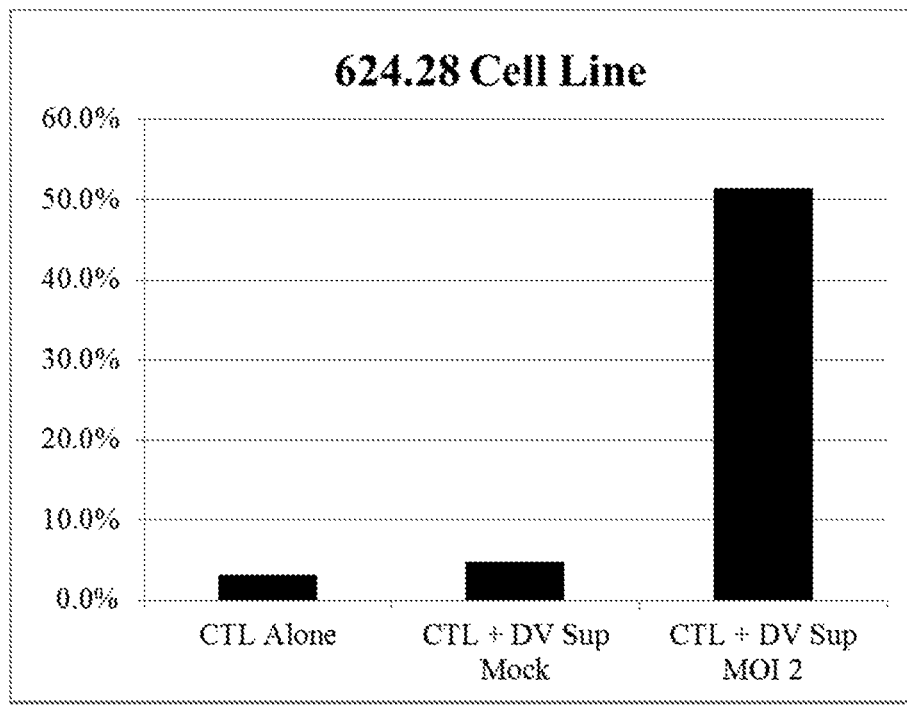
FIG. 7 is a plot of cytotoxicity of Dengue Virus induced supernatant on a melanoma cell line (624.28 cells) in the presence of cytotoxic T lymphocytes. The Y axis is a percentage of cells death relative to total cells.
Figure 8:
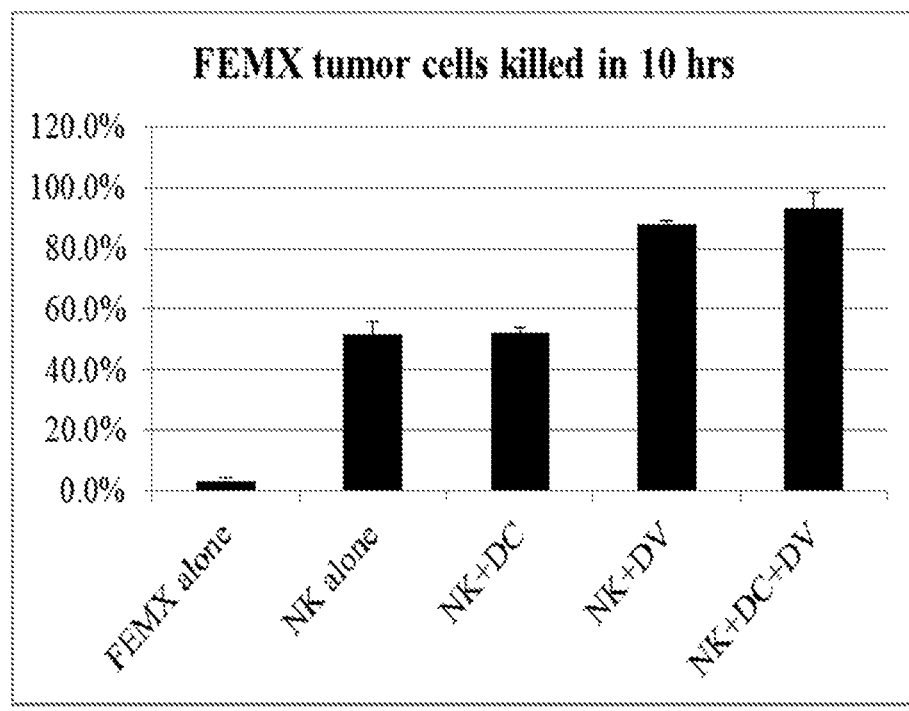
FIG. 8 is a plot of cytotoxicity of Dengue Virus induced supernatant and natural killer cells on a melanoma cell line (FEMX cells). The Y axis is a percentage of cells death relative to total cells.
Figure 9:
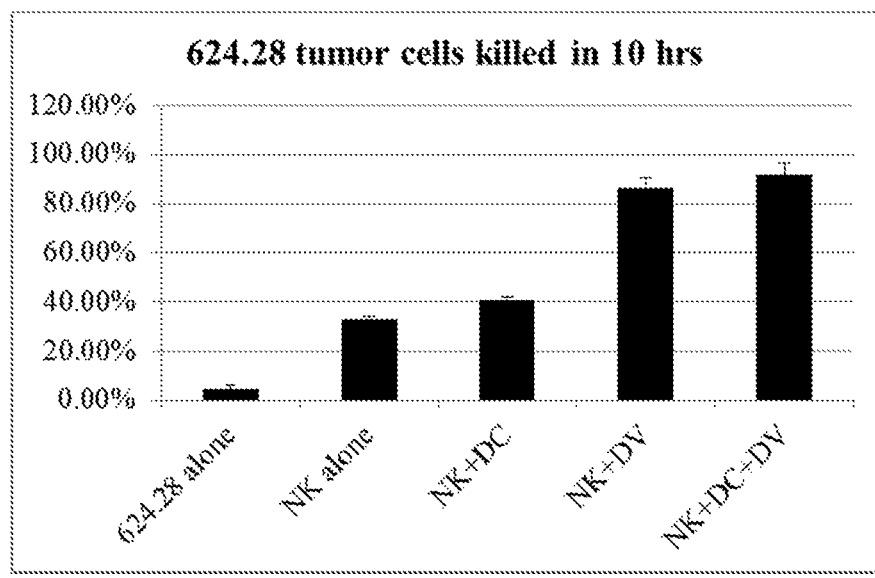
FIG. 9 is a plot of cytotoxicity of Dengue Virus induced supernatant and natural killer cells on a melanoma cell line (FEMX cells). The Y axis is a percentage of cells death relative to total cells.
Figure 10:
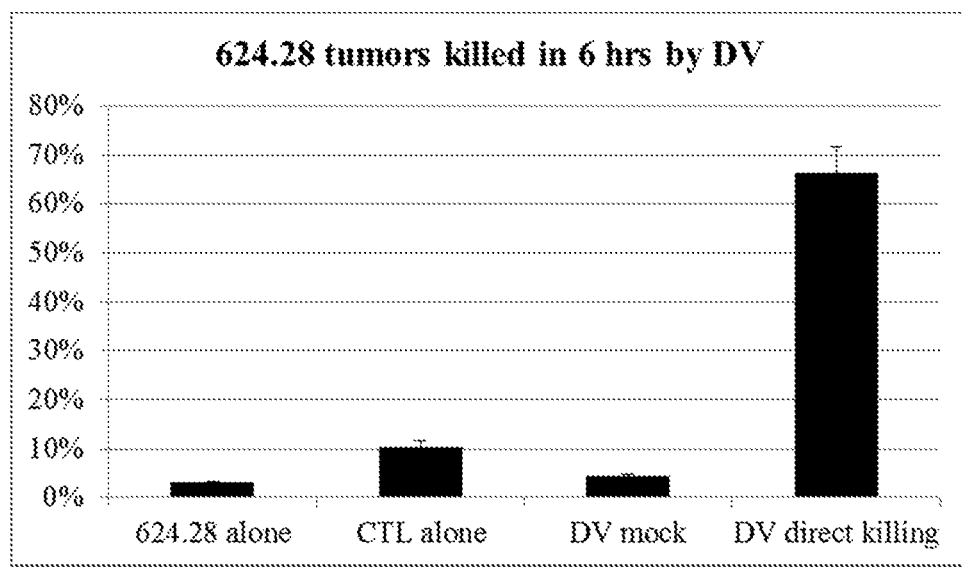
FIG. 10 is a plot of DV induced supernatants are cytotoxic to melanoma cell line 624.28 cells in the absence of cytotoxic T lymphocytes (CTL) or natural killer (NK) cells. The Y axis is a percentage of cells death relative to total cells.
Figure 11:
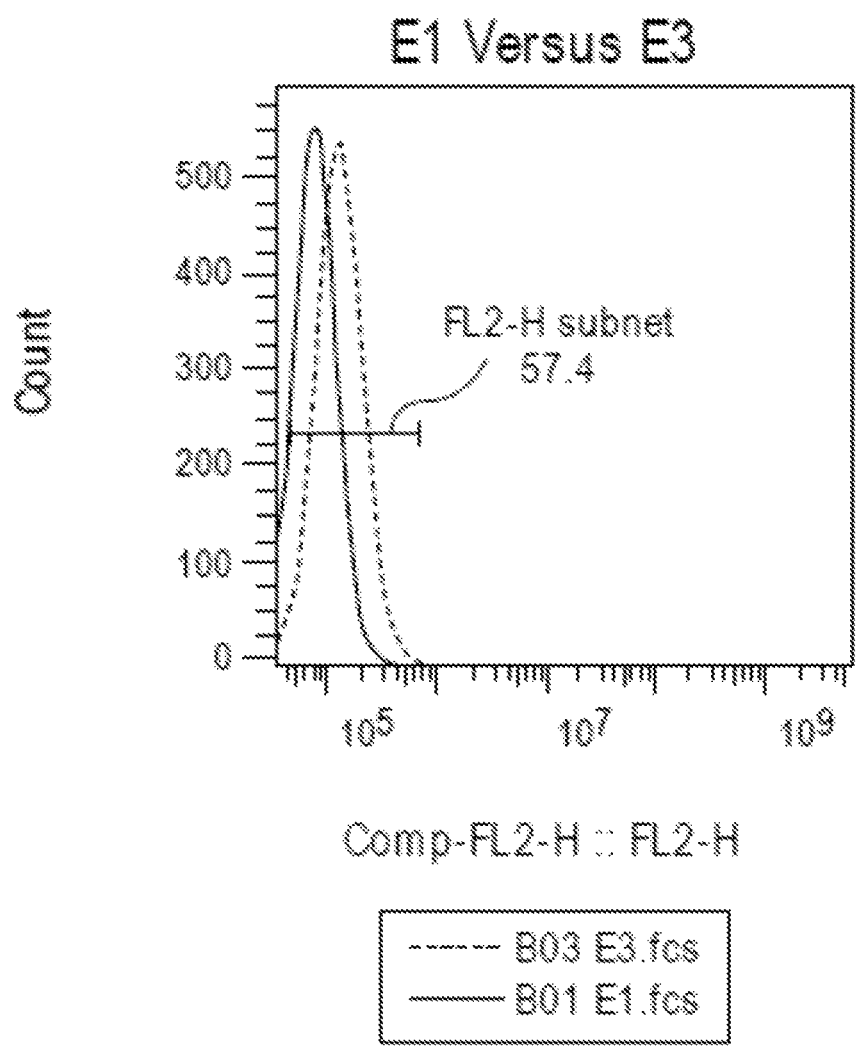
FIG. 11 is a plot of flow cytometry data measuring the up-regulation in Class I MHC expression post infection of human white blood cells with Dengue Virus. The numbers in the geometric mean refer to a brightness measure of the fluorescence when the antibody is dyed with a florescent marker. This marker the can be quantified via a typical flow cytometry laser reader.
Figure 12A:
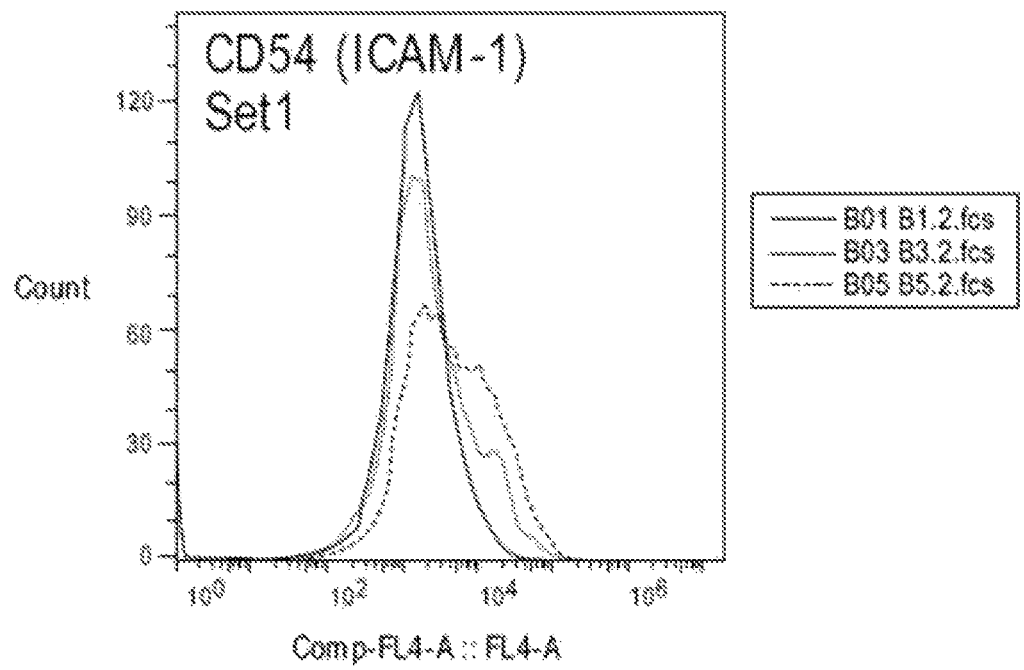
FIG. 12A and FIG. 12B are replicate plots, set 1 and set 2, of flow cytometry data measuring the up-regulation of ICAM-1 post infection of human white blood cells with Dengue Virus. The numbers in the geometric mean refer to a brightness measure of the fluorescence when the antibody is dyed with a florescent marker. This marker the can be quantified via a typical flow cytometry laser reader.
Figure 12B:
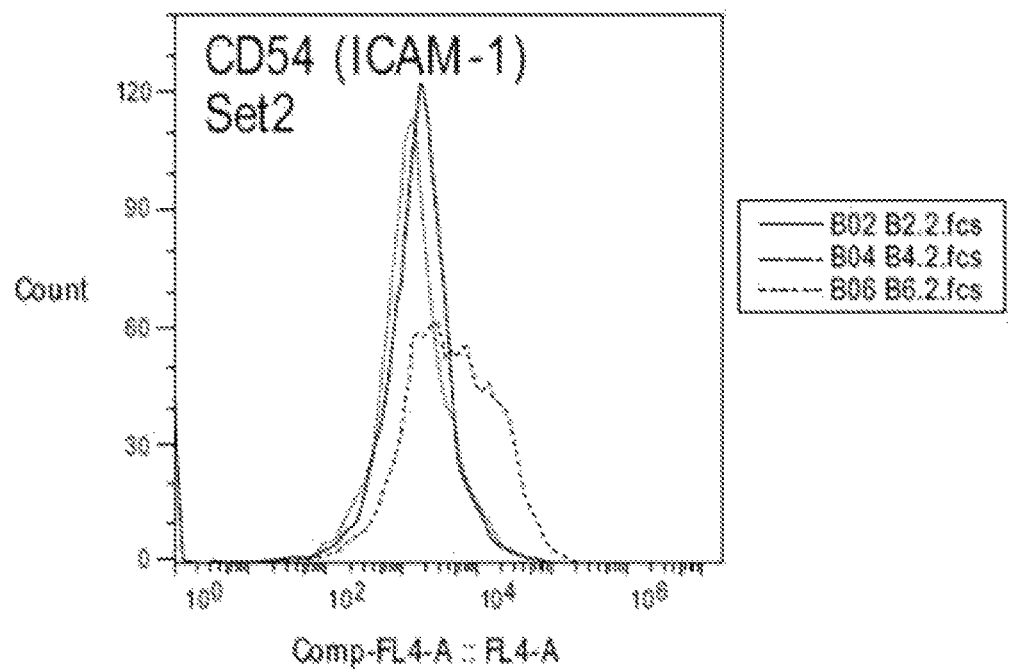

Supernatant from mature DCs were collected for mycoplasma and endotoxin testing 22 hours after pulsing with melanoma cell lysate and 18 hours after addition of maturing agents. No organisms or growth were observed. In addition, ELISA was used to test for IL-12p70 levels, an indicator of the potency of the DCs using 13 dilutions of the DC culture medium supernatant. The concentration of IL-12p70 was 19+/−4 ng/mL, as opposed to the industry standard of 4-6 ng/mL. FIG. 5 shows DC IL-12p70 production relative to that of several comparators. These comparators methods include exposing cells to soft plastic bags, lysing cells with solutions other than a chlorite solution, and do not use the combination of LPS, IFN gamma and R848 to mature cells. Repeated experiments using HOCL solution instead of HOCL powder for the lysis step provided concentrations of IL-12p70 as high as 29 ng/mL.

Cells were further frozen and then thawed at 4° C. to test cell counts and viability after freezing and thawing. These were measured at approximately 16h, 18h, 20h and 22h after beginning of thaw. An extra harvest of non-pulsed DCs were tested in a cryopreservation study, and showed viability at 80%, which is greater than an industry standard of 70% viability. Pre-cryopreservation viability ranged from 85-89%.

Example 7. Inducing Cytokines in Human White Blood Cells with Dengue Virus

Human white blood cells (WBC), including monocytes, dendritic cells and T lymphocytes, were infected with either mock virus or Dengue virus at three different multiplicities of infection (MOI), MOI of 0.1, MOI of 0.5 and MOI of 2 at time=0. Levels (pg/mL) of various cytokines were measured at 48h, 72h and 96h, post-infection. Treatments were performed in triplicate. Results are shown for each time point in Tables 8-11. (M=mock. 0.1, 0.5 and 2 are MOI). Triplicate average of changes between mock and Dengue virus at the tested MOIs was calculated and shown as a percentage in Table 8. This experiment and repeated experiments demonstrate DV induces a 70%-4000% increase in cytokines like GM-CSF, IL-7 and IP-10, as compared to mock virus.

TABLE 8

| Cytokine levels produced by human WBC, 48 h post-Dengue virus infection, measured in picograms/milliliter | | | | | | |
|---|---|---|---|---|---|---|
| | M | M | M | 0.1 | 0.1 | 0.1 |
| IL-1b | 15 | 6 | 6 | 6 | 6 | 6 |
| IL-10 | 4 | 4 | 4 | 4 | 4 | 4 |
| IL-13 | 11 | 11 | 11 | 11 | 11 | 11 |
| IL-6 | 12 | 7 | 9 | 941 | 874 | 788 |
| IL-12 | 19 | 12 | 13 | 14 | 15 | 15 |
| Rantes | 12 | 11 | 11 | 14 | 16 | 18 |
| CCL-11 | 3 | 3 | 3 | 3 | 3 | 3 |
| IL-17 | 18 | 18 | 18 | 18 | 18 | 18 |
| MIP-1a | 123 | 110 | 109 | 183 | 166 | 219 |
| GM-CSF | 5 | 5 | 5 | 5 | 5 | 5 |
| MIP-1b | 83 | 78 | 82 | 123 | 111 | 118 |
| MCP-1 | 1.77e+03 | 1.48e+03 | 1.87e+03 | 12.6e+03 | 10.4e+03 | 9.95e+03 |
| IL-15 | 33 | 33 | 33 | 33 | 33 | 33 |
| IL-5 | 8 | 8 | 8 | 8 | 8 | 8 |
| IFN-g | 5 | 5 | 5 | 6 | 6 | 6 |
| IFN-a | 16 | 12 | 12 | 37 | 35 | 33 |

TABLE 8-continued

Cytokine levels produced by human WBC, 48 h post-Dengue virus infection, measured in picograms/milliliter

| | | | | | | |
|---|---|---|---|---|---|---|
| IL-1Ra | 3.37e+03 | 2.84e+03 | 3.59e+03 | 4.99e+03 | 4.39e+03 | 4.30e+03 |
| TNF-a | 6 | 6 | 6 | 8 | 8 | 8 |
| IL-2 | 9 | 9 | 9 | 9 | 9 | 9 |
| IL-7 | 16 | 8 | 11 | 31 | 27 | 26 |
| IP-10 | 4 | 4 | 4 | 23 | 15 | 18 |
| IL-2R | 31 | 31 | 31 | 54 | 47 | 52 |
| MIG | 38 | 32 | 39 | 29 | 26 | 26 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
| | 0.5 | 0.5 | 0.5 | 2 | 2 | 2 |
| IL-1b | 6 | 6 | 6 | 7 | 7 | 7 |
| IL-10 | 4 | 4 | 5 | 5 | 4 | 4 |
| IL-13 | 11 | 11 | 11 | 11 | 11 | 11 |
| IL-6 | 8.08e+03 | 8.64e+03 | 10.0e+03 | 11.2e+03 | 11.2e+03 | 11.2e+03 |
| IL-12 | 17 | 20 | 19 | 28 | 25 | 25 |
| Rantes | 32 | 56 | 64 | 152 | 135 | 148 |
| CCL-11 | 3 | 3 | 3 | 3 | 3 | 3 |
| IL-17 | 18 | 18 | 18 | 18 | 18 | 18 |
| MIP-1a | 212 | 309 | 328 | 26 | 264 | 259 |
| GM-CSF | 5 | 6 | 7 | 22 | 20 | 21 |
| MIP-1b | 145 | 152 | 142 | 163 | 149 | 155 |
| MCP-1 | 21.8e+03 | 23.4e+03 | 24.2e+03 | 32.0e+03 | 32.0e+03 | 32.0e+03 |
| IL-15 | 33 | 33 | 33 | 68 | 63 | 60 |
| IL-5 | 16 | 18 | 18 | 21 | 21 | 20 |
| IFN-g | 8 | 8 | 8 | 10 | 9 | 10 |
| IFN-a | 47 | 50 | 47 | 67 | 68 | 71 |
| IL-1Ra | 4.55e+03 | 4.88e+03 | 5.14e+03 | 4.13e+03 | 3.42e+03 | 3.82e+03 |
| TNF-a | 16 | 13 | 11 | 21 | 21 | 19 |
| IL-2 | 9 | 9 | 9 | 9 | 9 | 9 |
| IL-7 | 51 | 49 | 47 | 53 | 55 | 54 |
| IP-10 | 39 | 46 | 39 | 218 | 128 | 147 |
| IL-2R | 57 | 69 | 69 | 79 | 76 | 79 |
| MIG | 26 | 31 | 28 | 23 | 22 | 27 |
| IL-4 | 27 | 27 | 27 | 30 | 29 | 30 |
| IL-8 | 17.8e+03 | 17.8e+03 | 17.8e+03 | 17.8e+03 | 17.8e+03 | 17.8e+03 |

TABLE 9

Cytokine levels produced by human WBC, 72 h post-Dengue virus infection, measured in picograms/milliliter

| | M | M | M | 0.1 | 0.1 | 0.1 |
|---|---|---|---|---|---|---|
| IL-1b | 6 | 6 | 6 | 6 | 6 | 6 |
| IL-10 | 4 | 4 | 4 | 4 | 4 | 4 |
| IL-13 | 11 | 11 | 11 | 11 | 11 | 11 |
| IL-6 | 7 | 7 | 7 | 637 | 690 | 737 |
| IL-12 | 12 | 11 | 11 | 12 | 12 | 14 |
| Rantes | 11 | 11 | 11 | 11 | 11 | 11 |
| CCL-11 | 3 | 3 | 3 | 3 | 3 | 3 |
| IL-17 | 18 | 18 | 18 | 18 | 18 | 18 |
| MIP-1a | 96 | 88 | 88 | 84 | 97 | 118 |
| GM-CSF | 5 | 5 | 5 | 5 | 5 | 5 |
| MIP-1b | 83 | 78 | 80 | 85 | 90 | 101 |
| MCP-1 | 5.51e+03 | 5.02e+03 | 4.87e+03 | 21.5e+03 | 22.4e+03 | 21.7e+03 |
| IL-15 | 33 | 33 | 33 | 33 | 33 | 33 |
| IL-5 | 8 | 8 | 8 | 8 | 8 | 8 |
| IFN-g | 5 | 5 | 5 | 6 | 6 | 6 |
| IFN-a | 26 | 23 | 24 | 43 | 46 | 46 |
| IL-1Ra | 6.30e+03 | 5.97e+03 | 6.02e+03 | 6.36e+03 | 6.89e+03 | 6.36e+03 |
| TNF-a | 6 | 6 | 6 | 6 | 6 | 6 |
| IL-2 | 9 | 9 | 9 | 9 | 9 | 9 |
| IL-7 | 8 | 8 | 8 | 23 | 25 | 21 |
| IP-10 | 4 | 4 | 4 | 18 | 14 | 17 |
| IL-2R | 31 | 28 | 20 | 42 | 44 | 42 |
| MIG | 40 | 35 | 35 | 32 | 28 | 27 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
| | 0.5 | 0.5 | 0.5 | 2 | 2 | 2 |
| IL-1b | 6 | 6 | 6 | 6 | 7 | 7 |
| IL-10 | 5 | 5 | 4 | 4 | 5 | 5 |
| IL-13 | 11 | 11 | 11 | 11 | 11 | 11 |

TABLE 9-continued

Cytokine levels produced by human WBC, 72 h post-Dengue virus infection, measured in picograms/milliliter

| IL-6 | 5518 | 8803 | 6841 | 11.2e+03 | 11.2e+03 | 11.2e+03 |
|---|---|---|---|---|---|---|
| IL-12 | 15 | 17 | 16 | 17 | 20 | 22 |
| Rantes | 11 | 16 | 15 | 21 | 88 | 68 |
| CCL-11 | 3 | 3 | 3 | 3 | 3 | 3 |
| IL-17 | 18 | 18 | 18 | 18 | 18 | 18 |
| MIP-1a | 91 | 118 | 106 | 54 | 133 | 87 |
| GM-CSF | 5 | 5 | 5 | 8 | 15 | 15 |
| MIP-1b | 104 | 112 | 101 | 84 | 98 | 101 |
| MCP-1 | 32.0e+03 | 32.0e+03 | 32.0e+03 | 32.0e+03 | 32.0e+03 | 32.0e+03 |
| IL-15 | 33 | 33 | 33 | 33 | 38 | 67 |
| IL-5 | 14 | 15 | 14 | 17 | 19 | 20 |
| IFN-g | 8 | 8 | 7 | 6 | 8 | 8 |
| IFN-a | 62 | 56 | 52 | 61 | 66 | 67 |
| IL-1Ra | 6.90e+03 | 6.76e+03 | 6.01e+03 | 4.33e+03 | 3.89e+03 | 4.39e+03 |
| TNF-a | 6 | 6 | 6 | 6 | 6 | 6 |
| IL-2 | 9 | 9 | 9 | 9 | 9 | 9 |
| IL-7 | 42 | 40 | 40 | 45 | 50 | 48 |
| IP-10 | 42 | 38 | 38 | 104 | 143 | 169 |
| IL-2R | 42 | 47 | 47 | 44 | 56 | 60 |
| MIG | 27 | 25 | 22 | 24 | 19 | 25 |
| IL-4 | 27 | 25 | 24 | 26 | 27 | 29 |
| IL-8 | 17.8e+03 | 17.8e+03 | 17.8e+03 | 17.8e+03 | 17.8e+03 | 17.8e+03 |

TABLE 10

Cytokine levels produced by human WBC, 96 h post-Dengue virus infection, measured in picograms/milliliter

|  | M | M | M | 0.1 | 0.1 | 0.1 |
|---|---|---|---|---|---|---|
| IL-1b | 6 | 6 | 6 | 6 | 6 | 6 |
| IL-10 | 4 | 4 | 4 | 5 | 4 | 4 |
| IL-13 | 11 | 11 | 11 | 11 | 11 | 11 |
| IL-6 | 9 | 9 | 9 | 834 | 734 | 771 |
| IL-12 | 14 | 13 | 13 | 16 | 14 | 14 |
| Rantes | 11 | 11 | 11 | 11 | 11 | 11 |
| CCL-11 | 3 | 3 | 3 | 3 | 3 | 3 |
| IL-17 | 18 | 18 | 18 | 18 | 18 | 18 |
| MIP-1a | 98 | 89 | 119 | 73 | 103 | 122 |
| GM-CSF | 5 | 5 | 5 | 5 | 5 | 5 |
| MIP-1b | 82 | 78 | 99 | 63 | 89 | 99 |
| MCP-1 | 8.19e+03 | 7.61e+03 | 7.10e+03 | 32.0e+03 | 25.3e+03 | 25.6e+03 |
| IL-15 | 33 | 33 | 33 | 33 | 33 | 33 |
| IL-5 | 8 | 8 | 8 | 8 | 8 | 8 |
| IFN-g | 6 | 6 | 7 | 8 | 7 | 6 |
| IFN-a | 27 | 29 | 27 | 52 | 47 | 44 |
| IL-1Ra | 10.9e+03 | 10.9e+03 | 10.2e+03 | 11.0e+03 | 9.57e+03 | 9.56e+03 |
| TNF-a | 6 | 6 | 6 | 6 | 6 | 6 |
| IL-2 | 9 | 9 | 9 | 9 | 9 | 9 |
| IL-7 | 8 | 8 | 8 | 21 | 18 | 14 |
| IP-10 | 4 | 4 | 4 | 29 | 11 | 11 |
| IL-2R | 25 | 23 | 28 | 39 | 36 | 42 |
| MIG | 39 | 40 | 39 | 39 | 24 | 26 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
|  | 0.5 | 0.5 | 0.5 | 2 | 2 | 2 |
| IL-1b | 6 | 6 | 7 | 7 | 6 | 7 |
| IL-10 | 5 | 6 | 6 | 5 | 5 | 5 |
| IL-13 | 11 | 11 | 11 | 11 | 11 | 11 |
| IL-6 | 7026 | 7.47e+03 | 7.65e+03 | 11.2e+03 | 11.2e+03 | 11.2e+03 |
| IL-12 | 16 | 14 | 16 | 16 | 20 | 20 |
| Rantes | 11 | 11 | 11 | 37 | 70 | 68 |
| CCL-11 | 3 | 3 | 3 | 3 | 3 | 3 |
| IL-17 | 18 | 18 | 18 | 18 | 18 | 18 |
| MIP-1a | 79 | 77 | 85 | 60 | 108 | 106 |
| GM-CSF | 5 | 5 | 5 | 12 | 14 | 15 |
| MIP-1b | 85 | 83 | 89 | 67 | 72 | 76 |
| MCP-1 | 32.0e+03 | 32.0e+03 | 32.0e+03 | 32.0e+03 | 32.0e+03 | 32.0e+03 |
| IL-15 | 33 | 33 | 33 | 49 | 43 | 52 |
| IL-5 | 15 | 16 | 16 | 20 | 19 | 18 |
| IFN-g | 7 | 7 | 7 | 7 | 7 | 7 |
| IFN-a | 56 | 58 | 65 | 64 | 64 | 67 |
| IL-1Ra | 7.63e+03 | 7.80e+03 | 8.27e+03 | 5.49e+03 | 4.22e+03 | 4.45e+03 |
| TNF-a | 6 | 6 | 6 | 6 | 6 | 6 |

TABLE 10-continued

Cytokine levels produced by human WBC, 96 h post-Dengue virus infection, measured in picograms/milliliter

| IL-2 | 9 | 9 | 9 | 9 | 9 | 9 |
|---|---|---|---|---|---|---|
| IL-7 | 33 | 37 | 48 | 50 | 45 | 44 |
| IP-10 | 29 | 28 | 33 | 134 | 101 | 104 |
| IL-2R | 39 | 42 | 59 | 52 | 49 | 57 |
| MIG | 19 | 22 | 24 | 20 | 17 | 18 |
| IL-4 | 25 | 24 | 25 | 27 | 27 | 28 |
| IL-8 | 17.8e+03 | 17.8e+03 | 17.8e+03 | 17.8e+03 | 17.8e+03 | 17.8e+03 |

TABLE 11

Relative changes in WBC cytokine levels between mock and Dengue infections

| | MOI 0.1 | | | MOI 0.5 | | | MOI 2 | | |
|---|---|---|---|---|---|---|---|---|---|
| | 48 h | 72 h | 96 h | 48 h | 72 h | 96 h | 48 h | 72 h | 96 h |
| IL-1b | −33% | 0% | 0% | −33% | 0% | 6% | −22% | 11% | 11% |
| IL-10 | 0% | 0% | 8% | 8% | 17% | 42% | 8% | 17% | 25% |
| IL-13 | 0% | 0% | 0% | 0% | 0% | 0% | 0% | 0% | 0% |
| IL-6 | 9.20E+03% | 9.73E+03% | 8.56E+03% | 95.4E+03% | 10.1E+04% | 8.19E+03% | 12.02E+04% | 16.04E+04% | 12.46E+04% |
| IL-12 | 0% | 12% | 10% | 27% | 41% | 15% | 77% | 74% | 40% |
| Rantes | 41% | 0% | 0% | 347% | 27% | 0% | 1179% | 436% | 430% |
| CCL-11 | 0% | 0% | 0% | 0% | 0% | 0% | 0% | 0% | 0% |
| IL-17 | 0% | 0% | 0% | 0% | 0% | 0% | 0% | 0% | 0% |
| MIP-1a | 66% | 10% | −3% | 148% | 16% | −21% | 129% | 1% | −10% |
| GM-CSF | 0% | 0% | 0% | 20% | 0% | 0% | 320% | 153% | 173% |
| MIP-1b | 45% | 15% | −3% | 81% | 32% | −1% | 92% | 17% | −17% |
| MCP-1 | 543% | 325% | 262% | 1255% | 523% | 319% | 1774% | 523% | 319% |
| IL-15 | 0% | 0% | 0% | 0% | 0% | 0% | 93% | 39% | 45% |
| IL-5 | 0% | 0% | 0% | 117% | 79% | 96% | 158% | 133% | 138% |
| IFN-g | 20% | 20% | 11% | 60% | 53% | 11% | 93% | 47% | 11% |
| IFN-a | 163% | 85% | 72% | 260% | 133% | 116% | 415% | 166% | 135% |
| IL-1Ra | 39% | 7% | −6% | 49% | 7% | −26% | 16% | −31% | −56% |
| TNF-a | 33% | 0% | 0% | 122% | 0% | 0% | 239% | 0% | 0% |
| IL-2 | 0% | 0% | 0% | 0% | 0% | 0% | 0% | 0% | 0% |
| IL-7 | 140% | 188% | 121% | 320% | 408% | 392% | 363% | 496% | 479% |
| IP-10 | 367% | 308% | 325% | 933% | 883% | 650% | 4008% | 3367% | 2725% |
| IL-2R | 65% | 62% | 54% | 110% | 72% | 84% | 152% | 103% | 108% |
| MIG | −26% | −21% | −25% | −22% | −33% | −45% | −34% | −38% | −53% |
| IL-4 | 0% | 0% | 0% | 17% | 10% | 7% | 29% | 19% | 19% |
| IL-8 | 0% | 0% | 0% | 0% | 0% | 0% | 0% | 0% | 0% |

Example 8. Additional Virus Manufacturing Protocols

In addition to methods of Example 4, both Vero and FRhL cells are infected using dilutions of the supernatant from blind passage #2, DENV-2 #1710 and DNV-2 #1584, respectively. In order to increase the detection sensitivity, an immunofluorescence staining is developed to detect virus in the cells infected with supernatant from blind passage #2.

Ultracentrifugation is used to concentrate virus when necessary. Following confirmation of virus titer, final product is filtered to remove any cellular debris, tested for absence of any adventitious organisms, and upon final lot released, bottled in 5 ml bottles, and stored at 4° C. until ready for shipment and administration.

Example 9. Collection of PBMC from Donors

Donors (either autologous or HLA-matched allogenic) have a leukapheresis procedure performed at a facility with trained personnel and proper equipment. After the apheresis is complete, the red cells, platelets, and plasma proteins are returned to the donor. The apheresis product is tested at the site (Gram Stain test and Limulus Amoeba Lysis [LAL]) for presence of bacterial contamination. After passing, the collection container (with small testing sample container attached), is barcoded with donor-specific information and placed in an approved shipping container conforming to both FDA and DOT regulations for storage and shipping of non-infectious biological materials. The shipping container is packaged with a cooling element (e.g., solid $CO_2$, Liquid $N_2$), and temperature monitors. The shipping container is a hard plastic flask. A courier transports the container within 24 hours to the GMP manufacturing facility.

Example 10. Manufacture and Use of Dendritic Cells Pulsed with Tumor Antigens Monocytes are separated from other collected white blood cells (e.g., T cells. B cells, NK cells, eosinophils and basophils). This is accomplished with immuno-magnetic selection or, alternatively, by adherence properties. Immunomagnetic selection involves pouring the white blood cells into a sterile plastic column with plastic beads coated with antibodies for immune cell CD surface proteins: (CD4/CD8/CD56, etc.).

An example of immunomagnetic selection is the EasySep Monocyte Enrichment kit available from Stem Cell Technologies (Vancouver, B.C, Canada, www.stemcell.com). To use the EasySep kit, the apheresis product is suspended in sterile PBS and poured into the EasySep plastic column containing Tetrameric antibody complexes with murine antibodies for: human CD2, CD3, CD16, CD19, CD20, CD56, CD66b, CD123, and Glycophorin A. After incubation for 10 minutes, EasySep magnetic particles are added. The cells adhering to the beads removed an electromagnet sorting. The magnet is inverted, and the desired cell fraction (monocytes), is poured into a sterile polystyrene flask for additional processing. Alternately, in a positive adherence selection assay, magnetic beads coated with CD1+/CD14+ antibodies is mixed with monocytes, a magnet is placed against the column, and non-binding cells are flushed out of the column with PBS solution. The monocytes are then washed off the beads. In positive adherence selection, the properties of monocytes to stick to certain surfaces are used to separate them by running the apheresis product down a slanted column.

Alternatively, bone marrow cells are depleted for lymphocytes and MHC Class positive cells by Fluorescent Activated Cell Sorting (FACS) with monoclonal antibodies for CD3, CD4, and CD8. Remaining cells are cultured overnight at 37° C. in a 5% $CO_2$ atmosphere in a basal cell culture medium supplemented with human AB serum. Human AB serum is chosen because it grows cells at a faster rate than other serum types, and serum free media produces DCs with much lower T-cell stimulation capability. After 24 hours, the cells are replated and cultured in the presence of Granulocyte-Macrophage Colony Stimulation Factor (GM-CSF), and recombinant IL-4 at 900 U/ml. After 3 to 4 days, media to be exchanged for fresh cytokine media.

Alternatively, dermal dendritic cells (DDCs) are prepared using the following methods: Keratomes from healthy human volunteers are incubated in a solution of the bacterial proteases Dispase type 2 at a final concentration of 1.2 U/ml in RPMI 1640 for 1 hour at 37° C. After the incubation period, epidermis and dermis are easily separated. Epidermal and dermal sheets are then cut into small (1-10 mm) pieces after several washing with PBS, and placed in RPMI 1640 supplemented with 10% Fetal Bovine Serum (FBS), and placed in 10-cm tissue culture plates. After 2-3 days, pieces of tissue are removed, and the medium collected. Cells migrating out of the tissue sections into the medium are spun down, resuspended in 1-2 ml fresh medium and stained with trypan blue. Further enrichment is achieved by separation on a metrizamide gradient. Cells are layered onto 3-ml columns of hypertonic 14.5% metrizamide and sedimented at 650 g for 10 minutes at room temperature. Low density interphase cells are collected and washed in two successively less hypertonic washes (RPMI 1640 with 10% FBS and 40 mM NaCl) to return cells to isotonicity.

When the monocytes are collected, they may number only a few thousand. The recombinant human growth factors rhuInterleukin-4 (IL-4), and rhuGranulocyte-Macrophage-Colony-Stimulation Factor (GM-CSF), are used in a multistep protocol to accomplish the expansion of DC numbers to the range of 50 million. After the addition of IL-4 and GM-CSF, cells are assessed for and expansion in number and the development of mature-DC markers: ($CD11^+$, $CD80^+$, $CD83^+$), as well as increased expression of both Class I (for presentation of short peptides to $CD8^+$, and Class II MHC complexes (for presentation of longer peptides to $CD4^+$ Helper-Inducer T lymphocytes). After approximately 3-4 days, the number of mature DCs will be measured. For example, the monocyte-enriched fraction is placed in Nuclon-coated Cell Factory (Thermoscientific), with serum-free DC media (CellGro, Inc.), supplemented with GMP-2% human AB serum, 500 IU/ml (approximately 50 ng/ml) rhuIL-4 (CellGenix), with 500 IU/ml (approximately 50 ng/ml) rhuGM-CSF (CellGenix), added after the first 24 hours. Final product is approximately 1 L of total media volume. After about 72 hours of culture, a population of immature DCs are assessed for the following markers: $CD1^+$ $CD11^+$ $CD14^+$.

Example 11. Pulsing Dendritic Cells

A variety of tumor antigen sources are used for high-quality DCs: peptides, lysate from autologous tumors, whole tumor cells, and RNA coding for specific tumor antigens. An excisional biopsy or blood sample containing leukemic or lymphoma cells is obtained by surgery or blood draw followed by a magnetic selection to obtain leukemia/lymphoma cells. Once the tumor cells are obtained, they are barcoded and shipped in approved containers similar to those described for apheresis previously to the GMP facility. Samples may be frozen at −70° C. after passing bacterial contamination tests.

Whole autologous tumor cell lysate is prepared by several methods. To prepare the lysate, the tumor sample may be rewarmed to approximately 35° C. using a water bath or other procedure. The development of automated cell processors like the Miltenyi GentleMACS system allows the sample to be manually minced, suspended in PBS solution, then a pre-selected tissue-specific software-controlled rotor system separates the tumor cells. Cells are added to an enzyme mixture before being transferred to the Miltenyi GentleMACS dissociator. The single-cell suspension can be membrane-lysed with minimal damage to tumor peptides, using a hypochlorite solution, which will kill any residual tumor cells, neutralize $dT_H2$ cytokines an increase immunogenicity for superior CTL affinity, avidity and activation. After adding hypochlorite, culture plates are incubated at 37 degrees Celsius, 5% $CO_2$, for 1 hour, with gentle manual agitation at 30 min to disperse hypochlorite. Cells are washed two time to neutralize the lysis reaction (e.g., with HBSS). Hypochlorite-treated cells may be subjected to subsequent freeze-thaw cycles. Alternatively, the sample does not separate the tumor cells. Instead the sample is left to contain tumor cells and supporting cells (e.g., cells from the tumor microenvironment). Cells are lysed with calcium hypochlorite to eliminate red blood cells and produce apoptotic and necrotic bodies without destroying peptides needed for CTL induction.

Lysate from the GentleMACS is added on the third day of immature DCs production. Immature DCs are co-cultured with tumor lysate for about 16 hours. The final step is maturation with an inflammatory signal. Clinical-Grade LPS (60 EU/ml) (R & D Invivogen), and Interferon-gamma (2000 IU/ml, approximately 100 ng/ml) (R&D Systems) are added to the flask and incubated for approximately 12 hours to mature the pulsed DC. After exposure to LPS, the DCs are assessed for up-regulation of $CD80/CD83^+$ activation markers, and increase production of IL-12p70. In process testing at this stage includes sterility (as previously described), viability (% viable cells by Trypan Blue dye exclusion), and specificity (% DC measured by CD11 c flow cytometry).

After final sterility, specificity, and viability testing, the DCs are transferred to hard plastic containers suitable for freezing at −70° C. in liquid $N_2$, storage up to 1 year, and shipping to the clinic for use. The containers are shipped cool overnight, then re-warmed to 37° C. in a warm-water bath before intravenous administration with a 0.9% NaCl solution concurrent over 30 minutes.

Example 12. Combination Delivery for Treatment of Cancer

Administration of the Dengue Virus is similar to that of other viral vaccine injections. A subject has an area of skin in the shoulder (deltoid) region cleaned with alcohol, then 0.5 ml of the virus is injected under the skin to mimic a mosquito bite. Once the subject has a fever the reaches 38.5° C., after 2-3 days from DV injection, the subject is infused by intralymphatic microcatheter with pulsed (primed) dendritic cells. Injections are repeated until the subject is negative for disease. DC fusions will use cells as manufactured in Example 6.

Example 13. Dengue Virus Cytotoxicity Analysis in Cancer Cell Lines

Two different cancer cell lines, FEMX and 624.28, were each separately co-cultured with CTL, either in the presence or absence of DV supernatant (MOI 2) for six hours, and cell death was quantified for each set of conditions using an LDH release assay. DV supernatant was obtained after infecting WBC with Dengue Virus in a method as described in Example 7. DV supernatant nearly doubled the ability of CTL to kill FEMX cells: 51% of FEMX cells were killed by CTL in the presence of mock supernatant and 91% of FEMX cells were killed by CTL in the presence of DV supernatant. DV supernatant dramatically increased the CTL's ability to kill 624.28 cells: 5% of 624.28 cells were killed by CTL in the presence of mock supernatant and 51% of 624.28 cells were killed by CTL in the presence of DV supernatant. See FIG. 6 and FIG. 7.

Example 14. Analysis of Dengue Virus Activation of Natural Killer Cell Targeting of Cancer Cells The benchmark for NK-cell killing in the industry is on K562 tumors because they are non-antigen matched. Dengue virus treatment was shown to stimulate NK cells to kill about 100% of the K562s (data not shown).

FEMX and 624.28 tumors are usually much harder for NK cells to kill. 624.28 cells are representative of melanoma cells in advanced cancer, with high HLA and are killed by CTL attack. FEMX cells are melanoma cells with normal expression of HLA A2, which is an inhibitor to lysis by NK-92 cells. Thus, FEMX cells are expected to be resistant to NK attack.

FEMX and 624.28 cancer cell lines were separately co-cultured with NK cells, either in the presence or absence of DV supernatant, and cell death was quantified under each condition. Dengue virus doubled the NK cells' ability to deplete cancer cells, leading to >85% destroyed within 10 hours. In addition, combination of DV and dendritic cells provided for more than 90% killing rates within 10 hours. See FIG. 8 and FIG. 9.

High lysis of DV-activated NK against 624.28 cells and FEMX cells was observed. NK cells killed 33% of 624.28 cells in the presence of mock supernatant and 86% of 624.28 cells in the presence of DV supernatant. NK cells killed 48% of FEMX cells in the presence of mock supernatant and 88% of FEMX cells in the presence of DV supernatant.

Example 15. Dengue Virus Induced Supernatants from WBCs

DV supernatant was obtained after infecting WBC with Dengue Virus as described in Example 7. The melanoma 624.28 cell line was exposed to the DV supernatant alone (MOI 2) for six hours and cytotoxicity was measured. As controls, 624.28 cells were exposed to cytotoxic T lymphocytes (CTL) alone or mock virus supernatant. FIG. 10 shows the results of this experiment. Treatment of 624.28 cells with DV supernatants resulted in about 66% cell death with DV supernatant alone.

Example 16. Upregulation of TH1 Cytokines by Dengue Virus

The ability of Dengue virus to increase Class I MHC expression on tumor cells was tested in vitro. In brief, human white blood cells were infected with DENV-2 #1710. Supernatant, no supernatant (control), or mock supernatant (supernatants that generated contact-activation oriented activation) from the infected cells was added to tumor cells. Class I MHC expression on tumor cells exposed to supernatant from infected cells was approximately 60% greater than that of tumor cells exposed to supernatant from non-infected control cells as measured by fluorescence-activated cell sorting (FACS) (See FIG. 11 and Table 12). Furthermore, IFNγ and IFNα levels in the supernatant were measured in triplicates and in pg/ml, and expressed as a percent of baseline pre- and post-infection by Dengue virus. Relative to that of non-infected human white blood cells, IFNγ and IFNα increased by 93% and 415%, respectively, in the supernatant of infected human white blood cells.

TABLE 12

Flow cytometric count of Class I MHC expression in tumor cells.

| Sample Name | Condition | Count | Geometric Mean: Comp − FL2-H |
|---|---|---|---|
| B03 E3.fcs | DV Supernatant | 13134 | 117343 |
| B01 E1.fcs | No DV Supernatant | 13726 | 72838 |

ICAM-1 is required for cell-to-cell contact, i.e., CTL-to-tumor cell. The up-regulation of ICAM-1 increases the adhesion of tumor cells, to allow CTL to adhere to them and kill them. ICAM-1 is required for close CTL-to-tumor contact and lysis. ICAM-1 up-regulation is mediated by TNFα. The ability of Dengue virus to increase ICAM-1 expression on tumor cells was also tested in vitro. In brief, human white blood cells were infected with DENV-2 #1710. Supernatant, no supernatant (control), or mock supernatant (supernatants that generated contact-activation oriented activation) from the infected cells was added to tumor cells. ICAM-1 expression on the surface of tumor cells was measured with flow cytometry. ICAM-1 expression on tumor cells exposed to supernatant from infected cells doubled or tripled relative to tumor cells exposed to supernatant from non-infected control cells (See Table 13 and FIG. 12A and FIG. 12B). Furthermore, TNF alpha levels in the supernatant were measured in triplicates and in pg/ml, and expressed as a percent of baseline pre- and post-infection by Dengue virus. TNF alpha increased by 239% in the supernatant of the infected human white blood cells relative to non-infected human white blood cells.

TABLE 13

ICAM-1 expression on tumor cells.

| Sample Name | Condition | Count | Geometric Mean: Comp – FL4-A |
|---|---|---|---|
| Set 1 | | | |
| B01 B1.2.fcs | Mock DV supernatant | 4507 | 1857 |
| B03 B3.2.fcs | No DV supernatant | 3552 | 1174 |
| B05 B5.2.fcs | DV supernatant | 3632 | 3670 |
| Set 2 | | | |
| B02 B2.2.fcs | Mock DV supernatant | 3770 | 1320 |
| B04 B4.2.fcs | No DV supernatant | 3634 | 1039 |
| B06 B6.2.fcs | DV supernatant | 3490 | 3939 |

Figure 13A:
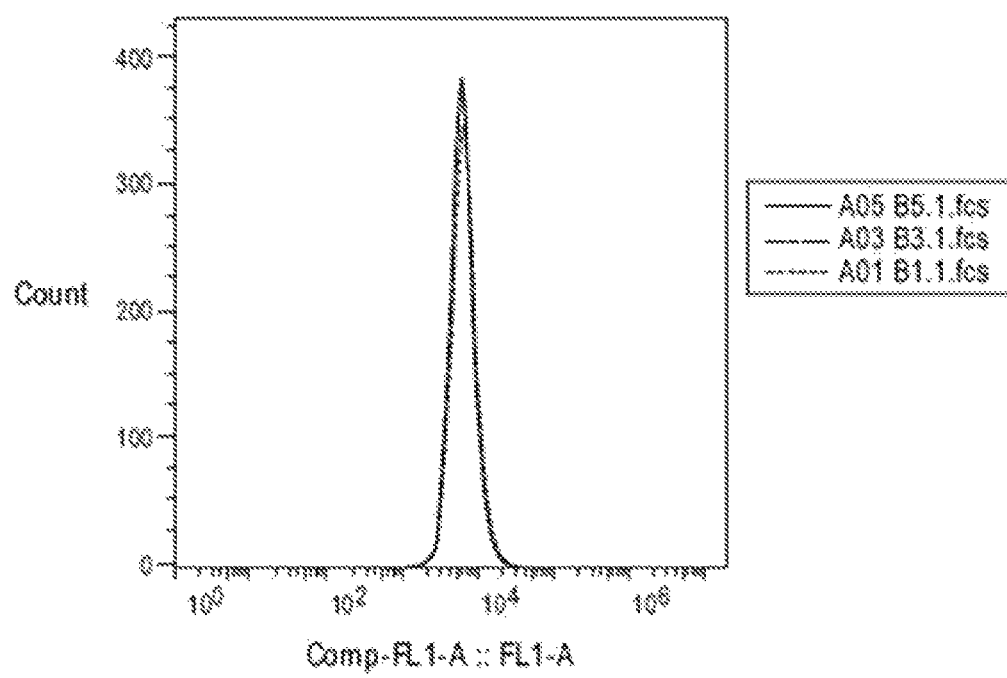
FIG. 13A and FIG. 13B are replicate plots of flow cytometry data measuring the up-regulation of PD-L1 in lung tumor cells. The numbers in the geometric mean refer to a brightness measure of the fluorescence when the antibody is dyed with a florescent marker. This marker is quantified via a typical flow cytometry laser reader.
Figure 13B:
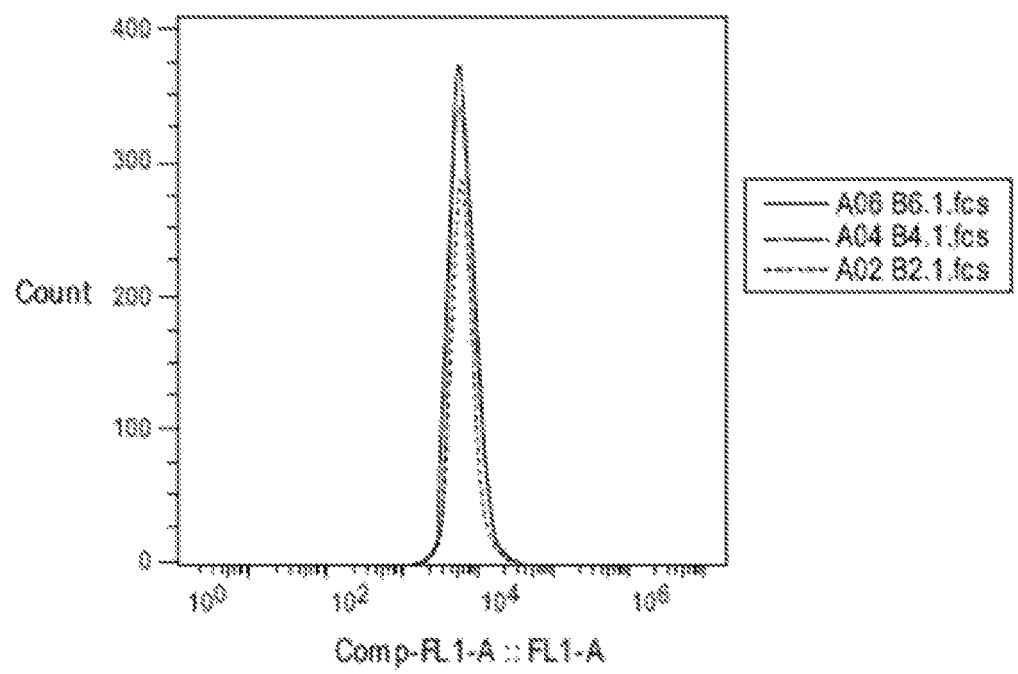
Figure 14A:
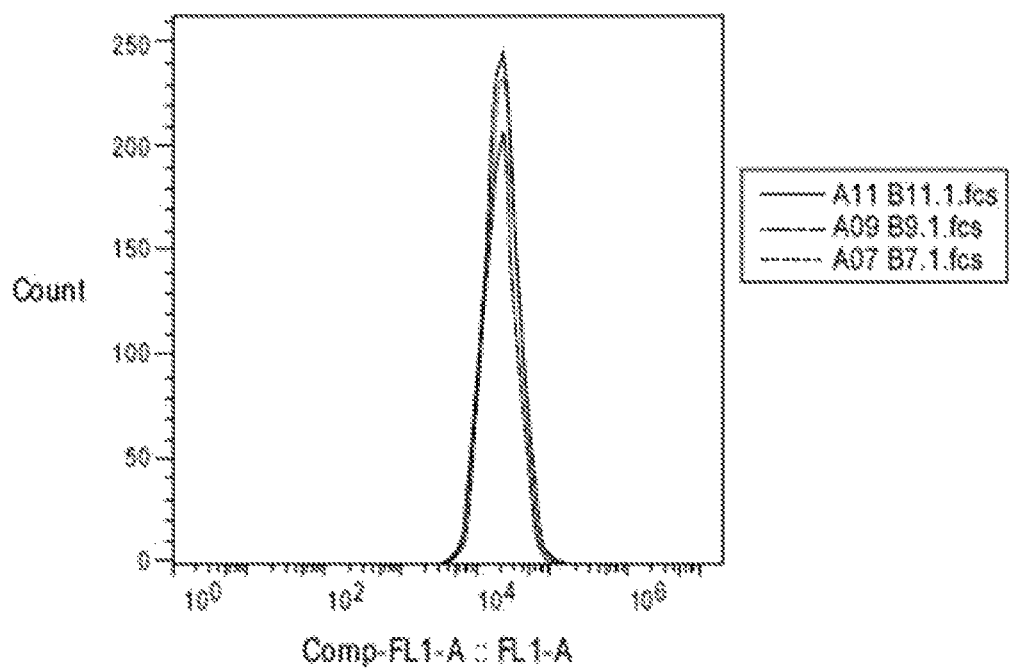
FIG. 14A and FIG. 14B are replicate plots of flow cytometry data measuring the upregulation of PD-1 in breast tumor cells post infection of human white blood cells with Dengue Virus. The numbers in the geometric mean refer to a brightness measure of the fluorescence when the antibody is dyed with a florescent marker. This marker is quantified via a typical flow cytometry laser reader.
Figure 14B:
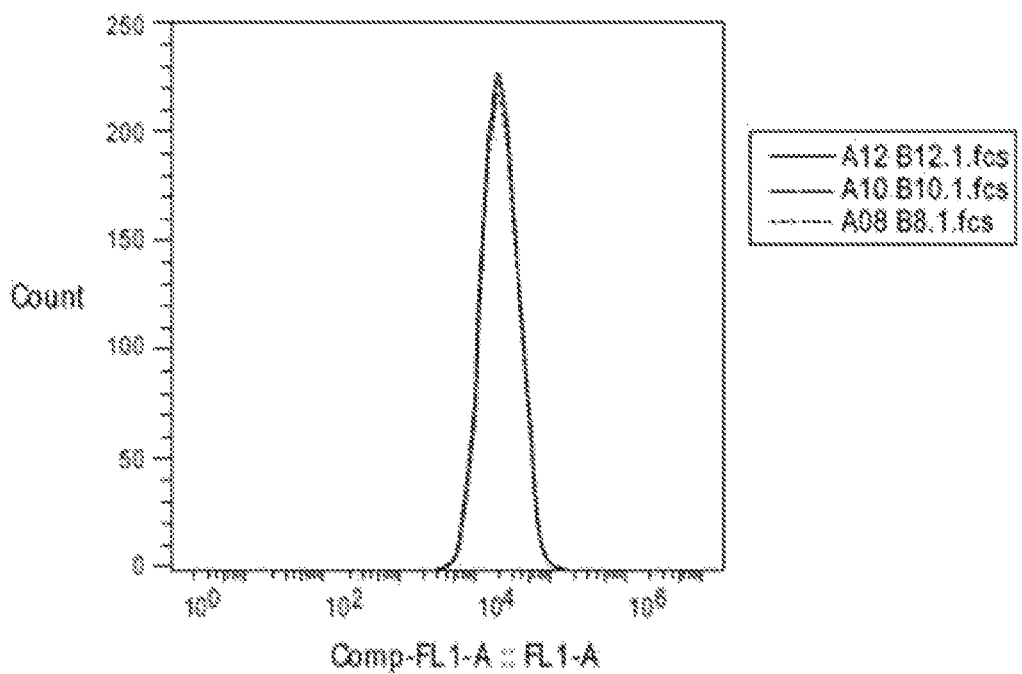

PD-L1 is up-regulated by IFMβ, and is required for checkpoint inhibitors to have a therapeutic effect in killing cancer cells. Human blood cells were infected with DENV-2 #1710 and the level of IFMβ in the resulting supernatant measured and compared to that of non-infected cells. Dengue virus infection increased IFMβ levels by 14,000%. An approximate increase of ~20% was observed of PD-L1 in lung tumor cells (See Table 14 and FIG. 13A and FIG. 13B) and ~3% increase in PD-L1 in breast tumor cells (See Table 15 and FIG. 14A and FIG. 14B), when exposed to supernatant of Dengue virus infected human white blood cells relative to that of non-infected cells.

TABLE 14

PD-L1 expression in lung tumor cells.

| Sample Name | Condition | Count |
|---|---|---|
| Set 1 | | |
| A05 B5.1.fcs | DV supernatant | 5321 |
| A03 B3.1.fcs | No DV supernatant | 3859 |
| A01 B1.1.fcs | Mock DV supernatant | 5061 |
| Set 2 | | |
| A06 B6.1.fcs | DV supernatant | 5363 |
| A04 B4.1.fcs | Mock DV supernatant | 4626 |
| A02 B2.1.fcs | No DV supernatant | 3796 |

TABLE 15

PD-L1 expression in breast cancer cells.

| Sample Name | Condition | Count |
|---|---|---|
| Set 1 | | |
| A11 B11.1.fcs | Mock DV supernatant | 4613 |
| A09 B9.1.fcs | DV supernatant | 4650 |
| A07 B7.1.fcs | No DV supernatant | 4079 |

| Sample Name | Subset Name | Count |
|---|---|---|
| Set 2 | | |
| A12 B12.1.fcs | Mock DV supernatant | 4386 |
| A10 B10.1.fcs | No DV supernatant | 4261 |
| A08 B8.1.fcs | DV supernatant | 4631 |

Additional cytokines involved in reducing or clearing cancer cells are IP-10, IL-12, IL-2R, GM-CSF, IL-7 and IL-15. Infecting human white blood cells with Dengue virus also increased levels of these cytokines in the supernatants of the infected cells. The levels of these cytokines in the supernatant were measured in triplicates and in pg/ml, and expressed as a percent of baseline pre- and post-infection by Dengue virus. The amount of IP-10 was increased 4008% relative to that of control (non-infected) cells). The amount of IL-12 was increased 77%. The amount of IL-2R was increased 152%. The amount of GM-CSF was increased 320%. The amount of IL-7 was increased 496%. The amount of IL-15 was increased 93%.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a solid cancer, comprising administering to a solid cancer an effective amount of a Dengue virus serotype 1 strain, wherein the solid cancer is a melanoma, wherein the Dengue virus serotype 1 strain is 45AZ5, wherein the administering reduces a level of cancer cells, and wherein the Dengue virus serotype 1 strain is present in an amount up to about 90,000 PFU.

2. The method of claim 1, wherein the Dengue virus serotype 1 strain is present in an amount of about 30,000 PFU.

3. The method of claim 1, wherein the melanoma is V600E positive.

4. The method of claim 1, wherein the solid cancer is a refractory cancer.

5. The method of claim 1, wherein the solid cancer is reduced in size by at least about 60% as measured by computed tomography (CT) scan.

6. The method of claim 1, wherein the solid cancer is reduced in size by at least about 80% as measured by computed tomography (CT) scan.

7. The method of claim 1, wherein the solid cancer is reduced in size by at least about 90% as measured by computed tomography (CT) scan.

8. The method of claim 1, wherein the Dengue virus serotype 1 strain is in a volume of about 0.01 ml to 0.1 ml.

9. The method of claim 1, wherein the administering of the Dengue virus serotype 1 strain comprises a subcutaneous injection to the subject.

10. The method of claim 1, wherein the Dengue virus serotype 1 strain is in liquid form, lyophilized form or freeze-dried form.

11. The method of claim 1, wherein the Dengue virus serotype 1 strain is stored in a container.

12. The method of claim 11, wherein the container is a syringe, vial, bottle, flask, or bag.

* * * * *

UNITED STATES PATENT AND TRADEMARK OFFICE
CERTIFICATE OF CORRECTION

| | | |
|---|---|---|
| PATENT NO. | : 12,059,443 B2 | Page 1 of 1 |
| APPLICATION NO. | : 17/130349 | |
| DATED | : August 13, 2024 | |
| INVENTOR(S) | : Bruce W. Lyday | |

It is certified that error appears in the above-identified patent and that said Letters Patent is hereby corrected as shown below:

On the Title Page

In Item (73) Assignee:
The text "Prime Vax Immuno-Oncology, Inc."
Should read --PrimeVax Immuno-Oncology, Inc.--

Signed and Sealed this
Eighth Day of October, 2024

Katherine Kelly Vidal
*Director of the United States Patent and Trademark Office*